(12) United States Patent
Balan et al.

(10) Patent No.: US 10,730,958 B2
(45) Date of Patent: Aug. 4, 2020

(54) PRETREATMENT OF DENSIFIED BIOMASS USING LIQUID AMMONIA AND SYSTEMS AND PRODUCTS RELATED THERETO

(71) Applicant: Board of Trustees of Michigan State University, East Lansing, MI (US)

(72) Inventors: Venkatesh Balan, Sugarland, TX (US); Leonardo da Costa Sousa, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 15/916,223

(22) Filed: Mar. 8, 2018

(65) Prior Publication Data
US 2018/0258190 A1    Sep. 13, 2018

Related U.S. Application Data

(60) Provisional application No. 62/468,944, filed on Mar. 8, 2017.

(51) Int. Cl.
*C08B 15/00* (2006.01)
*C07G 1/00* (2011.01)
(Continued)

(52) U.S. Cl.
CPC .............. *C08B 15/00* (2013.01); *A23K 10/14* (2016.05); *A23K 10/30* (2016.05); *C07G 1/00* (2013.01);
(Continued)

(58) Field of Classification Search
CPC . C08B 15/00; C07G 1/00; C12P 19/14; C12P 7/10; C12P 2201/00; A23K 10/30;
(Continued)

(56) References Cited

U.S. PATENT DOCUMENTS 2,220,624 A    11/1940  Sherrard et al.
3,951,734 A     4/1976  DeHaas et al.
(Continued)

FOREIGN PATENT DOCUMENTS

CA    2573046 A1    1/2006
CA    2610797 A1    12/2006
(Continued)

OTHER PUBLICATIONS

Karlsson, et al., Enzymatic Properties of the Low Molecular Mass Endoglucanases Cel12A (EG III) and Cel45A (EG V) of Trichoderma reesei, Journal of Biotechnology, 2002, pp. 63-78, vol. 99, Elsevier Science B.V.
(Continued)

*Primary Examiner* — Sean C. Barron
(74) *Attorney, Agent, or Firm* — Westman, Champlin & Koehler, P.A.

(57) ABSTRACT

A method to convert at least a majority of native cellulose $I_\beta$ to cellulose $III_I$ in pretreated or untreated densified biomass is disclosed. The densified biomass (cellulosic or lignocellulosic) is pretreated with anhydrous liquid ammonia or liquid ammonia comprising a solution of at least 80% ammonia. The pretreating can be performed at a temperature from about 4° C. to about 140° C. and a pressure from about 14.7 to about 200 psi. In one embodiment, the densified cellulosic converting pretreatment process is followed by lignin extraction (LE). The total moisture content of the densified biomass and the solution is 30% or less and a weight ratio of liquid ammonia to the densified biomass is from about 0.3:1 to about 2:1. Various products and systems are also disclosed.

26 Claims, 31 Drawing Sheets
(16 of 31 Drawing Sheet(s) Filed in Color)

(51) Int. Cl.
  *C12P 19/14* (2006.01)
  *A23K 10/14* (2016.01)
  *A23K 10/30* (2016.01)
  *C08H 7/00* (2011.01)
  *C12P 7/10* (2006.01)

(52) U.S. Cl.
  CPC ............. *C08H 6/00* (2013.01); *C12P 7/10* (2013.01); *C12P 19/14* (2013.01); *C12P 2201/00* (2013.01); *Y02E 50/17* (2013.01); *Y02P 60/877* (2015.11)

(58) Field of Classification Search
  CPC .......... A23K 10/14; C08H 6/00; Y02E 50/17; Y02P 60/877
  See application file for complete search history.

(56) References Cited

U.S. PATENT DOCUMENTS

| | | |
|---|---|---|
| 4,064,276 A | 12/1977 | Conradsen et al. |
| 4,263,744 A | 4/1981 | Stoller |
| 4,370,351 A | 1/1983 | Harper |
| 4,526,791 A | 7/1985 | Young |
| 4,589,334 A | 5/1986 | Andersen |
| 4,600,590 A | 7/1986 | Dale |
| 4,848,026 A | 7/1989 | Dunn-Coleman et al. |
| 4,871,370 A | 10/1989 | Yatsu et al. |
| 5,037,663 A | 8/1991 | Dale |
| 5,047,332 A | 9/1991 | Chahal |
| 5,370,999 A | 12/1994 | Stuart |
| 5,736,032 A | 4/1998 | Cox et al. |
| 6,106,888 A | 8/2000 | Dale et al. |
| 6,524,848 B2 | 2/2003 | McNelly |
| 7,371,926 B2 | 5/2008 | Sticklen et al. |
| 7,494,675 B2 | 2/2009 | Abbas et al. |
| 7,494,792 B2 | 2/2009 | Warzywoda et al. |
| 7,585,652 B2 | 9/2009 | Foody et al. |
| 7,771,565 B2 | 8/2010 | Kirov et al. |
| 7,901,511 B2* | 3/2011 | Griffin ............... C12P 7/10 127/37 |
| 7,910,338 B2 | 3/2011 | Hennessey et al. |
| 7,915,017 B2* | 3/2011 | Dale ............... C12P 7/10 127/37 |
| 8,367,378 B2 | 2/2013 | Balan et al. |
| 8,394,611 B2 | 3/2013 | Dale et al. |
| 8,419,900 B2 | 4/2013 | Baba et al. |
| 8,444,925 B2 | 5/2013 | Baba |
| 8,673,031 B2* | 3/2014 | Dale ............... C10L 5/363 44/589 |
| 9,039,792 B2 | 5/2015 | Dale et al. |
| 9,644,222 B2 | 5/2017 | Balan et al. |
| 9,650,657 B2 | 5/2017 | Chundawat et al. |
| 10,202,660 B2 | 2/2019 | Balan et al. |
| 2003/0044951 A1 | 6/2003 | Sporleder et al. |
| 2006/0130396 A1 | 6/2006 | Werner |
| 2006/0177917 A1 | 8/2006 | Warzywoda et al. |
| 2007/0031918 A1 | 2/2007 | Dunson, Jr. et al. |
| 2007/0037259 A1 | 2/2007 | Hennessey et al. |
| 2007/0192900 A1 | 8/2007 | Sticklen |
| 2007/0287795 A1 | 12/2007 | Ruda et al. |
| 2008/0008783 A1 | 1/2008 | Dale |
| 2008/0256851 A1 | 10/2008 | Lumb |
| 2008/0280236 A1 | 11/2008 | Wright |
| 2009/0011474 A1* | 1/2009 | Balan ............... C12P 7/06 435/99 |
| 2009/0042259 A1 | 2/2009 | Dale et al. |
| 2009/0053770 A1 | 2/2009 | Hennessey et al. |
| 2009/0053771 A1 | 2/2009 | Dale et al. |
| 2009/0093027 A1 | 4/2009 | Balan et al. |
| 2009/0178671 A1 | 7/2009 | Ahring et al. |
| 2009/0318670 A1 | 12/2009 | Dale et al. |
| 2010/0159521 A1 | 6/2010 | Cirakovic et al. |
| 2010/0267999 A1 | 10/2010 | Lau et al. |
| 2011/0192559 A1 | 8/2011 | Venkatesh et al. |
| 2011/0201091 A1 | 8/2011 | Dale |
| 2011/0300269 A1 | 12/2011 | Dale et al. |
| 2012/0064574 A1 | 3/2012 | Tokuyasu et al. |
| 2012/0085505 A1 | 4/2012 | Sabourin |
| 2012/0125548 A1 | 5/2012 | Cohen |
| 2012/0187228 A1 | 7/2012 | Camp et al. |
| 2013/0244293 A1 | 9/2013 | Balan et al. |
| 2013/0247456 A1 | 9/2013 | Dale et al. |

FOREIGN PATENT DOCUMENTS

| | | |
|---|---|---|
| CA | 2752604 A1 | 8/2010 |
| CN | 100999740 A | 7/2007 |
| CN | 101223273 A | 7/2008 |
| CN | 102597247 A | 7/2012 |
| DE | 20301645 U1 | 4/2003 |
| EP | 1247781 A2 | 9/2002 |
| EP | 1690944 A1 | 8/2006 |
| EP | 2411492 B1 | 10/2014 |
| GB | 1310835 | 3/1973 |
| GB | 1381728 | 1/1975 |
| GB | 2122864 A | 1/1984 |
| IN | 249187 | 4/2007 |
| IN | 9645/DELNP/2011 | 2/2013 |
| JP | 2008-161125 A | 7/2008 |
| JP | 2011160753 A | 8/2011 |
| RU | 2215755 C1 | 11/2003 |
| WO | 8500133 | 1/1985 |
| WO | 0061858 A1 | 10/2000 |
| WO | 0132715 A1 | 5/2001 |
| WO | 0237981 A2 | 5/2002 |
| WO | 2007005918 A2 | 1/2007 |
| WO | 2007005918 A3 | 1/2007 |
| WO | 2007130337 A1 | 11/2007 |
| WO | 2008020901 A2 | 2/2008 |
| WO | 2009045527 A1 | 4/2009 |
| WO | 2010098408 A1 | 9/2010 |
| WO | 2010098409 A1 | 9/2010 |
| WO | 2010147218 A1 | 12/2010 |
| WO | 2011028543 A2 | 3/2011 |
| WO | 2011046818 A2 | 4/2011 |
| WO | 2011133571 A2 | 10/2011 |
| WO | 2011133571 A3 | 10/2011 |
| WO | 2012012594 A1 | 1/2012 |
| WO | 2012071312 A2 | 5/2012 |
| WO | 2012088429 A2 | 6/2012 |

OTHER PUBLICATIONS

Kim, et al., Pretreatment of Corn Stover by Aqueous Ammonia, Bioresource Technology, 2003, pp. 39-47, vol. 90, Elsevier Science Ltd.

Klemm, et al., General Considerations on Structure and Reactivity of Cellulose, Comprehensive Cellulose Chemistry: vol. I: Fundamentals and Analytical Methods, Wiley-VHC, 1998, 21 pages, Chapter 2.

Krishnan, et al., Alkali-Based AFEX Pretreatment for the Conversion of Sugarcane Bagasse and Cane Leaf Residues to Ethanol, Biotechnology and Bioengineering, Oct. 15, 2010, 10 pages, vol. 107, No. 3, Wiley Periodicals, Inc.

Kubicek, et al., Enzymatic Deconstruction of Plant Biomass by Fungal Enzymes, Current Opinion in Chemical Biology, Science Direct, 2016, pp. 51-57, vol. 35, www.sciencedirect.com.

Kumar, et al., Does Densification Influence the Steam Pretreatment and Enzymatic Hydrolysis of Softwoods to Sugars?, Bioresource Technology, 2012, pp. 190-198, vol. 121, Elsevier Ltd.

Kumar, et al., Methods for Pretreatment of Lignocellulosic Biomass for Efficient Hydrolysis and Biofuel Production, I&EC Research, 2009, 18 pages, American Chemical Society.

Lamers, et al., Techno-Economic Analysis of Decentralized Biomass Processing Depots, Bioresource Technology, 2015, pp. 205-213, vol. 194, Elsevier Ltd.

Lee, et al., Efficiencies of Acid Catalysts in the Hydrolysis of Lignocellulosic Biomass over a Range of Combined Severity Factors, Bioresource Technology, 2011, pp. 5884-5890, vol. 102, Elsevier Ltd.

(56) References Cited

OTHER PUBLICATIONS

Lewin, et al., The Effect of Liquid Anhydrous Ammonia in the Structure and Morphology of Cotton Cellulose, J. Polymer Sci.: Part C, 1971, pp. 213-229, No. 36, John Wiley & Sons Inc.
Li, et al., Process Optimization To Convert Forage And Sweet Sorghum Bagasse to Ethanol Based On Ammonia Fiber Expansion (Afex) Pretreatment, Bioresource Technology, 2010, pp. 1285-1292, vol. 101, Elsevier Ltd.
Li et al., Responses Of Biomass Briquetting And Pelleting To Water-Involved Pretreatments And Subsequent Enzymatic Hydrolysis, Bioresource Technology, 2013, pp. 54-62, vol. 151, Elsevier Ltd.
Iyer et al., Ammonia Recycled Percolation Process for Pretreatment of Herbaceous Biomass, Applied Biochemistry and Biotechnology, 1996, 12 pages, vol. 57/58.
Lynd et al., Microbial Cellulose Utilization: Fundamentals and Biotechnology, Microbiology and Molecular Biology Reviews, Sep. 2002, pp. 506-577, vol. 66, No. 3, American Society for Microbiology.
Mani et al., Grinding Performance and Physical Properties of Wheat and Barley Straws, Corn Stover, and Switchgrass, Biomass and Bioenergy, 2004, pp. 339-352, vol. 27, Elsevier Ltd.
Mellerowicz et al., Unravelling Cell Wall Formation in the Woody Dicot Stem, Plant Molecular Biology, 2001, pp. 239-274, vol. 47, Kluwer Academic Publishers.
Merino et al., Progress and Challenges in Enzyme Development for Biomass Utilization, Adv Biochem Engin/Biotechnol, pp. 95-120, vol. 108, Springer-Verlag.
Miller et al., Phase I Biomass Enhanced Refined Lignite Demonstration Project, Dec. 15, 2008, 24 pages.
Mittal et al., Ammonia Pretreatment of Corn Stover Enables Facile Lignin Extraction, ACS Sustainable Chem. Eng., 2017, pp. 2544-2561, American Chemical Society.
Mohan et al., Pyrolysis of Wood/Biomass for Bio-oil; A Critical Review, Energy & Fuels, 2006, pp. 848-889, vol. 20, American Chemical Society.
Mohanram et al., Novel Perspectives for Evolving Enzyme Cocktails for Lignocellulose Hydrolysis in Biorefineries, Sustainable Chemical Processes, 2013, 12 pages, vol. 1, No. 15, http://www.sustainablechemicalprocesses.com/content/1/1/15.
Mokomele et al., Ethanol Production Potential from AFEX™ and Steam-Exploded Sugarcane Residues for Sugarcane Biorefineries, Biotechnology for Biofuels, 2018, 21 pages, vol. 11, No. 127, http://doi.org/10.1186/s13068-018-1130-z.
Moniruzzaman et al., Enzymatic Hydrolysis of High-Moisture Corn Fiber Pretreated by AFEX and Recovery and Recycling of the Enzyme Complex, Applied Biochemistry and Biotechnology, 1997, 14 pages, vol. 67, Humana Press Inc.
Mosier et al., Features of Promising Technologies for Pretreatment of Lignocellulosic Biomass, Bioresource Technology, 2005, pp. 673-686, vol. 96, Elsevier Ltd.
Office Action received for Mexican Patent Application No. MX/a/2011/012357, dated Mar. 13, 2013, 1 page.
Office Action received for Mexican Patent Application No. MX/a/2012/012149, dated Aug. 7, 2015, 3 pages.
Office Action Received for Mexican Patent Application No. MX/a/2012/012149, dated Mar. 18, 2016, 2 pages.
Nenkova et al., Production of Phenol Compounds by Alkaline Treatment of Technical Hydrolysis Lignin and Wood Biomass, Chemistry of Natural Compounds, 2008, 4 pages, vol. 44, No. 2, Springer Science+Business Media, Inc.
Nwodo et al., Xylanase Production of Aspergillus niger and Penicillium chrysogenum from Ammonia Pretreated Cellulosic Waste, Research Journal of Microbiology, 2008, pp. 246-253, vol. 3, No. 4, Academic Journals Inc.
Owen et al., An Infrared Study of the Effect of Liquid Ammonia on Wood Surfaces*, Journal of Molecular Structure, 1989, pp. 435-449, vol. 198, Elsevier Science Publishers B.V.

International Search Report and Written Opinion received for PCT Patent Application No. PCT/US2007/010415, dated Oct. 11, 2007, 5 pages.
International Preliminary Report on Patentability received for PCT Application No. PCT/US2010/046525, dated Feb. 28, 2012, 5 pages.
International Search Report and Written Opinion received for PCT Application No. PCT/US2010/046525, dated Apr. 29, 2011, 9 pages.
International Search Report and Written Opinion received for PCT Patent Application No. PCT/US2010/046525, dated Apr. 29, 2011, 9 pages.
International Preliminary Report on Patentability received for PCT Patent Application No. PCT/US2011/033079, dated Nov. 1, 2012, 7 pages.
International Search Report and Written Opinion received for PCT Application No. PCT/US2011/033079, dated Nov. 22, 2011, 8 pages.
International Search Report and Written Opinion received for PCT Patent Application No. PCT/US2011/033079, dated Nov. 22, 2011, 10 pages.
International Search Report and Written Opinion received for PCT Patent Application No. PCT/US2011/061617, dated Jun. 8, 2012, 10 pages.
International Search Report and Written Opinion received for PCT Patent Application No. PCT/US2011/066868, dated Sep. 19, 2012, 6 pages.
Perez et al., TEMPO-Mediated Oxidation of Cellulose III, Biomacromolecules, 2003, pp. 1417-1425, vol. 4, American Chemical Society.
Perry, Chemical Engineers' Handbook, Reaction Kinetics and Reactor Design, 1963, 6 pages, McGraw-Hill, Inc.
Qin et al., Purification and Characterization of Recombinant Endoglucanase of Trichoderma reesei Expressed in *Saccharomyces cerevisiae* with Higher Glycosylation and Stability, Protein Expression and Purification, 2008, pp. 162-167, vol. 58, Elsevier Inc.
Raj et al., Fate of Liquid Ammonia Spilled onto Water, Environmental Science and Technology, Dec. 1978, p. 1422-1425, vol. 12, No. 13, American Chemical Society.
Ray et al., Effect of Pelleting on the Recalcitrance and Bioconversion of Dilute-Acid Pretreated Corn Stover Under Low- and High-Solids Conditions, Biofuels, 2013, pp. 271-284, vol. 4, No. 3.
Richard, Challenges in Scaling Up Biofuels Infrastructure, Science, Aug. 13, 2010, 5 pages, vol. 329, www.sciencemag.org.
Rijal et al., Combined Effect of Pelleting and Pretreatment on Enzymatic Hydrolysis of Switchgrass, Bioresource Technology, 2012, pp. 36-41, vol. 116, Elsevier Ltd.
Sarko et al., Packing Analysis of Carbohydrates and Polysaccharides. 7. Crystal Structure of Cellulose IIII and Its Relationship to Other Cellulose Polymorphs, Sep.-Oct. 1976, 8 pages, vol. 9, No. 5.
Barks et al., Scaling Up and Benchmarking of Ethanol Production from Pelletized Pilot Scale AFEX Treated Corn Stover Using Zymomonas Mobilis 8b, Biofuels, 2016, pp. 253-262, vol. 7, No. 3, Informa UK Limited.
Sheridan et al., Assessment of the Influence of Media Particle Size on the Biofiltration of Odorous Exhaust Ventilation Air from a Piggery Facility, Bioresource Technology, 2002, pp. 129-143, vol. 84, Elsevier Science Ltd.
Silve et al., Obtenção de Insumos Quimicos a Partir do Aproveitamento Integral do Bagaço de Cana, 1995, 120 pages.
Production Techniques to Produce Herbal Extract, Herbal Article—Production Techniques for Herbal Extracts, Oct. 31, 2014, 4 pages.
Topic 3 R&D on Processes for Solid, Liquid and Gaseous Fuels From Biomass, 20th European Biomass Conference and Exhibition, 2012, 26 pages.
Office Action received for Brazilian Patent Application No. 0722418-4, dated Jan. 14, 2013, 3 pages.
Office Action received for European Patent Application No. 07776479.3, dated Dec. 5, 2012, 4 pages.
Office Action received for European Patent Application No. 07776479.3, dated May 30, 2012, 6 pages.

(56) References Cited

OTHER PUBLICATIONS

Notice of Allowance received for U.S. Appl. No. 11/729,632, dated Nov. 16, 2009, 7 pages.
Communication Pursuant to Article 94(3) EPC received for EP Patent Application 11772569.7, dated Jul. 5, 2016, 3 pages.
European Search Report received for Patent Application No. 11772569.7, dated Sep. 19, 2013, 10 pages.
Office Action received for EP Patent Application No. 11772569.7, dated Jan. 23, 2015, 4 pages.
Office Action received for EP Patent Application No. 11772569.7, dated Sep. 28, 2015, 5 pages.
Office Action received for EP Patent Application No. 11772569.7, dated Jul. 29, 2015, 3 pages.
Office Action received for EP Patent Application No. 11772569.7, dated Nov. 30, 2012, 2 pages.
Final Office Action received for U.S. Appl. No. 12/226,763, dated Jan. 10, 2012, 16 pages.
Notice of Allowance received for U.S. Appl. No. 12/226,763, dated Jan. 22, 2013, 7 pages.
Notice of Allowance received for U.S. Appl. No. 12/226,763, dated Oct. 1, 2012, 7 pages.
Final Office Action received for U.S. Appl. No. 12/229,225, dated Jan. 6, 2012, 7 pages.
Non Final Office Action received for U.S. Appl. No. 12/286,913, dated Mar. 1, 2012, 7 pages.
Notice of Allowance received for U.S. Appl. No. 12/286,913, dated Oct. 3, 2012, 9 pages.
Advisory Action received for U.S. Appl. No. 12/763,102, dated Dec. 06, 2013, 3 pages.
Non Final Office Action received for U.S. Appl. No. 12/763,102, dated Dec. 24, 2012, 18 pages.
Restriction Requirement received for U.S. Appl. No. 12/763,102, dated Sep. 17, 2012, 11 pages.
Notice of Allowance received for U.S. Appl. No. 12/976,344, dated Feb. 23, 2012, 7 pages.
Notice of Allowance received for U.S. Appl. No. 12/976,344, dated Mar. 27, 2012, 8 pages.
Non Final Office Action received for U.S. Appl. No. 13/202,011, dated Sep. 27, 2012, 8 pages.
Final Office Action received for U.S. Appl. No. 13/642,052, dated Jun. 18, 2015, 32 pages.
Non Final Office Action received for U.S. Appl. No. 13/642,052, dated Jul. 7, 2016, 30 pages.
Non Final Office Action received for U.S. Appl. No. 13/642,052, dated Jan. 7, 2015, 33 pages.
Notice of Allowance received for U.S. Appl. No. 13/642,052, dated Jan. 5, 2017, 10 pages.
Restriction Requirement received for U.S. Appl. No. 13/642,052, dated Mar. 12, 2014, 10 pages.
Final Office Action received for U.S. Appl. No. 13/886,021, dated Feb. 24, 2015, 31 pages.
Final Office Action received for U.S. Appl. No. 13/886,021, dated Jun. 14, 2016, 33 pages.
Final Office Action received for U.S. Appl. No. 13/886,021, dated Dec. 7, 2017, 24 pages.
Non-Final Office Action received for U.S. Appl. No. 13/886,021, dated Oct. 30, 2015, 22 pages.
Non-Final Office Action received for U.S. Appl. No. 13/886,021, dated Jun. 30, 2014, 37 pages.
Non-Final Office Action received for U.S. Appl. No. 13/886,021, dated Jun. 8, 2017, 23 pages.
Office Action received for Canadian Patent Application No. 2,650,860, dated Jun. 18, 2012, 2 pages.
Office Action received for Canadian Patent Application No. 2,650,860, dated Oct. 24, 2011, 3 pages.
Office Action received for Canadian Patent Application No. 2,737,704, dated Feb. 21, 2013, 3 pages.
Office Action received for Canadian Patent Application No. 2,737,704, dated Jun. 4, 2012, 4 pages.
Office Action received for Canadian Patent Application No. 2,737,704, dated Nov. 5, 2012, 3 pages.
Office Action received for Canadian Patent Application No. 2,760,840, dated Mar. 28, 2012, 3 pages.
Office Action received for Canadian Patent Application No. 2,760,840, dated Jan. 3, 2013, 3 pages.
Office Action received for Canadian Patent Application No. 2,762,985, dated Jul. 6, 2012, 2 pages.
Office Action received for Canadian Patent Application No. 2,797,193, dated Jun. 13, 2014, 3 pages.
Office Action received for Canadian Patent Application No. 2,797,193, dated Jan. 8, 2014, 3 pages.
Office Action received for Canadian Patent Application No. 2,797,193, dated Oct. 1, 2014, 2 pages.
Office Action received for Chinese Patent Application No. 200780025394.4, dated Oct. 13, 2011, 11 pages.
Office Action with English translation received for Chinese Patent Application No. 200780025394.4, dated Oct. 30, 2012, 5 pages.
Patent Examination Report received for Australian Patent Application No. 2010249409, dated Aug. 30, 2012, 4 pages.
Examination Report received for Australian Patent Application No. 2010289797, dated Oct. 30, 2012, 4 pages.
Preliminary Rejection received for Brazilian Patent Application No. BR 10 2018 004591-1, dated Mar. 10, 2019, pages.
Office Action received for Chinese Patent Application No. 201110097994.X, dated Jul. 30, 2012, 25 pages.
Patent Examination Report received for Australian Patent Application No. 2011201768, dated Jun. 21, 2012, 3 pages.
Patent Examination Report received for Australian Patent Application No. 2011242896, dated Oct. 30, 2013, 4 pages.
First Office Action received for Chinese Patent Application No. 201180026819.X, dated Mar. 14, 2014, 22 pages.
Fourth Office Action received for China Patent Application No. 201180026819.X dated Nov. 4, 2015, 14 pages.
Notice of Decision to Grant Received for Chinese Patent Application No. 201180026819.X, dated Apr. 20, 2016, 2 pages.
Office Action received for Chinese Patent Application No. 201180026819.X, dated Nov. 20, 2014, 9 pages of English translation and 8 pages of Official Notice.
Third Office Action received for Chinese Patent Application No. 201180026819.X, dated Apr. 16, 2014, 9 pages.
Examination Report received for Indian Patent Application No. 9093/DELNP/2012, dated Sep. 6, 2017, 8 pages.
Adapa et al., Factors Affecting the Quality of Biomass Pellet for Biofuel and Energy Analysis of Pelleting Process; Int. J. Agric & Biol Eng; Jun. 2013, 12 pages, vol. 6, No. 2, Open access at http://wwwijabe.org.
Adapa et al., Compression Characteristics of Selected Ground Agricultural Biomass; Agricultural Engineering International: the CIGR Ejournal, Manuscript 1347, Jun. 2009, 19 pages,vol. XI.
Agudelo et al., Steam Explosion Pretreatment of Triticale (x Triticosecale Wittmack) Straw for Sugar Production, New Biotechnology, Jan. 2016, 11 pages, vol. 33, No. 1, Elsevier.
Alizadeh, et al., Pretreatment of Switchgrass by Ammonia Fiber Explosion (AFEX), Applied Biochemistry and Biotechnology, 2005, 9 pages, vol. 121-124.
Alvira, et al., Pretreatment Technologies for an Efficient Bioethanol Production Process Based on Enzymatic Hydrolysis: A Review, PubMed, Jul. 2010, 1 page.
Bagga, et al., Evidence for the Occurrence of Polyamine Oxidase in the Dicotyledonous Plant Medicago sativa L. (alfalfa), 1991, pp. 550-554, vol. 10, Springer-Verlag.
Belgacem, et al., Organosolv Lignin as a Filler in Inks, Varnishes and Paints, Industrial Crops and Products, 2003, pp. 145-153, vol. 18, Elsevier Science B.V.
Bergner, et al., Archives of Animal Nutrition, 1980, 19 pages, vol. 30.
Biely, et al., Towards Enzymatic Breakdown of Complex Plant Xylan Structures: State of the Art, Biotechnology Advances, 2016, pp. 1260-1274, vol. 34, www.elsevier.com/locate/biotechadv.

(56) References Cited

OTHER PUBLICATIONS

Bonner, et al., Impact of Sequential Ammonia Fiber Expansion (AFEX) Pretreatment and Pelletization on the Moisture Sorption Properties of Corn Stover, Drying Technology, A International Journal, May 1, 2015, 12 pages.

Campbell, et al., A packed bed Ammonia Fiber Expansion Reactor System for Pretreatment of Agricultural Residues at Regional Depots, Biofuels, Apr. 9, 2014, pp. 23-34, vol. 4, No. 1, Future Science Group, http://dx.doi.org/10.4155/bfs.12.71.

Carolan, et al., Technical and Financial Feasibility Analysis of Distributed Bioprocessing Using Regional Biomass Pre-Processing Centers, Journal of Agricultural & Food Industrial Organization, 2007, 29 pages, vol. 5, Article 10.

Cen, et al., Production of Cellulase by Solid-State Fermentation, Advances in Biochemical Engineering/Biotechnology, 1999, 24 pages, vol. 65, Springer-Verlag.

Chahal, D.S., Bioconversion of Hemicelluloses into Useful Products in an Integrated Process for Food/Feed and Fuel (Ethanol) Production form Biomass, Biotechnology and Bioengineering Symp., 1984, 9 pages, No. 14, John Wiley & Sons.

Chahal, et al., Production of Cellulase in Solid-State Fermentation with Trichoderma reesei MCG 80 on Wheat Straw, Applied Biochemistry and Biotechnology, 1996, 10 pages, vol. 57/58, Humana Press Inc.

Chang, The World Mushroom Industry: Trends and Technological Development, International Journal of Medicinal Mushrooms, 2006, pp. 297-314, vol. 8, Begell House, Inc.

Chundawat, et al., Multifaceted Characterization of Cell Wall Decomposition Products Formed During Ammonia Fiber Expansion (AFEX) and Dilute Acid Based Pretreatments, Bioresource Technology 101, 2010, pp. 8429-8438, Elsevier Ltd.

Chundawat, et al., Proteomics-Based Compositional Analysis Of Complex Cellulase-Hemicellulase Mixtures, Journal of Proteome, Jun. 16, 2011, pp. 4365-4372, vol. 10, American Chemical Society.

Chundawat, et al., Restructuring the Crystalline Cellulose Hydrogen Bond Network Enhances Its Depolymerization Rate, Journal of the American Chemical Society, Jun. 10, 2011, pp. 11163-11174, vol. 133, American Chemical Society.

Chundawat, Ultrastructural and Physicochemical Modifications within Ammonia Treated Lignocellulosic Cell Walls and their Influence on Enzymatic Digestibility vol. I, Chemical Engineering, 2009, 230 pages.

Ciolacu, et al., Studies Concerning the Accessibility of Different Allomorphic Forms of Cellulose, Cellulose, Feb. 2012, pp. 55-68, vol. 19, Springer.

Corma, et al., Chemical Routes for the Transformation of Biomass into Chemicals, 2007, pp. 2411-2502, vol. 107, American Chemical Society.

Dale, et al., Extrusion Processing for Ammonia Fiber Explosion (AFEX), Applied Biochemistry and Biotechnology, 1999, 11 pages, vol. 77-79, Humana Press Inc.

Deshusses, Biological Waste Air Treatment in Biofilters, 1997, Environmental Biotechnology, pp. 335-339, vol. 8.

Eriksson, et al., A Model Explaining Declining Rate in Hydrolysis of Lignocellulose Substrates with Cellobiohydrolase I (Cel7A) and Endoglucanase I (Cel7B) of Trichoderma reesei, Applied Biochemistry and Biotechnology, 2002, 20 pages, vol. 101.

Farrell, et al., Ethanol can Contribute to Energy and Environmental Goal, Science, Jan. 27, 2006, 5 pages, vol. 311, www.sciencemag.org.

Fischer, et al., Nitrogenous Fertilizers from Lignins—A Review, Chemical Modification, Properties, and Uses of Lignin, 2002, p. 167-198.

The Thermophilic Biomass-Degrading Fungus Thielavia Terrestris Co3Bag1 Produces a Hyperthermophilic and Thermostable β-1,4-Xylanase with Exo- and Endo-Activity, Extremophiles, 2017, pp. 175-186, vol. 21, Springer-Japan.

Gibson, The Hierarchical Structure and Mechanics of Plant Materials, Journal of the Royal Society Interface, Aug. 8, 2012, 19 pages, The Royal Society.

Gupta, et al., Fungal Enzymes for Bio-Products from Sustainable and Waste Biomass, Apr. 22, 2016, 38 pages.

Kim, et al., Pretreatment of Biomass by Aqueous Ammonia for Bioethanol Products, Biofuels, Methods and Protocols, Methods in Molecular Biology, 2009, 13 pages, Chapter 6, vol. 581, Humana Press.

Guragain, et al., Evaluation Of Pelleting As A Pre-Processing Step for Effective Biomass Deconstruction And Fermentation, Biochemical Engineering Journal, 2013, pp. 198-2017, vol. 77, Elsevier, www.elsevier.com/locate/bej.

Habibi, et al., Optimization of Cellouronic Acid Synthesis by TEMPO-Mediated Oxidation of Cellulose III from Sugar Beet Pulp, Feb. 2008, pp. 177-185 (not provided), vol. 15.

Himmel, et al., Biomass Recalcitrance: Engineering Plants and Enzymes for Biofuels Production, Science, Feb. 9, 2007, 5 pages, vol. 315, www.sciencemag.org.

Igarashi, et al., Activation of Crystalline Cellulose-To-Cellulose III, Results in Efficient Hydrolysis by Cellobiohydrolase, The FEBS Journal, Feb. 2007, pp. 1785-1792, vol. 274, The Authors Journal.

Ishikawa, et al., Determination of Parameters in Mechanical Model for Cellulose III Fibre, Polymer, 1998, pp. 1875-1878, vol. 39, No. 10, Elsevier.

Kadla, et al., Lignin-based Carbon Fibers for Composite Fiber Applications, Carbon, 2002, pp. 2913-2920, vol. 40, Elsevier Science Ltd.

Kaliyan, et al., Roll Press Briquetting and Pelleting of Corn Stover and Switchgrass, pp. 543-555, vol. 52, No. 2, American Society of Agricultural and Biological Engineers.

Kamm, et al., Biorefineries—Industrial Processes and Products, Status Quo and Future Directions, 2006, 39 pages, Chapter 1, Wiley-VCH Verlag GmbH & Co.

Kamm, et al., Biorefineries—Industrial Processes and Products, Status Quo and Future Directions, 2006, 26 pages, Chapter 2, Wiley-VCH Verlag GmbH & Co.

Karlsson, et al., Enzymatic Degradation of Carboxymethyl Cellulose Hydrolyzed by the Endoglucanases Cel5A, Cel7B, and Cel45A from Humicola insolens and Cel7B, Cel12A and Cel45Acore from Trichoderma reesei, 2002, pp. 32-40, vol. 63, John Wiley & Sons, Inc.

Singhania, et al., Advancement and Comparative Profiles in the Production Technologies Using Solid-State and Submerged Fermentation for Microbial Cellulases, Enzyme and Microbial Technology, 2010, pp. 541-549, vol. 46, Elsevier Inc.

Sluiter et al., Determination of Sugars, Byproducts, and Degradation Products in Liquid Fraction Process Samples, Technical Report, Jan. 2008, 14 pages.

Sousa et al., Next-Generation Ammonia Pretreatment Enhances Cellulosic Biofuel Production, Energy & Environmental Science, 2016, pp. 1215-1223, vol. 9, The Royal Society of Chemistry.

Sousa et al., Centralized Low-Severity EA Treatment can be Integrated With The AFEXTM-Based Depots to Significantly Reduce Enzyme Requirements in the Biorefinery, Great Lakes Bioenergy, 1 page.

Stelte et al.,Recent Developments in Biomass Pelletization—A Review, BioResources, 2012, pp. 4451-4490, vol. 7, No. 3.

Sun et al., Hydrolysis of Lignocellulosic Materials for Ethanol Production: A Review, Bioresource Technology, 2002, pp. 1-11, vol. 83, Elsevier Science Ltd.

Tabil et al., Biomass Feedstock Pre-Processing—Part 1: Pre-Treatment, Biofuel's Engineering Process Technology, 29 pages, Chapter 18.

Tabil et al., Biomass Feedstock Pre-Processing—Part 2: Densification, Biofuel's Engineering Process Technology, 27 pages, Chapter 19.

Teymouri et al., Optimization of the Ammonia Fiber Explosion (AFEX) Treatment Parameters for Enzymatic Hydrolysis of Corn Stover, Bioresource Technology, 2005, pp. 2014-2018, vol. 96, Elsevier Ltd.

Theerarattananoon et al., Effects of the Pelleting Conditions on Chemical Composition and Sugar Yield of Corn Stover, Big Bluestem, Wheat Straw, and Sorghum Stalk Pellets, Bioprocess Biosyst Eng, 2012, pp. 615-623, vol. 35, Springer-Verlag.

(56) References Cited

OTHER PUBLICATIONS

Tumuluru et al., A Review of Biomass Densification Systems to Develop Uniform Feedstock Commodities for Bioenergy Application, 2011, 25 pages, John Wiley & Sons, Ltd.

Tumuluru et al., A Review on Biomass Densification Technologies for Energy Application, Aug. 2010, 96 pages.

Vassilev et al., An Overview of the Chemical Composition of Biomass, Fuel, 2010, pp. 913-933, vol. 89, Elsevier Ltd.

Vennstrøm et al., Beyond Petrochemicals: The Renewable Chemicals Industry, Renewable Resources, 2011, pp. 10502-10509, vol. 50, Wiley-VCH Verlag GmbH & Co.

Wada et al., Neutron Crystallographic and Molecular Dynamics Studies of the Structure of Ammonia-Cellulose I: Rearrangement of Hydrogen Bonding during the Treatment of Cellulose with Ammonia, Cellulose, 2011, pp. 191-206, vol. 18, Springer Science+Business Media B.V.

Wada et al., Polymorphism of Cellulose I Family: Reinvestigation of Cellulose IVI, Jul. 2004, 1 page, vol. 5, Biomacromolecules.

Wahlco, Inc., Ammonia Systems for SCR Applications, 4 pages.

Warzywoda et al., Production and Characterization of Cellulolytic Enzymes from Trichoderma reesei Grown on Various Carbon Sources, Bioresource Technology, 1992, pp. 125-130, vol. 39, Elsevier Science Publishers Ltd.

Wilson, A Cost Analysis for the Densification and Transportation of Cellulosic Biomass for Ethanol Production, Thesis, 2009, 86 pages.

Yatsu et al., Conversion of Cellulose I to Stable Cellulose III, Textile Research Journal, 1986, 8 pages, vol. 56, Sage, http://trj.sagepub.com/content/56/7/419.

Yoon et al., Ammonia-Recycled Percolation Process for Pretreatment of Biomass Feedstock, Applied Biochemistry and Biotechnology, 1995, 15 pages, vol. 51/52.

Yui et al., Structure Conversions of Cellulose III Crystal Models in Solution State: A Molecular Dynamics Study, Cellulose, 2010, pp. 679-691, vol. 17, Springer Science+Business Media B.V.

Zhao et al., Organosolv Pretreatment of Lignocellulosic Biomass for Enzymatic Hydrolysis, 2009, pp. 815-827, vol. 82, Springer-Verlag.

Zugenmaier, Conformation and Packing of Various Crystalline Cellulose Fibers, Progress in Polymer Science, 2001, pp. 1341-1417, vol. 26, Elsevier Science Ltd.

Notice of Allowance dated Jan. 22, 2014 for corresponding related U.S. Appl. No. 13/202,011.

* cited by examiner

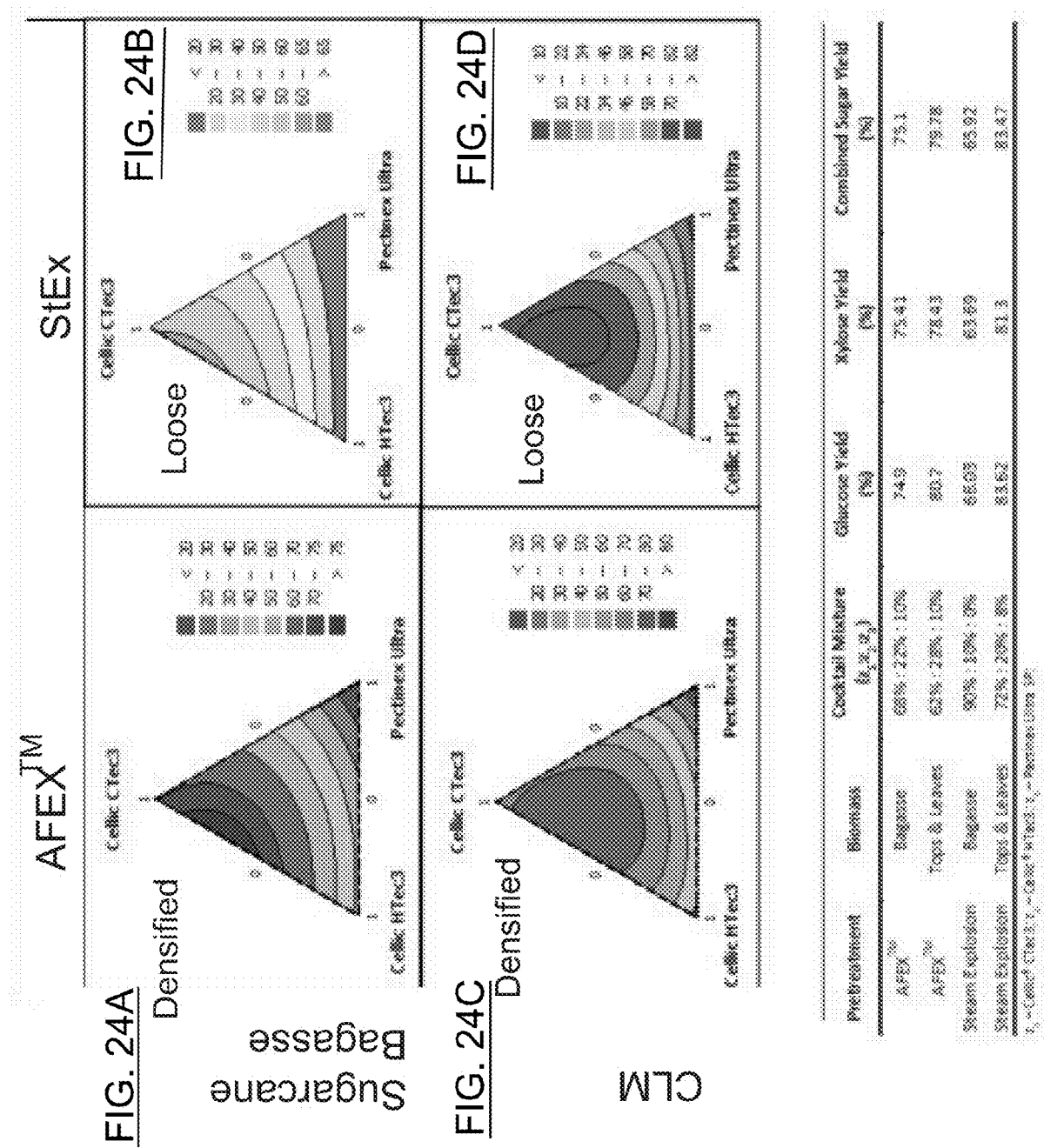

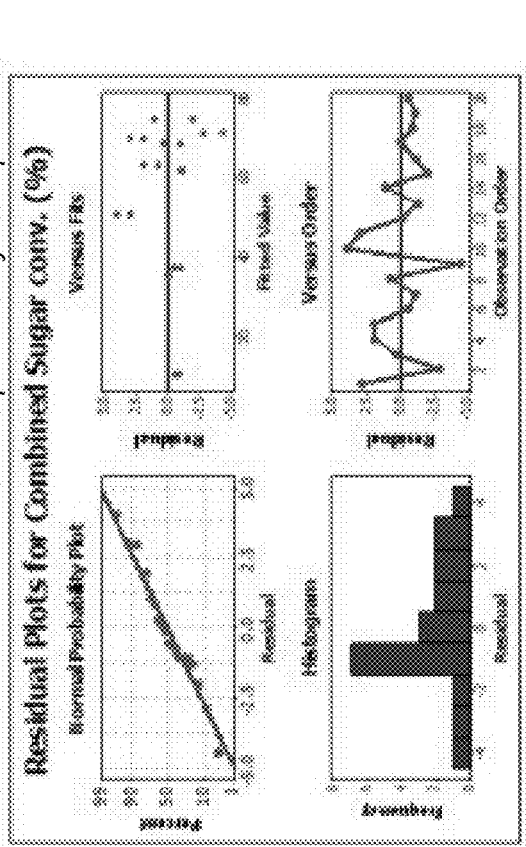
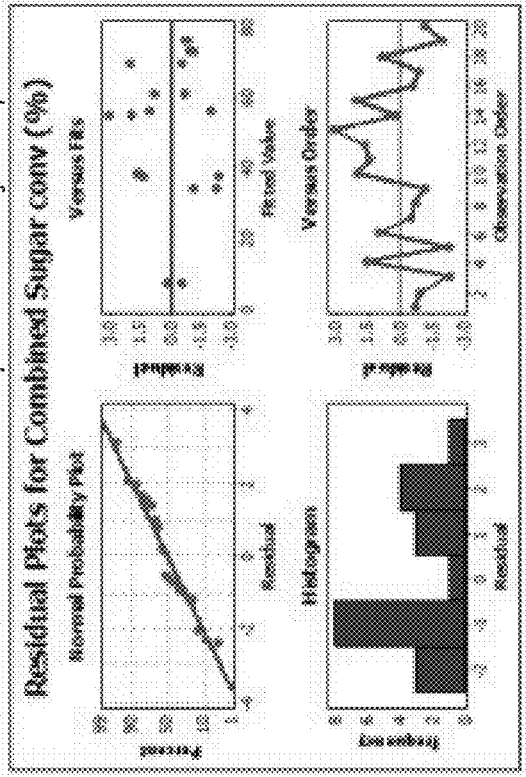
FIG. 25A
FIG. 25B

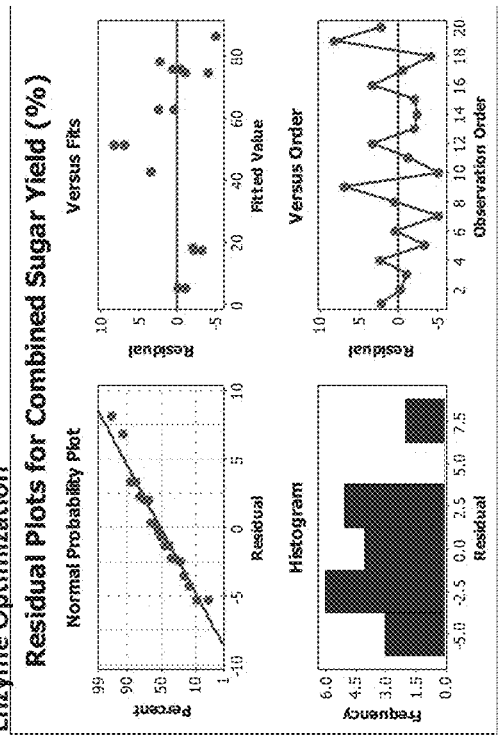
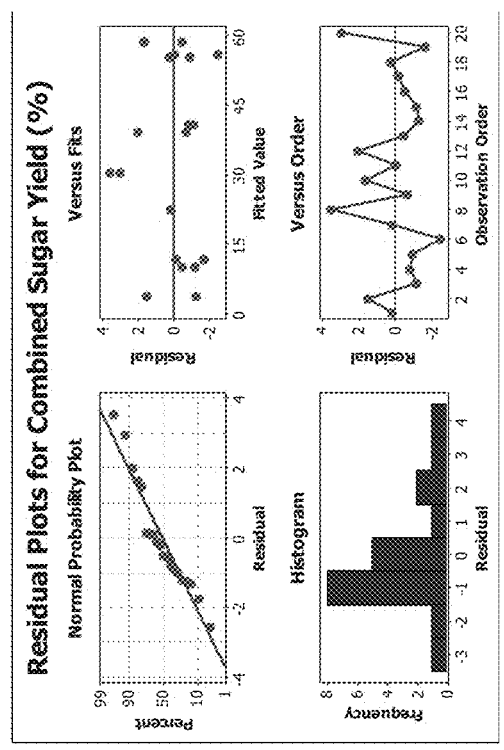
FIG. 25D
FIG. 25C

US 10,730,958 B2

PRETREATMENT OF DENSIFIED BIOMASS USING LIQUID AMMONIA AND SYSTEMS AND PRODUCTS RELATED THERETO

This application claims the benefit under 35 U.S.C. 119(e) of U.S. Provisional Application Ser. No. 62/468,944 filed on Mar. 8, 2017, which is hereby incorporated by reference herein in its entirety.

BACKGROUND

Current attempts to produce cellulosic-based biofuel are cost prohibitive and involve a number of processing steps.

SUMMARY

In one embodiment, a method of pretreating biomass is provided, comprising converting at least a majority of native cellulose $I_\beta$ to cellulose $III_I$ in cellulosic or lignocellulosic densified biomass by pretreating it with anhydrous liquid ammonia or liquid ammonia comprising a solution of at least 80% ammonia at a temperature from about 4° C. to about 140° C. and at pressure from about 14.7 to about 200 psi to generate a pretreated/cellulose III-containing densified biomass (hereinafter "pretreated/CIII-densified biomass"), wherein total moisture content of the biomass and the solution is 30% or less and a weight ratio of liquid ammonia to the densified cellulosic biomass is from about 0.3:1 to about 2:1, such as from about 0.5:1 to about 2:1.

In various embodiments, the densified biomass is densified cellulosic biomass or densified lignocellulosic biomass. In one embodiment, the temperature during pretreatment is maintained at about 18 to 25° C. and the pressure is maintained at atmospheric pressure. In embodiments in which the moisture content is less than 10%, the temperature, pressure and residence time can be configured to cause a complete conversion of cellulose I to cellulose III. In various embodiments, complete conversion can occur at low ammonia to biomass ratios, such as no more than 1.2:1 or 1:1 or even less, such as about 0.3:1.

The novel processes disclosed herein include embodiments in which densification is a first process step following harvesting and, optionally, baling. Densification prior to a liquid ammonia pretreatment which is configured to convert at least a majority up to all of the cellulose I present in the densified biomass to cellulose III (i.e., "densified cellulosic conversion liquid ammonia pretreatment" which is hereinafter referred to as "densified cellulosic conversion pretreatment") provides advantages, as compared with conventional cellulosic conversion ammonia pretreatment processes which utilize loose biomass, including conventional extractive ammonia (EA) processes, which include cellulosic conversion and, optionally, extraction during or after pretreatment of loose biomass. In various embodiments, the densified cellulosic conversion pretreatment optionally includes a lignin extraction (LE) step performed after pretreatment. Conversion of at least a majority of cellulose I to cellulose III produces a pretreated densified biomass containing cellulose III, i.e., "pretreated/CIII-densified biomass." Since cellulose III is an allomorph of cellulose which is more digestible than cellulose I, the pretreated/CIII-densified biomass is more digestible than products resulting from conventional pretreatments in which at least a majority of cellulose I is not converted to cellulose III.

The advantages include, but are not limited to, utilizing less ammonia and reduced temperatures and pressures during pretreatment, higher throughput, reduced pressure rating of the reactor and reduced processing costs, while still converting a majority up to all of the cellulose I present in the densified biomass to cellulose III, but also providing downstream and upstream storage benefits. Downstream benefits include reduced enzyme requirements for hydrolysis, improved sugar conversion rate and sugar yield, and improved extraction. Upstream benefits of storing biomass as densified pretreated biomass include increased biomass stability, reduced storage costs and reduced fire risks as compared with loose or baled biomass.

In one embodiment, the process also includes redensification of densified biomass which has been subject to a densified ammonia conversion pretreatment to form animal feed. In one embodiment, the process can include performing a densified cellulosic conversion pretreatment on untreated densified biomass containing cellulose I or on conventionally pretreated densified biomass containing cellulose I, such as conventional ammonia (e.g., Ammonia Fiber Expansion (AFEX™)) or acid pretreatments, i.e., cellulose reactivation of conventionally pretreated densified biomass.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 24A-24D are contour profiles showing the effect of combinations of commercial enzyme mixtures Cellic® CTec3, Cellic® HTec3, and Pectinex Ultra SP, on the combined sugar yield during 1% glucan loading enzymatic hydrolysis performed at 50° C., 250 rpm for 72 hrs using a fixed total enzyme dosage of 15 mg/g glucan on A) Densified Sugarcane Bagasse/AFEX™, B) Loose Sugarcane Bagasse/StEx, C) Densified Sugarcane Leaf Matter (CLM)/AFEX™ and D) Loose CLM/StEx. The corresponding composition of each optimized cocktail mixture by ratios and corresponding glucose, xylose and combined sugar yield is also provided.

FIGS. 25A-25D are statistical residual plots and regression coefficients used to validate ANOVA assumptions in evaluating the effect of commercial enzyme cocktail mixtures on the monomeric combined sugar yield from 1) AFEX™-pretreated densified sugarcane bagasse, B) AFEX™-pretreated densified CLM, and C) StEx-pretreated loose sugarcane bagasse, showing D) Standard Error of the Regression (S) and Prediction Sum of Squares (PRESS).

DETAILED DESCRIPTION OF THE EMBODIMENTS

Figures 1A, 1B, 1C, 1D:
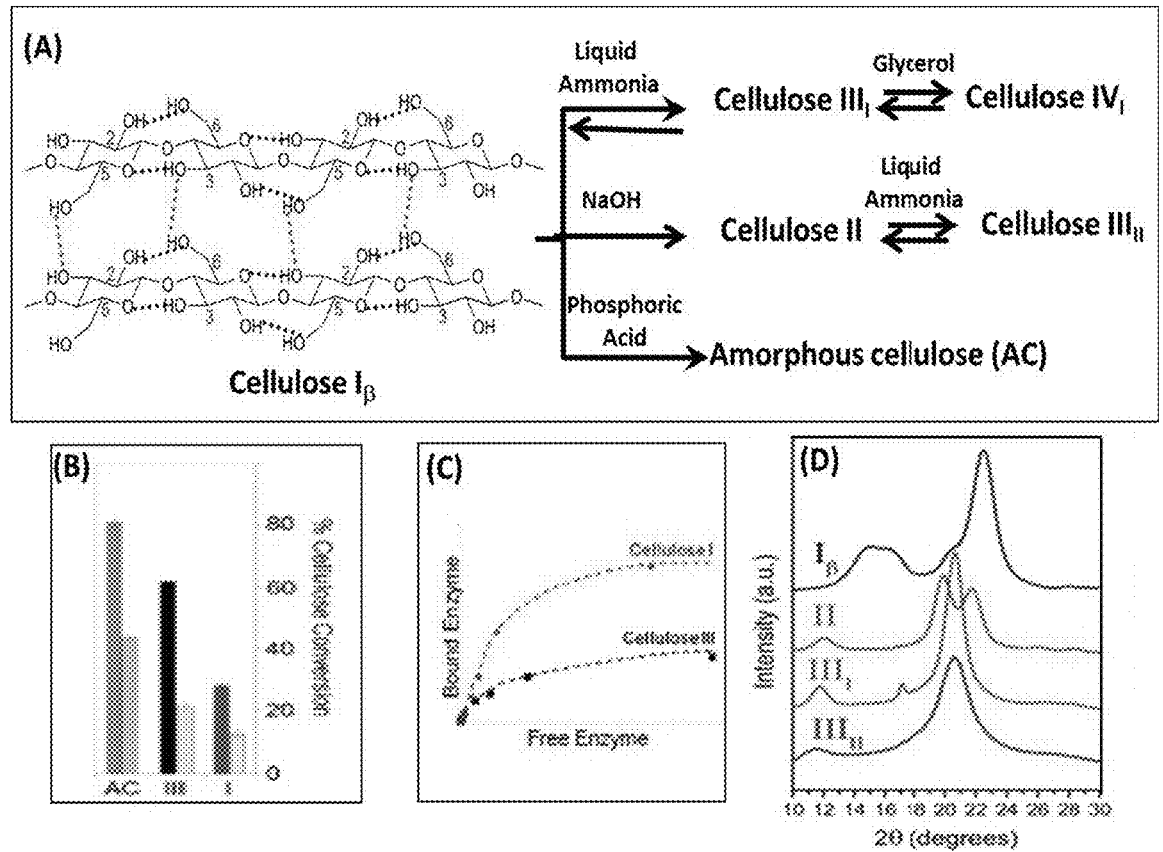
FIGS. 1A-1D are schematic illustrations and graphs showing different allomorphs of cellulose, how they can be generated and certain of their properties including A) conditions at which different allomorphs of cellulose are formed B) three different allomorph of cellulose conversion when using commercial enzymes, C) enzyme binding patterns for Cellulose I and cellulose II and D) an X-Ray Diffraction (XRD) pattern for four different allomorphs of cellulose.

In the following detailed description, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments is defined only by the appended claims.

The term "biomass" as used herein, refers in general to organic matter harvested or collected from a renewable biological resource as a source of energy. The renewable biological resource can include plant materials, bacterial materials, algal materials and/or materials produced biologically, as well as cellulosic materials processed in the pulp and paper industry, cotton fibers and bacterial cellulose, as well as pure cellulose. The term "biomass" is not considered to include fossil fuels, which are not renewable.

The term "plant biomass" or "ligno-cellulosic biomass (LCB)" as used herein is intended to refer to virtually any plant-derived organic matter containing cellulose and/or hemicellulose as its primary carbohydrates (woody or non-woody) available for producing energy on a renewable basis. Plant biomass can include, but is not limited to, agricultural residues such as corn stover, wheat straw, rice straw, sugar cane bagasse and the like. Plant biomass further includes, but is not limited to, woody energy crops, wood wastes and residues such as trees, including fruit trees, such as fruit-bearing trees, (e.g., apple trees, orange trees, and the like), softwood forest thinnings, barky wastes, sawdust, paper and pulp industry waste streams, wood fiber, and the like. Additionally, perennial grass crops, such as various prairie grasses, including prairie cord grass, switchgrass, *Miscanthus*, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature and corn stover is currently the largest source of readily available plant biomass in the United States. When describing the various embodiments and used without a qualifier, the term "biomass" is intended to refer to "plant biomass," i.e., lignocellulosic biomass (LCB).

The term "fiber" as used herein is intended to refer to one piece of biomass whose particle size has been reduced from its original size by any means, including, naturally, i.e., such as by exposure to the elements, by hand and/or by using various machines, such as milling and/or shredding machines.

The term "biochemical" as used herein refers to chemical molecules produced using biological resources. Examples include, but are not limited to, lactic acid, acetic acid, propionic acid, butanol, isobutanol, acetone, and the like. A more complete discussion of biochemical products can be found herein.

The term "biofuel" as used herein, refers to any renewable solid, liquid or gaseous fuel produced biologically and/or chemically, for example, those derived from biomass. Most biofuels are originally derived from biological processes such as the photosynthesis process and can therefore be considered a solar or chemical energy source. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal solid waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "agricultural biofuel", as used herein, refers to a biofuel derived from agricultural crops, lignocellulosic crop residues, grain processing facility wastes or other industrial waste (e.g., wheat/oat hulls, corn/bean fines, out-of-specification materials, brewery spent grains, wheat middling, sugar beet fiber, soybean meal, and other cereal or seed covers, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG), distiller's dry grain with solubles (DDGS), and syrup from ethanol production facilities, etc.), and the like. Examples of livestock industries include, but are not limited to, beef, pork, turkey, chicken, egg and dairy facilities. Examples of agricultural crops include, but are not limited to, any type of non-woody plant (e.g., cotton), grains such as corn, wheat, soybeans, sorghum, CLM, barley, oats, rye, and the like, herbs (e.g., peanuts), short rotation herbaceous crops such as switchgrass, alfalfa, and so forth.

The term "pretreatment step" as used herein, refers to any step intended to alter native or densified biomass (as defined herein) so it can be more efficiently and economically converted to reactive intermediate chemical compounds such as sugars, organic acids, etc., which can then be further processed to a variety of end products such as ethanol, isobutanol, long chain alkanes organic acids, etc. Pretreatment can reduce the degree of crystallinity of a polymeric substrate, reduce the interference of lignin with biomass conversion by hydrolyzing some of the structural carbohydrates, thus increasing their enzymatic digestibility and accelerating the degradation of biomass to useful products. Pretreatment methods can utilize acids of varying concentrations, including dilute acid pretreatments, concentrated acid pretreatments (using, for example, sulfuric acids, hydrochloric acids, organic acids, and the like) and/or alkali such as ammonia and/or ammonium hydroxide and/or calcium hydroxide and/or sodium hydroxide and/or lime, and the like. Pretreatment methods can additionally or alternatively utilize hydrothermal treatments including water, heat, steam or pressurized steam pretreatments, including, but not limited to, hydro-thermolysis pretreatment and liquid hot water pretreatment, further including, for example, acid catalyzed steam explosion (StEx) pretreatment. Pretreatment can occur or be deployed in various types of containers, reactors, pipes, flow through cells and the like. Most pretreatment methods will cause the partial or full solubilization and/or destabilization of lignin and/or hydrolysis of hemicellulose to pentose sugars. Further examples of pretreatment include, but are not limited wet oxidation, organosols pretreatment and mechanical extrusion.

The term "mechanical process" as used herein refers to any non-chemical process that causes a physical change in structure and/or function of native biomass. Such a change includes, but is not limited to, particle size reduction of native biomass to produce fibers, which can be accomplished using various types of machines (e.g., bale busters, hammer mill, Wiley mill, and the like) or by grinding (e.g., cylindrical grinding, internal grinding, centerless grinding, surface grinding, and combinations thereof). Additionally, multiple different implements may be employed to perform the grinding. For example, ball mills, rod mills, autogenous mills, semi-autogenous grinding mills, pebble mills, high pressure grinding rolls, brush stone mills, vertical shaft impactor mills (VSI mill), tower mills, and combinations thereof, may be used. Densification is one example of a mechanical process.

The term "Ammonia Fiber Expansion" (hereinafter "AFEX™") pretreatment" as used herein, refers to a process for pretreating lignocellulosic biomass with liquid and/or vapor (gaseous) ammonia to solubilize lignin from plant cell walls and redeposit it from in between plant cell walls to the surface of the biomass. An AFEX™ pretreatment disrupts the lignocellulosic matrix, thus modifying the structure of lignin, partially hydrolyzing hemicellulose, and increasing the accessibility of cellulose and the remaining hemicellulose to subsequent enzymatic degradation.

However, in contrast to many other pretreatments, the lower temperatures and non-acidic conditions of the AFEX™ process prevents lignin and/or sugars from being converted into furfural, hydroxymethyl furfural (HMF), and organic acids that could negatively affect microbial activity. The AFEX™ process further expands and swells cellulose fibers and further breaks up amorphous hemi-cellulose in lignocellulosic biomass (LCB). These structural changes open up the plant cell wall structure enabling more efficient and complete conversion of LCB to value-added products, while preserving the nutrient value and composition of the material. In one embodiment, the EA treatment serves as a pretreatment.

The term "gaseous AFEX™ pretreatment" as used herein, refers to an AFEX™ pretreatment as defined herein, which uses gaseous ammonia rather than liquid ammonia. By allowing hot ammonia gas, i.e., ammonia vapors (with or without a carrier) to condense directly on cooler biomass, the biomass heats up quickly when the ammonia and biomass come into intimate contact.

The term "extractives" as used herein refers to components in a cellulosic or lignocellulosic material that are removable with a solvent. Such extractives include, but are not limited to, biomass degraded products, plant metabolites, ash, proteins and sugar polymers, further including lignin (present in lignocellulosic biomass).

The term "conventional extractive ammonia" or "EA" or "EA/cellulosic conversion" as used herein, refers to a pretreatment that not only removes extractives from loose biomass during a low moisture liquid ammonia biomass treatment, but also converts at least a majority of cellulose I to cellulose III. In an EA treatment, the moisture content, residence time, temperature and ammonia to biomass ratio are configured to allow for conversion of a majority (i.e., at least 50%) to substantially all (99%-99.9%) to all (about 100% up to 100%) of the cellulose I present in the biomass being treated to cellulose III. Those skilled in the art understand that deviation from a proper combination of conditions (moisture content, temperature, residence time and ammonia to biomass ratio) will prevent a majority, or, in some cases, any of the cellulose I from being converted to cellulose III. For example, regardless of any other conditions, if the moisture content of the mixture (moisture inherent in the biomass and any moisture added to the biomass in any form) is too high, i.e., over 40%, no conversion takes place. Such a process would, therefore, fall outside the definition of an EA pretreatment. Examples of such non-extractive ammonia pretreatments include AFEX™ pretreatment methods. See, for example, Sousa L., et al., *Next-Generation Ammonia Pretreatment Enhances Biofuel Production*, Energy Environ. Sci., DOI: 10.1039/c5ee03051j (Feb. 23, 2016), 9 pages (hereinafter "Sousa Article"), which states that, "Other ammonia-based pretreatments such as ammonia fiber expansion (AFEX™) (trade mark of MBI International, Lansing, Mich.) and ammonia-recycle percolation (ARP) do not lead to CIII formation because they employ high moisture contents and/or low ammonia-to-biomass ratios." In this testing, "AFEX™-CS (AFEX-Corn Stover) was used as a control, as AFEX™ does not physically remove lignin and does not generate CIII." (See Sousa Article at Page 2, Col. 1). It is to be understood that the removal of extractives during pretreatment can be accomplished with or without solvents, depending on the ammonia to biomass loading.

The term "steam explosion" or "StEx" as used herein refers to a pretreatment that involves heating loose biomass with superheated steam followed by a sudden decompression to yield a slurry, referred to "whole slurry" herein. Steam explosion can be assisted by impregnation with an acid catalyst, such as sulfuric acid or sulfur dioxide. If no impregnating agent is used, the process is catalyzed via autohydrolysis.

The terms "densified cellulosic conversion liquid ammonia pretreatment" or "densified cellulosic conversion pretreatment" as used herein refers to a pretreatment of densified biomass particulates which produces pretreated/CIII-densified biomass. As with the EA pretreatment defined above, in a densified cellulosic conversion pretreatment, the moisture content, residence time, temperature and ammonia to biomass ratio are configured to allow for conversion of a majority (i.e., at least 50%) to substantially all (99%-99.9%) to all of the cellulose I present in the densified biomass being treated to cellulose III. Those skilled in the art understand that deviation from a proper combination of conditions (moisture content, temperature, residence time and ammonia to biomass ratio) will prevent a majority, or, in some cases, any of the cellulose I from being converted to cellulose III. For example, regardless of any other conditions, if the moisture content of the mixture (moisture inherent in the biomass and any moisture added to the biomass in any form) is too high, i.e., over 40%, no conversion takes place. Such a process would, therefore, fall outside the definition of a densified cellulosic conversion pretreatment (For additional examples, see definition of EA above).

The terms "extractive densified cellulosic conversion liquid ammonia pretreatment" or "extractive densified cellulosic conversion pretreatment" as used herein, refer to a densified cellulosic conversion pretreatment which also removes at least some extractives. It is to be understood that the removal of extractives during pretreatment can be accomplished with or without solvents, depending on the ammonia to biomass loading. Removal of extractives after pretreatment is accomplished with solvents.

The terms "densified cellulosic conversion liquid ammonia pretreatment with lignin extraction (LE)" or "densified cellulosic conversion-LE pretreatment" as used herein refers to a pretreatment of densified biomass particulates which produces pretreated/lignin extracted/CIII-densified biomass ("pretreated-LE/CIII-densified biomass"). Such a pretreatment is essentially a "densified cellulosic conversion pretreatment" followed by a lignin extraction step.

The term "pretreated/cellulose III-containing densified biomass" or "pretreated/CIII-densified biomass" as used herein refers to densified biomass which has been pretreated in a process that converted at least a majority of its cellulose I to cellulose III.

The term "loose biomass" as used herein refers to cellulosic or lignocellulosic biomass that has not been subject to sufficient compression or extrusion to be formed into a single densified biomass particulate, i.e., densified biomass. Biomass that has been formed into bales (e.g., round, cubic, etc.) and then unbaled for use in a facility is still considered to be "loose biomass" and is therefore encompassed within this definition. Biomass that has been subject to chopping or other particle size reducing mechanical processes are also considered to be loose biomass.

The terms "compacted biomass" or "compressed bales" or "compacted bales" as used herein refer to loose biomass or bales which have been compressed, i.e., compacted, to reduce empty space between the loose biomass fibers. Loose biomass fibers are highly elastic and require an external force to be applied continuously to maintain a state of compaction. For example, baled biomass requires compaction forces to be constantly applied externally by twine or plastic strips to maintain the shape of the bale. In this way, loose biomass fibers, such as loose biomass fibers collected from various plant sources, are not chemically or physically adhered/bound to each other in the same way densified biomass. As such, a considerable amount of space still exists between the various plant fibers in baled biomass. In addition, given the elastic nature of loose biomass fibers, the compacted bales inherently start reverting back to their original configuration once the compression is released, such as when the twine or plastic strips are cut, wherein the space between fibers again increases.

The term "particulate" or "biomass particulate" or "densified biomass particulate" or "densified biomass" as used herein refers to densified (i.e., solid) biomass formed from a plurality of loose biomass fibers which are subject to a mechanical densification process which either compresses or extrudes the biomass to form a single particulate product (or products) which is dividable into separate pieces. Since the densified fibers in the particulate are no longer elastic, the particulate retains its shape, i.e., does not begin to expand once compression is released, i.e., after the densification process is stopped. A particulate can be hydrolysable or non-hydrolysable and can range in size from small, dense microscopic particles (larger than powders) to pellets or large objects, such as bricks, or larger, such as densified bales or larger, with any suitable mass. The specific geometry and mass will depend on a variety of factors including the type of biomass used, the amount of compression used to create the particulate, the desired length of the particulate, and the particular end use. As such, when the term "densified biomass" is used it is intended to refer to one or more "densified biomass particulates." As used herein, a densified biomass particulate is intended to include particulates made with and without added binders. Particulates made without binders are generally made from lignocellulosic biomass, with the natural constituents of the biomass, such as lignin and proteins, conferring natural binding capacity when subjected to certain temperatures and moisture content.

The term "briquette" as used herein refers to a densified biomass particulate which is a compressed particulate of various shapes (e.g., hexagon, cylindrical, cuboid, etc.) which retains its shape even after the compression is released. Briquettes are made in briquette machines under modest pressure, are typically about to 2 to about 3 orders of magnitude larger than pellets, and typically more brittle than pellets. A briquette retains its shape after exiting the briquette machine.

The term "pellet" as used herein refers to a densified biomass particulate which is an extruded particulate, i.e., a compressed particulate formed by a shaping process in which biomass is forced through a die (e.g., a cylindrical die) or a rotating press at pressures about 3.5 times greater than those used to make briquettes. As such, a given amount of pellets has a greater bulk density than a given amount of briquettes. A pellet retains its shape even after the extrusion is complete.

The term "whole slurry" as used herein refers a slurry containing particulates of varying sizes that have not been removed via separation.

The term "bulk density" as used herein, refers to the mass or dry weight of a quantity of fibers or particulates divided by the total volume they occupy (mass/volume). Therefore, bulk density is not an intrinsic property of the fibers or particulates, as it is changeable when the fibers or particulates are subjected to movement from an external source. The volume measurement is a combination of the fiber or particulate volume (which includes the internal pore volume of a fiber or particulate) and the intra-particle void volume. Bulk density=intrinsic density (of each fiber or particulate)× (1−voids fraction). For a given intrinsic fiber or particulate density, therefore, the bulk density depends only on the void fraction, which is variable.

The term "high solids loading" as used herein refers to any enzymatic hydrolysis biomass loading greater than 5 wt % (g solids/100 g total reaction weight).

The term "moisture content" as used herein, refers to percent moisture present in biomass. Moisture content can be expressed on a dry weight basis (dwb) or a total weight basis, i.e., moisture wet basis (mwb). The total moisture content is calculated as grams of liquid, such as water per gram of biomass (biomass dry matter plus water) liquid times 100%. However, when used without qualification herein, the % moisture content refers to a dry weight basis.

The term "flowability" as used herein refers to the ability of particulates to flow out of a container using only the force of gravity. A product having increased flowability, therefore, would flow out of the container at a faster rate as compared to a product having lower flowability.

The term "logistical properties" as used herein refers to one or more properties of a particulate related to storage, handling, and transportation, which can include, but are not limited to stability, shelf life, flowability, high bulk density, high true density, compressibility, durability, relaxation, spring back, permeability, unconfined yield strength, and the like.

Nearly all forms of lignocellulosic biomass, i.e., plant biomass, such as monocots, comprise three primary chemical fractions: hemicellulose, cellulose, and lignin, while cellulosic biomass includes mostly cellulose with trace amounts of hemicellulose, but no lignin. Hemicellulose is a polymer of short, highly-branched chains of mostly five-carbon pentose sugars (xylose and arabinose), and to a lesser extent six-carbon hexose sugars (galactose, glucose and mannose). Dicots, on the other hand, have a high content of pectate and/or pectin, which is a polymer of alpha-linked glucuronic acid. Pectate may be "decorated" with mannose or rhamnose sugars, also). These sugars are highly substituted with acetic acid.

Because of its branched structure, hemicellulose is amorphous and relatively easy to hydrolyze (breakdown or cleave) to its individual constituent sugars by enzyme or dilute acid treatment. Cellulose is a linear polymer of glucose sugars, much like starch, which is the primary substrate of corn grain in dry grain and wet mill ethanol plants. However, unlike starch, the glucose sugars of cellulose are linked together by β-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers. Lignin, which is a polymer of phenolic molecules, provides structural integrity to plants, and remains as residual material after the sugars in plant biomass have been fermented to ethanol. Lignin is a by-product of alcohol production and is considered a premium quality solid fuel because of its zero sulfur content and heating value, which is near that of sub-bituminous coal.

Typically, cellulose makes up 30 to 50% of residues from agricultural, municipal, and forestry sources. While cellulose is more difficult to convert to ethanol than hemicellulose, it is the sugar polymers of hemicellulose which can be more readily hydrolyzed to their individual component sugars for subsequent fermentation to ethanol. Although hemicellulose sugars represent the "low-hanging" fruit for conversion to ethanol, the substantially higher content of cellulose represents the greater potential for maximizing alcohol yields, such as ethanol, on a per ton basis of plant biomass.

As noted above, the hemicellulose fraction of biomass contains hexose and pentose sugars, while the cellulose fraction contains glucose. In current AFEX™ pretreatment operations, only limited hemicellulose conversions are obtained. It is further known that of the sugars extracted, about 30 to 35% is xylose and about 35 to 40% is glucose (most all of which is currently converted only in post-pretreatment steps). Overall conversions, as well as over-all ethanol yields, will vary depending on several factors such as biomass type, pretreatment type, pretreatment conditions, and so forth.

Conventional methods used to convert biomass to sugars include processes employing, for example, a concentrated acid hydrolysis pretreatment, a two-stage acid hydrolysis pretreatment as well as processes employing any known conventional pretreatment, such as hydrothermal or chemical pretreatments, followed by an enzymatic hydrolysis (i.e., enzyme-catalyzed hydrolysis) or simultaneous enzymatic hydrolysis and saccharification. Such pretreatment methods can include, but are not limited to, steam explosion (StEx), dilute acid hydrolysis, high pressure hot water-based methods, i.e., hydrothermal treatments such as steam explosion and aqueous hot water extraction, reactor systems (e.g., batch, continuous flow, counter-flow, flow-through, and the like), AFEX™, ammonia recycled percolation (ARP), lime treatment and a pH-based treatment.

Several of these methods generate nearly complete hydrolysis of the hemicellulose fraction to efficiently recover high yields of the soluble pentose sugars. This also facilitates the physical removal of the surrounding hemicellulose and lignin, thus exposing the cellulose to later processing. However, each method has its drawbacks. For example, with StEx, although the liquid stream generated by StEx is composed of a relatively high sugar concentration that could potentially be fermented, the presence of inhibitory compounds, e.g., furans, requires detoxification and nutrient supplementation to be effective for ethanol production. In a StEx process, loose biomass is typically soaked in water for several hours (e.g., overnight) and then dewatered to approximately 65% moisture. The dewatered biomass is added into a pressure reactor, where steam at 10-40 bars can be injected to increase the temperature of the biomass to between 180 and 250° C. The biomass is allowed to contact the steam at a specific temperature for a period of about 5 to about 15 min. Once the residence time is achieved, the discharge valve is opened causing an explosive depressurization inside the reactor. During this process, the biomass and a liquor generated during pretreatment, i.e., the whole slurry, can be discharged to a blow tank. The liquor can then be separated from the solid biomass using a press and the solids can be used for enzymatic hydrolysis.

Furthermore, most, if not all, pretreatment approaches do not adequately hydrolyze the cellulose fraction of biomass. See, for example, U.S. patent application Ser. No. 13/642,052 (hereinafter the "'052 Application"), assigned to the Assignee, which is hereby incorporated by reference in its entirety, and describes cellulose in detail, including the different crystalline structures of cellulose, which typically correspond to the location of hydrogen bonds between and within strands. As stated in the '052 Application, natural cellulose is cellulose I, with structures $I_\alpha$ and $I_\beta$. Cellulose produced by bacteria and algae is enriched in $I_\alpha$ ($I_{alpha}$) while cellulose of higher plants consists mainly of $I_\beta$ ($I_{beta}$). Cellulose I is irreversibly converted to cellulose II by treatment with aqueous NaOH or by using ionic liquids. Cellulose $III_I$ can be generated from cellulose I when treated using ammonia or amines under specific conditions, as described for loose biomass in the '052 Application, and, surprisingly, as described herein, for untreated or conventionally pretreated densified biomass. Additionally, cellulose $III_{II}$ is generated from cellulose II. As referred to herein, the phrase "cellulose III" is intended to refer to "cellulose $III_I$." Cellulose IV is generally made by heating cellulose III in and appropriate solvent (e.g., glycerol). The X-ray diffraction 2θ angles for cellulose I is 14.6, 16.4 and 22.6; for cellulose III, 11.7 and 20.6, and for cellulose IV, 15.5 and 22.4. Cellulose I is converted in to amorphous cellulose when treated with phosphoric acid. (See FIGS. 1A-1D, which are schematic illustrations and graphs showing different allomorphs of cellulose, how the allomorphs can be generated and certain of their properties including A) conditions at which different allomorphs of cellulose are formed B) three different allomorph of cellulose conversion when using commercial enzymes, C) enzyme binding patterns for Cellulose I and cellulose II and D) an X-Ray diffraction pattern for four different allomorphs of cellulose. See also, U.S. patent application Ser. No. 13/886,021, also assigned to the Assignee, which is hereby incorporated by reference in its entirety.

Cellulose III formation can be detected from its distinct X-ray diffraction pattern by disappearance of the peak at 22.6 degree 2θ accompanied by formation of a prominent peak at 20.6 and 12 degrees 2θ. Such an X-ray diffraction pattern is comparable to what has been reported in literature for cellulose III from cotton. Treatment of cellulose III with ammonium hydroxide (of varying concentrations) has also been reported to cause reversion to cellulose I. As the concentration of cellulose III increases to at least a majority (>50%), a new peak emerges as compared to cellulose I. Using deconvolution (fitting the XRD curve using curve fitting software), cellulose III and cellulose I content can be predicted. See, for example, Ciolacu, D. E., et. al., *Studies concerning the accessibility of different allomorphic forms of cellulose*, Cellulose, February 2012, DOI: 10.1007/s10570-011-9620-1, which is hereby incorporated herein by reference in its entirety. In various embodiments, the conversion of CI to CIII from a cellulosic sample is at least a majority (>50% by weight), such as at least 60%, at least 70%, at least 75%, at least 80%, at least 90%, up to substantially all (99%-99.9%), further including complete conversion. In other embodiments, the conversion is from about 50 to 100%, from about 50 to about 99.9%, from about 50 to about 99%, from about 50 to about 90%, further including from about 75% to substantially all or all, including any range there between.

As such, use of a conventional EA/cellulosic conversion pretreatment represents an improvement in this regard, as such a process can significantly hydrolyze the cellulose fraction of biomass, which can reduce downstream enzyme loading by up to 60% as compared to conventional ammonia pretreatments, including various AFEX™ pretreatment processes. However, conventional EA/cellulosic conversion pretreatments are limited to loose biomass and require ammonia to biomass loadings from at least 3:1 to about 8:1 in order to immerse loose biomass adequately to solubilize the lignin contained therein and effect a complete conversion of cellulose I to cellulose III. However, use of such large amounts of ammonia can result in high operating and energy costs, including not only the initial ammonia costs, but also the costs associated with recovering and reusing ammonia for subsequent cycles. Furthermore, most conventional EA/cellulosic conversion pretreatments also require elevated pressures since the pretreatment is carried out at elevated temperatures. Exemplary conventional EA/cellulosic conversion pretreatments include operating temperatures of at least 120° C. and pressures from about 1000 to about 2000 psi. Such conditions increase reactor costs since they must be sized to accommodate the reactor volume of the loose biomass and be configured to operate under elevated temperatures and pressures. While higher temperatures have been reported to speed up the de-esterification reactions, higher ammonia loading can promote the cleavage of ester linkages, as well as the conversion of cellulose CI into CIII increasing the biomass susceptibility to enzymatic attack.

While it may be possible to perform conventional EA/cellulosic conversion on loose biomass at lower temperatures, such as down to 25° C. or 22° C., and lower pressures, such as down to 120 psi, conventional EA/cellulosic conversion cannot be performed at lower pressures, let alone at atmospheric pressures. Furthermore, such conditions may or may not result in a majority of the cellulose I being converted to cellulose III. Furthermore, loose biomass requires higher ammonia to biomass loadings, such as at least 3:1 to obtain complete conversion, as noted above. While it was thought that a 2:1 ratio may possibly convert at least half of the cellulose I to cellulose III (as noted in the '052 Application), in practice, this is difficult to determine. The most that can be stated when the conversion is not complete, is that a peak at 22.6 degree 2θ in an X-ray diffraction pattern is still present for cellulose I. In some instances, it may be possible to express the degree of conversion in terms of the relative height of the peak at 20.6 degree 2θ and/or the peak at 12 degrees 2θ (which is indicative of cellulose III) versus the height of the peak at 22 degree 2θ (cellulose I). As such, at most, a degree of conversion in a conventional EA/cellulosic conversion pretreatment, when using an ammonia to biomass loading of 2:1, can be described as having a peak of 22.6 degree 2θ for cellulose I and a peak of 20.6 degree 2θ for cellulose III that is higher, such as two times higher.

In contrast, the novel densified cellulosic conversion pretreatments described herein, provide not only the downstream results noted above for conventional EA/cellulosic conversion pretreatments with respect to reduced enzyme loading (in embodiments in which hydrolysis is performed), but do so using less ammonia for the pretreatment process and providing a number of other downstream advantages, as noted herein. In practice, the various embodiments described herein may be referred to commercially as a "Compacted Biomass Ramping Ammonia" or "COBRA" pretreatment even in embodiments in which no actual "ramping" of temperature is taking place. Furthermore, it is to be understood that the term "compacted" when used as part of the term "Compacted Biomass Ramping Ammonia," is intended to refer specifically to densified biomass as defined herein (which retains its shape once pressure is released) and not to any type of "compacted biomass" as defined herein, which does not retain its shape.

In various embodiments described herein, densified cellulosic conversion pretreatments are provided in which at least a majority of the cellulose I in untreated densified biomass (or, in some embodiments, conventionally pretreated densified biomass containing cellulose I) is converted to cellulose III, with or without a subsequent lignin extraction step, and further with or without other steps as described herein. Use of densified biomass allows for much lower ammonia loadings (ammonia:biomass ratio) as compared to loose biomass, such as from less than 3:1 to about 0.5:1, such as less than 2:1 to about 1:1, such as from about 1:1 to about 0.5:1, such as from about 1:1 to about 0.8:1, such as no more than 2:1, no more than 1:1, no more than 0.8:1, no more than 0.6:1, no more than 0.5:1, no more than 0.4:1, no more than 0.3:1, and no more than 0.2:1, further including any range there between.

Densified biomass has a bulk density from about 50 to about 100 kg/m$^3$, which is about five to about 15 times higher than loose biomass, such as 8-12 times. As such, it was expected that at least as much ammonia, if not more, than the amount required to pretreat loose biomass would be required in order to convert at least a majority up to all of the cellulose I to cellulose III.

Furthermore, when loose biomass, such as from a compacted bale, is treated with 1:1 anhydrous ammonia to biomass loading, pretreatment is not efficient. The liquid to solid ratio is very low, such that not all of the surface area of each fiber is in direct contact with the ammonia. Thus, while the fibers of the biomass having contact with the ammonia may be efficiently pretreated, and even lead to conversion of some cellulose I to cellulose III, the fibers not in direct contact with the ammonia are only partially pretreated such that none of the cellulose I is converted to cellulose III. See, for example, FIG. 11 which shows peaks at both cellulose I and cellulose III.

Those skilled in the art, understanding the above results with loose biomass and knowing that the exposed surface area for each particulate is even lower than the exposed surface area of each fiber of loose biomass would not expect to achieve any better results with such a low ammonia loading for densified biomass particulates.

Surprisingly, however, the inventors are the first to determine that densified biomass can not only be successfully pretreated to convert at least a majority of cellulose I to cellulose III, it can be done at lower ammonia loadings as compared with conventional EA/cellulosic conversion pretreatment processes which utilize loose biomass.

Figure 2A:
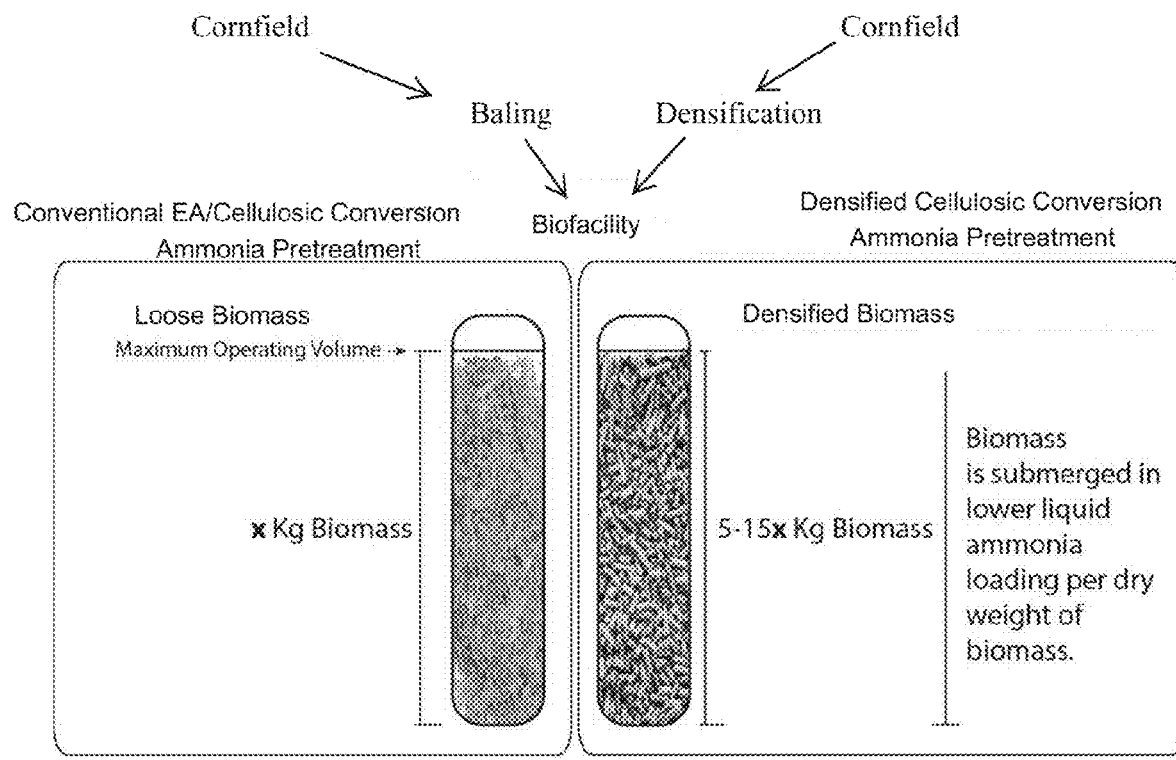
FIG. 2A is a schematic illustration showing a comparison of a conventional extractive ammonia (EA)/cellulosic conversion pretreatment process (hereinafter "conventional EA" pretreatment) using loose biomass with a densified cellulosic conversion pretreatment process according to an embodiment.

FIG. 2A is a schematic illustration showing a comparison of a conventional extractive ammonia (EA)/cellulosic conversion pretreatment with a densified cellulosic conversion pretreatment. This diagram illustrates the steps performed from the field to a conventional EA/cellulosic conversion biofacility as compared to one embodiment of the densified cellulosic conversion pretreatment biofacility described herein. As can be seen, from about 5 to about 15 times more biomass can be treated in a densified cellulosic conversion pretreatment with a given amount of ammonia as compared to a conventional EA/cellulosic conversion pretreatment.

Figure 2B:
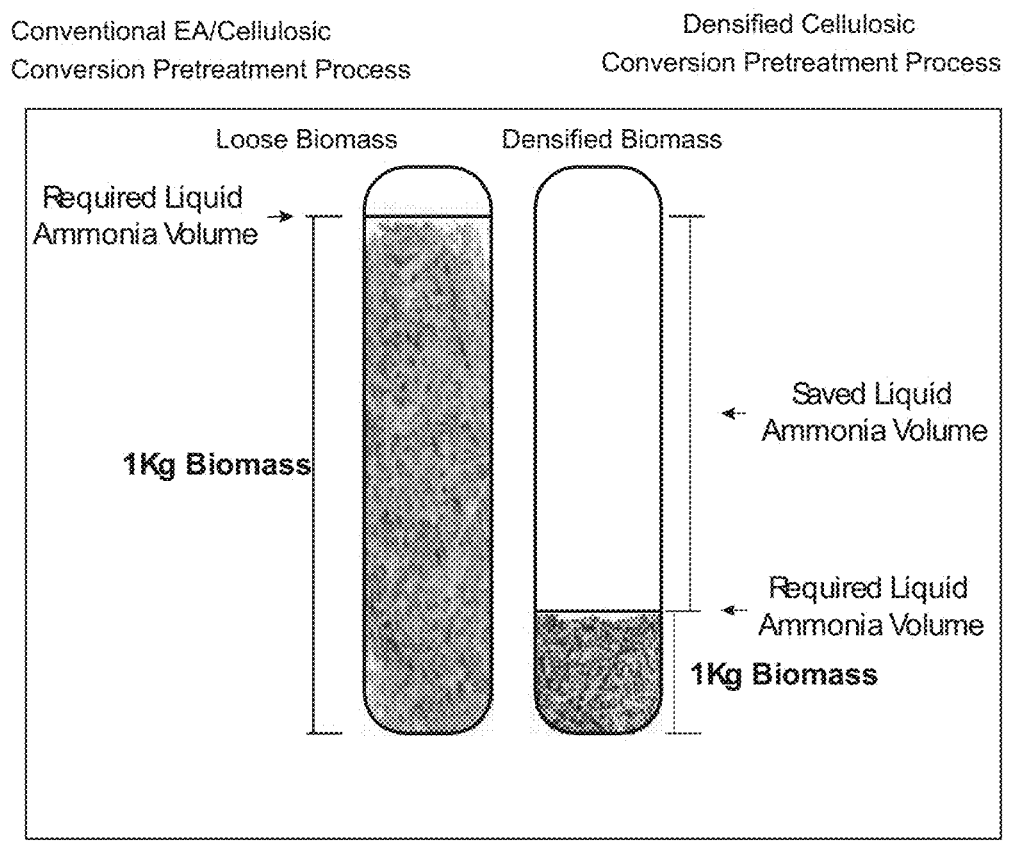
FIG. 2B is a schematic illustration showing the reduced ammonia usage with a densified cellulosic conversion pretreatment process as compared with a conventional EA/cellulosic conversion pretreatment process according to an embodiment.

FIG. 2B is a schematic illustration showing the ammonia savings with a densified cellulosic conversion pretreatment as compared with a conventional EA/cellulosic conversion pretreatment. FIG. 2B shows the difference in space taken up in a reactor between a given amount of loose biomass and the same amount of densified biomass. Such difference again, can be on the order of 5 to 15 times, which leads to a reduction in the amount of ammonia required in an a densified cellulosic conversion pretreatment to achieve the desired results as compared to a conventional EA/cellulosic conversion pretreatment.

In the various embodiments described herein, the cellulosic or lignocellulosic biomass can be densified using any suitable densification process, including, for example, established techniques (mechanical densification technology or agglomeration), which may include the methods described in Thumuluru et. al., 2011 if the resulting product is sufficiently densified as defined herein. Such methods can also include U.S. Pat. Nos. 8,673,031 and 9,039,792, which issued on Mar. 18, 2014 and May 26, 2015, respectively, to Assignee and/or U.S. application Ser. No. 13/835,382 entitled Densified Biomass Products Containing Pretreated Biomass Fibers, also assigned to Assignee (hereinafter referred to as "MSU Densification Technology"), all of which are incorporated by reference herein in their entireties, although the invention is not so limited.

Such densification can include a first step to reduce the particle size of the native loose biomass, which results in fibers having a reduced space there between, as compared to the native biomass. In one embodiment, the particle size of loose biomass is reduced, such as with the novel methods described in U.S. patent application Ser. No. 14/382,370, entitled "Methods for Increasing Sugar Yield with Size-Adjusted Lignocellulosic Biomass Particles," assigned to Assignee, which is incorporated herein by reference in its entirety. In one embodiment, the particles are size adjusted according to conventional methods. In one embodiment, the particle size of the loose biomass is not reduced prior to densification.

Subsequently, when moistened, such as with steam or water, the size-reduced particles become softened, i.e., conditioned, with a moisture content (mwb) from about 20% to about 40%. In addition, as discussed in the MSU Densification Technology, protein, lignin and extractives present in lignocellulosic biomass fibers can act as natural binding agents to keep individual fibers stuck together when densified, such as with extrusion or compression to produce densified biomass particulates. In other embodiments, other densification methods are used that may require a binder.

The densified biomass can optionally be cured by drying, such as in a heated oven to reduce the moisture content (mwb) to less than 10%. Furthermore, an optional drying step can be used to help preserve the biomass for a long period of time (e.g., months) against microbial degradation. Such preservation helps to maintain integrity of the densified biomass particulate during transportation and storage. However, due to the action of natural or external binders that occupy the spaces between fibers and adhere the various fibers to each other to maintain their form or shape, densified particulates do not inherently begin reverting to their original configuration once the external compaction forces are released, nor change their form or shape unless subjected to external forces.

Such densified biomass can then be safely stored on the farmer's property in any suitable container or storage facility, including sack bags, at the centralized densifying facility, or in existing private and/or commercial grain silos and provided to the facility on demand. In some embodiments, the densified biomass is transported directly to the biofacility and stored on site. This is in contrast to conventional methods, in which biomass is first processed, i.e., size-reduced, prior to densification, whether it be on site or elsewhere.

In one embodiment, native (non size-reduced) loose biomass is conditioned. In one embodiment, sized-reduced loose biomass is conditioned as described above.

In one embodiment, native loose biomass which has been conditioned is densified as defined herein. In on embodiment native loose biomass which has not been conditioned is densified. In one embodiment, size-reduced loose biomass that has been conditioned is densified. In one embodiment, size-reduced loose biomass that has not been conditioned is densified.

In one embodiment, native loose biomass which has been conditioned and densified is dried. In one embodiment, native loose biomass which has not been conditioned, but subject to densification is not dried. In one embodiment native loose biomass which has not been conditioned and densified is dried. In one embodiment, native loose biomass which has not been conditioned, but subject to densification is not dried. In one embodiment, size-reduced loose biomass that has been conditioned and densified is dried. In one embodiment, size reduced loose biomass that has been conditioned and subject to densification is not dried. In one embodiment, size-reduced loose biomass that has not been conditioned, but subject to densification is dried. In one embodiment, size-reduced loose biomass that has not been conditioned, but subject to densification is not dried.

Figure 2C:
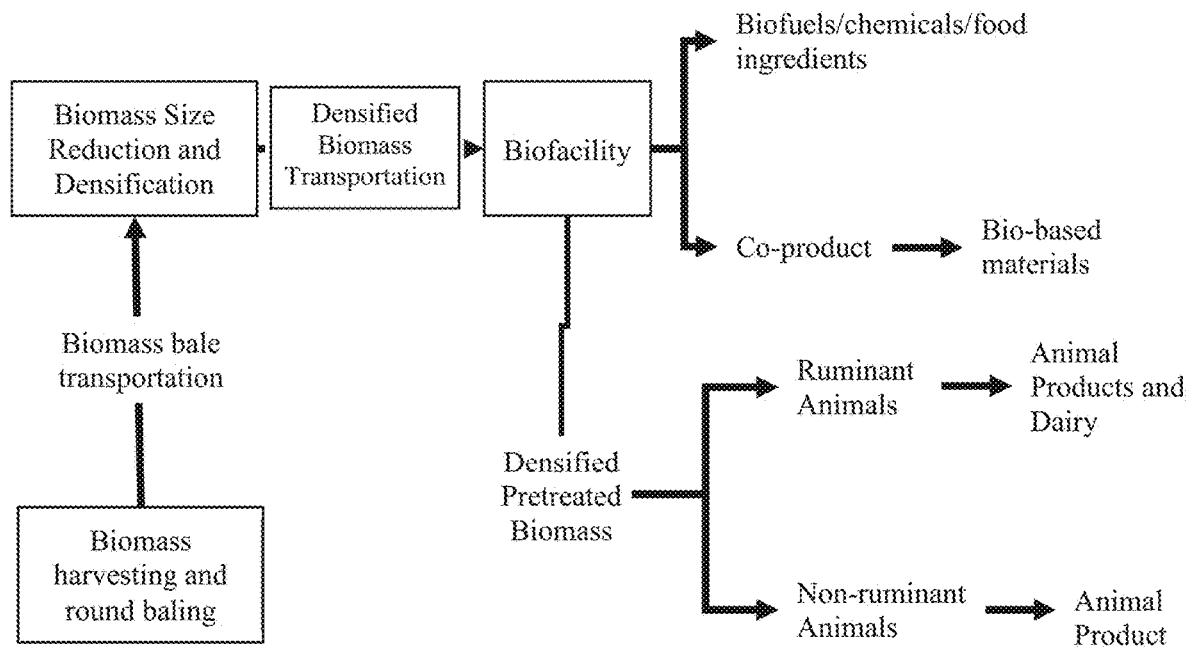
FIG. 2C is a schematic illustration of biomass and logistics transportation for a densified cellulosic conversion pretreatment according to an embodiment.

In the decentralized processing shown in FIG. 2C, biomass can be harvested using conventional procedures and then baled and transported to a biomass densification facility. In other embodiments, the biomass can be baled and densified or simply densified on site using any known densification methods. In one embodiment, the densification facility performs three processing steps, namely, 1) biomass size reduction, 2) biomass conditioning and 3) biomass densification, as shown in FIG. 2C. Thereafter the densified biomass can be transported to a biofacility which performs the densified cellulosic conversion pretreatment to produce pretreated/CIII-densified biomass. In various embodiments, the pretreated/CIII-densified biomass can be used as a biofuel, chemical or feed ingredients. In embodiments in which lignocellulosic biomass is used, lignin (and other plant cell wall components) can be extracted as a co-product and used in any bio-based materials industry. Additionally or alternatively, the pretreated/CIII-densified biomass can be redensified for use as feed for ruminant and non-ruminant animals to produce dairy products and animal products, respectively.

In one embodiment, a centralized processing scenario is used. In this embodiment, the biomass is both densified and pretreated using the densified cellulosic conversion pretreatment process at the same location.

In embodiments in which lignocellulosic biomass is used, more homogeneous high molecular weight lignin is obtained, as compared to a conventional pulping process, due to the fact that ammonia cleaves ester linkages, not ether linkages, during pretreatment. Unlike other lignin extraction processes (where the catalyst is solubilized along with lignin and thus relies on expensive processing steps to recover the catalyst), ammonia is a volatile alkali that can be easily recovered. In one embodiment, more than about 97% of the ammonia is recovered with the remaining approximately 3% having reacted with cell wall components. This ammonia can be re-used during subsequent pretreatments, thus leaving behind a relatively clean lignin stream.

Use of densified biomass also provides benefits at the front end as compared with conventional pretreatment methods of all kinds which rely on biomass harvested from a field and formed into compressed round or compressed rectangular-shaped bales. Such bales occupy significant volume, with flatbed trucks capable of transporting only about 20 to 40 bales in each load. Such loads are typically transported several miles (e.g., 5 to 60 miles or more) to one of multiple area storage sites, each containing hundreds to thousands of such bales in a given county, and is then transported again when needed at the biofacility, which can be a distance of several miles, such as 5 to 30 miles or more. As such, more truck loads are required to transport a given amount of loose biomass as compared to densified biomass, which significantly increases the cost of biomass that is delivered at the biofacility.

Furthermore, each time bales are moved, their integrity is reduced, with an increasing number falling apart each time. Additionally, as bales sit in outdoor storage sites, they are exposed to the weather, even if tarps are used on the top bales. As such, the sun, wind and rain not only further degrade them with each passing month, reducing their integrity, the risk of fires is high due to lightning strikes and/or spontaneous combustion. Such fires are known to burn at high temperatures in excess of 5000 F and, to date, cannot be put out by any conventional means. Such fires are currently left to burn and smolder for days or weeks, producing significant amounts of ash and odor, thus creating health risks and causing property damages to nearby neighbors and communities. Bales covered on all sides with tarps in an attempt to reduce the effects of rain and wind effectively function as greenhouse environments, with the bales still degrading due to trapped moisture and exposure to heat from the sun, with the risk of fires due to spontaneous combustion and/or lightning still present. Additionally, microbes inherently present in the biomass can cause degradation. Exposure to microbial spores can pose a health hazard for workers in the biofacility processing the biomass.

In contrast, transportation of densified biomass not only avoids all of the aforementioned transportation and storage problems and associated costs, the densified biomass has the added benefit of being storable in existing infrastructure, such as grain silos. Densified biomass therefore requires less storage space and has a longer shelf life as compared to bales stored outside. In one embodiment, biomass is densified at one location, such as in a farmer's field or at a centralized densifying facility.

A plurality of densified biomass particulates of a given mass is known to have a bulk density about five to about 15 times higher than a given mass of loose biomass. This allows the given mass of densified biomass particulates to occupy a smaller volume as compared to loose biomass, thus allowing a lower volume of liquid ammonia to completely submerge the densified biomass, relative to loose biomass. As a result, a densified cellulosic conversion pretreatment can be carried out in smaller reactors as compared reactors used in a conventional EA/cellulosic conversion pretreatment which uses loose biomass. Use of a smaller reactor, in turn, allows for lower pressures and temperatures to be used, while still allowing for a majority up to all of the cellulose I to cellulose III.

Specifically, to be effectively pretreated, a given particulate of densified biomass must be in contact with ammonia throughout its interior (see, e.g., FIGS. 4 and 5), not just on the surface. In some embodiments, the ammonia can diffuse from the particulate surface to the particulate interior, such that the particulates swell and stick to each other without disintegrating. In some embodiments, at least some of the particulates can additionally or alternatively disintegrate as a function of pretreatment time. Such complete pretreatment requires not only a suitable ammonia to biomass loading, but also a suitable residence time, at a suitable temperature and pressure.

FIGS. 3A-3D are schematic illustrations showing A) a densified cellulosic conversion pretreatment with solvent, i.e., extractive densified cellulosic conversion pretreatment B) a densified cellulosic conversion pretreatment without solvent extraction, C) a densified cellulosic conversion pretreatment with a post pretreatment solvent extraction step, and D) a densified cellulosic conversion pretreatment with a post pretreatment lignin extraction step, i.e., densified cellulosic conversion-LE pretreatment. These and other embodiments will be discussed below.

In one embodiment, the biomass is cellulosic biomass. In one embodiment, the biomass is lignocellulosic biomass. In various embodiments, in which lignocellulosic biomass is used, an extractive solvent is added to the liquid ammonia in order to remove extractives. In one embodiment, lignocellulosic biomass is used and at least 40%, such as up to 50% of lignin and other extractives are extracted. Additionally or alternatively, in embodiments in which either cellulosic or lignocellulosic biomass is used, a hydrolysis step is also performed. Additionally or alternatively, in various embodiments, in which lignocellulosic biomass is used, a solvent extraction step is performed during or after pretreatment. In one embodiment, a lignin extraction step is additionally or alternatively performed post-pretreatment. In various embodiments, the post (densified cellulosic conversion process) lignin extraction step extracts an additional 0.5%, such as about 1%, about 2%, about 3%, up to about 4% additional lignin, by weight, beyond the lignin removed during the densified cellulosic conversion process. Various other process steps can also be performed, including, but not limited to, a redensification step of the pretreated/CIII-densified biomass to produce animal feed. In one embodiment, the process can include performing a densified cellulosic conversion pretreatment on conventionally pretreated densified biomass, such as conventional ammonia (e.g., AFEX™) or acid pretreated densified biomass, including StEx pretreated densified biomass, i.e., cellulose reactivation of conventionally pretreated densified biomass. In one embodiment, untreated densified biomass is subject to the densified cellulosic conversion process.

As noted above, lower pressures can be used as compared with conventional EA conversion processes using loose biomass and as compared with other conventional pretreatment processes discussed herein. In various embodiments, the pressure can range from about atmospheric pressure to about 150 psi, such as from about 150 to about 400 psi, or from about 200 to about 300 psi, including any range there between, further including no more than 150 psi and no greater than 400 psi. In one embodiment, the novel pretreatment process described herein is performed at temperatures from about 70 to 80° C. and a pressure of about 440 psi to 460 psi, including any range there between.

In various embodiments, lower temperatures can be used as compared with conventional EA conversion processes using loose biomass and as compared with other conventional pretreatment processes discussed herein. In various embodiments, the temperature can range from about 4 to about 140° C., such as about 18 to about 100° C., or from about 18 to about 70° C., or from about 25 to about 100° C., or from about 20 to about 28° C., including any range there between, further including a temperature of at least room temperature or a temperature of no more than 140° C. The appropriate temperatures and pressures can depend on the type of biomass being treated. In one embodiment, densified hardwoods are subject to a densified cellulosic conversion pretreatment, thus requiring higher temperatures and/or higher pressures, such as from about 70 to about 100° C. or up to about 400 psi. In one embodiment, conventionally pretreated densified biomass is subject to a densified cellulosic conversion pretreatment, thus requiring lower temperatures, such as from about 25 to less than 70° C., at atmospheric pressure (14.7 psi) or slightly higher, such as up to about 50 psi.

However, if desired, higher temperatures and pressures can optionally be used, such as greater than 450 psi up to about 1000 psi. In one embodiment, the pressure is greater than 400 psi, such as at least 500 psi, at least 600 psi, at least 700 psi, at least 800 psi, at least 850 psi, such as at least 1000 psi, such as from about 14.7 to about 850 psi, such as from about 14.7 to about 200 psi (including any range there between), further including pressures from 200 to about 450 psi, such as from about 1000 to about 2000 psi. Temperatures in excess of 140° C., such as greater than about 160° C. or higher can also be used. However, use of higher temperatures and/or pressures will increase the CAPEX due to higher pressure reactor requirement. Furthermore, IOEX-increased utility costs will be incurred with use of higher temperatures.

In one embodiment, the temperature is ramped up or down during the process at any suitable rate. Such ramping is likely to be used in embodiments at which the temperature is from about 18 to about 25° C.

In various embodiments, different residence times can be used. In one embodiment, residence times increases with increasing density of the densified biomass particulates. In various embodiments, residence times are from about 10 minutes to about 10 hours, such as from about 30 minutes to about 4 hours, such as from about 1 hour to about 6 hours, including any range there between. In other embodiments, the residence time may be lower than 30 minutes, such as no more than 15 minutes or no more than 10 minutes.

In one embodiment, the reaction is performed at a pressure greater than 400 psi with a reduced residence time, although costs may increase. Additionally, temperatures greater than 80° C. can be used with a reduced residence time, although costs may increase.

In various embodiments, the total moisture content (mwb) of the densified biomass and ammonia solution is at a level that still allows for a majority of cellulose I to be converted to cellulose III, including substantially all (99%-99.9%), up to all (100%) of the cellulose I converted to cellulose III. Depending on other conditions, including residence time, density of particulates, temperature and pressure, and moisture levels less than 30% a conversion of at least a majority (>50%) of cellulose I to cellulose III can be achieved. In one embodiment, the moisture level is less than 20% and substantially all up to all of the cellulose I is converted to cellulose III. In one embodiment, the moisture content (mwb) is less than 10% and substantially all up to all of the cellulose I is converted to cellulose III. In one embodiment, the total moisture content (mwb) is from about 1 to about 35%, such as from about 5 to about 25%, such as from about 5 to about 10%, including any range there between.

In one embodiment, liquid anhydrous ammonia is used and the biomass has a moisture content of less than 40% mwb, such as from about 1 to about 15% mwb, such as from about 5 to about 10% mwb, or any range there between. In one embodiment, liquid ammonia having a concentration no less than 80% is used and the biomass has a moisture content no greater than 10% mwb. In one embodiment, liquid anhydrous ammonia is used with densified biomass having a moisture content less than 10% mwb at a temperature of no more than about 25° C.

Figures 3A, 3B, 3C:
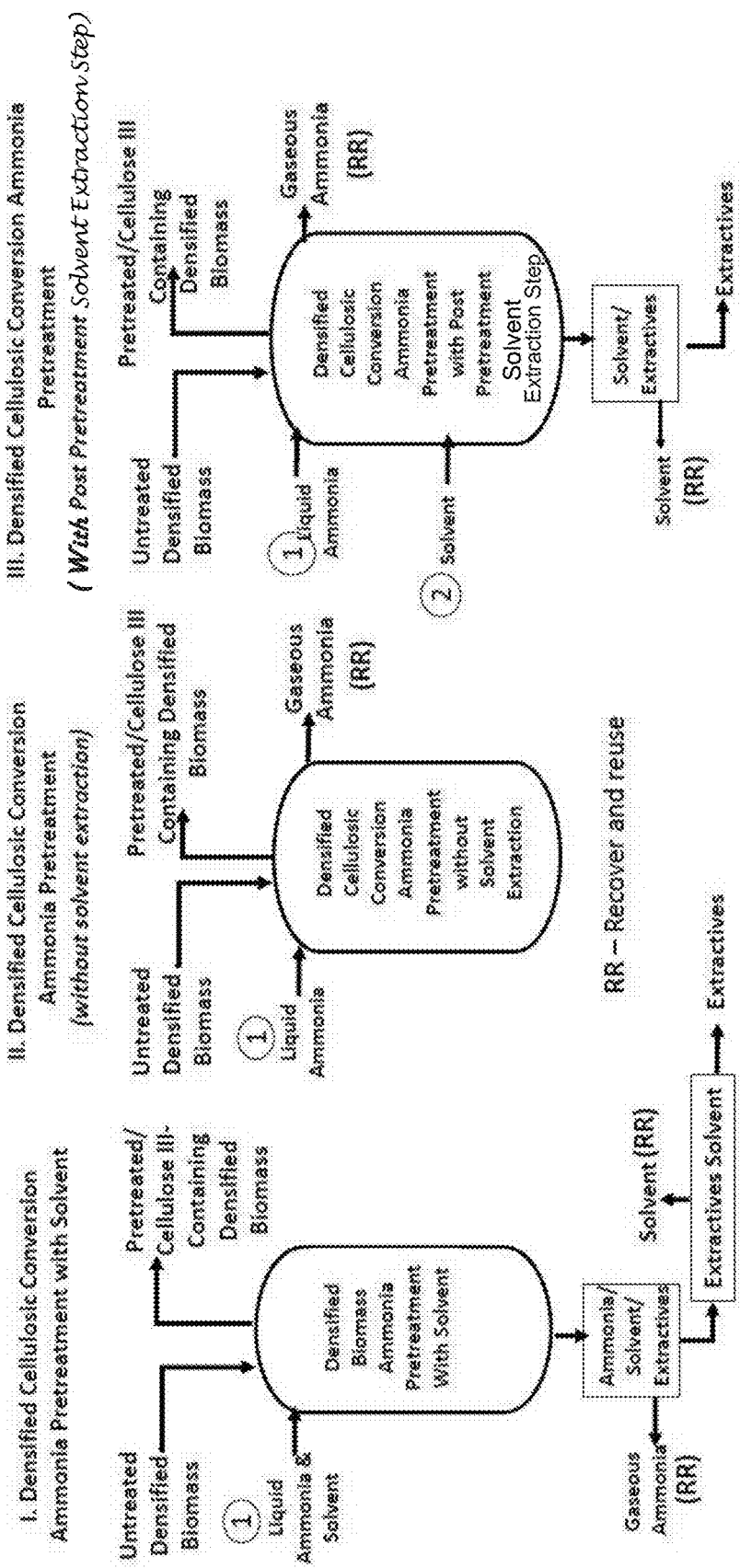
FIGS. 3A-3D are schematic illustrations showing A) a densified cellulosic conversion pretreatment with solvent i.e., extractive densified cellulosic conversion pretreatment, B) a densified cellulosic conversion pretreatment without solvent extraction, C) a densified cellulosic conversion pretreatment with a post pretreatment solvent extraction step, and D) a densified cellulosic conversion pretreatment with a post pretreatment lignin extraction step, i.e., densified cellulosic conversion-LE pretreatment, according to various embodiments.
Figure 3D:
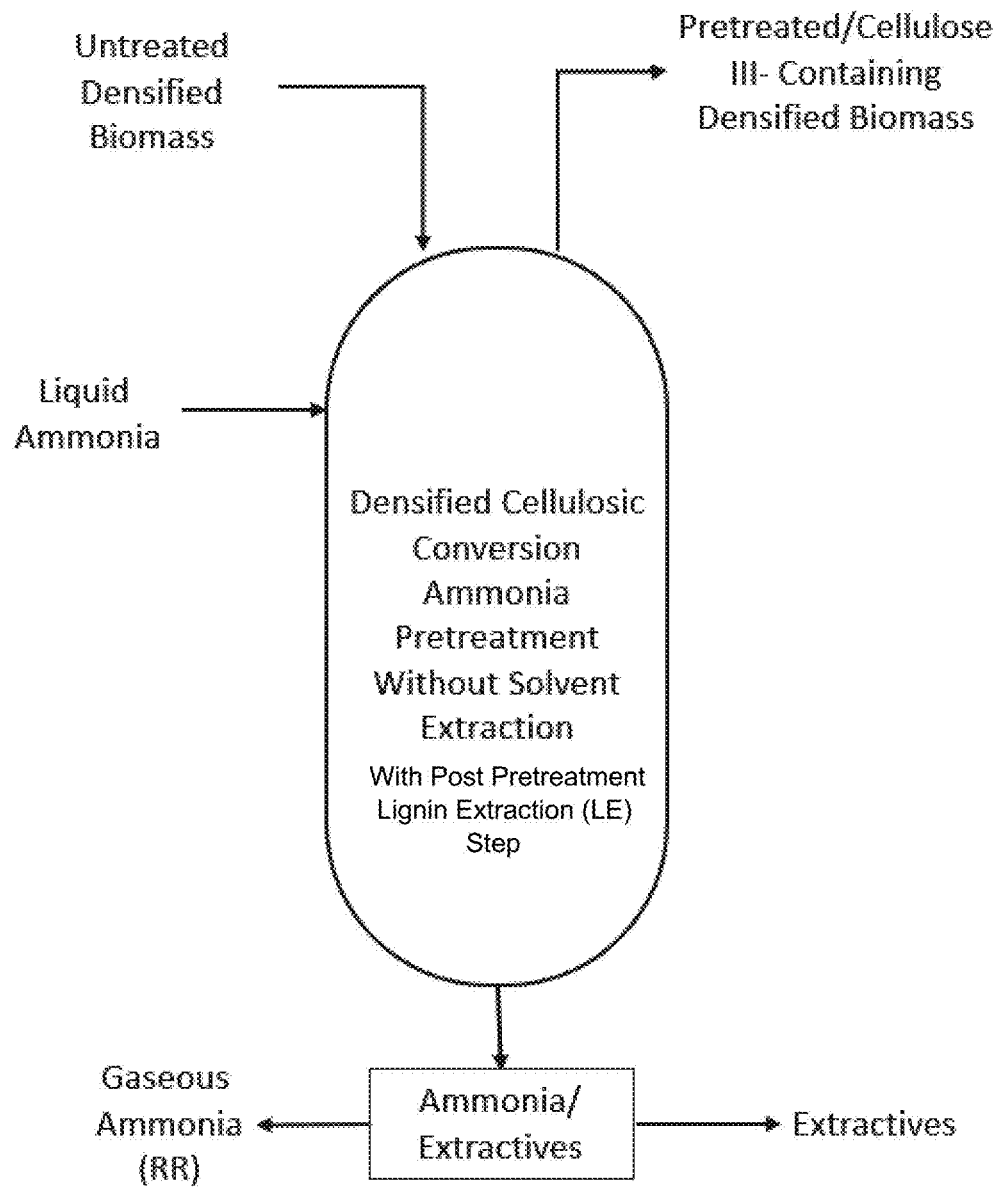

In one embodiment, the densified cellulosic conversion pretreatment is an extractive densified cellulosic conversion pretreatment which includes methods of extracting lignin and other plant cell wall extractives from untreated densified lignocellulosic biomass, such as pellets and briquettes (FIG. 3A).

Densified biomass which has not been pretreated is known to have reduced hydrolysable properties as compared with its pretreated counterparts. As such, the densified cellulosic conversion pretreatments described herein render the densified biomass more amenable to hydrolysis. Furthermore, as is understood by those skilled in the art, non-native cellulose III requires fewer enzymes during enzyme hydrolysis and at least two times more digestible than cellulose I. See also, U.S. patent application Ser. No. 13/886,021 (hereinafter the "021 Application"), which is hereby incorporated herein by reference in its entirety.

See, for example, Chundawat, S. P. S. et al., Restructuring the crystalline cellulose hydrogen bond network enhances its depolymerization rate. *Journal of American Chemical Society* 133 (29), 11163-11174 (2011); Chundawat, S. P. S. et al., Multifaceted characterization of cell wall decomposition products formed during ammonia fiber expansion (AFEX™) and dilute-acid based pretreatments. *Biores Technol* 101, 8429-8438 (2010); Chundawat, S. P. S. et al., Multi-scale visualization and characterization of plant cell wall deconstruction during thermochemical pretreatment. *Energy & Environmental Science* 4 (3), 973-984 (2011); and Chundawat, S. P. S. et al., Restructuring the crystalline cellulose hydrogen bond network enhances its de-polymerization rate. *Journal of American Chemical Society* 133 (29), 11163-11174 (2011), each of which is hereby incorporated by reference herein in its entirety.

In one embodiment, a hydrolysis step is performed on the pretreated/CIII densified biomass. Any suitable enzyme or enzyme combinations can be used in the hydrolysis. including those described in the following articles, http://www- .sciencedirect.com/science/article/pii/
S096800041630024X; http://www.sciencedirect.com/
science/article/pii/S1367593116301375; and http://
link.springer.com/article/10.1007/s00792-016-0893-z, all of
which are hereby incorporated by reference in their entireties. Those skilled in the art understand that certain enzymes hydrolyze cellulose and/or hemicellulose. In various embodiments, high temperature stable enzymes and/or high/low pH stable enzymes and/or multifunction enzymes are used. In one embodiment, the combination of enzymes comprises at least one exocellulase, at least one endocellulase and/or beta glucosidase.

Figure 13:
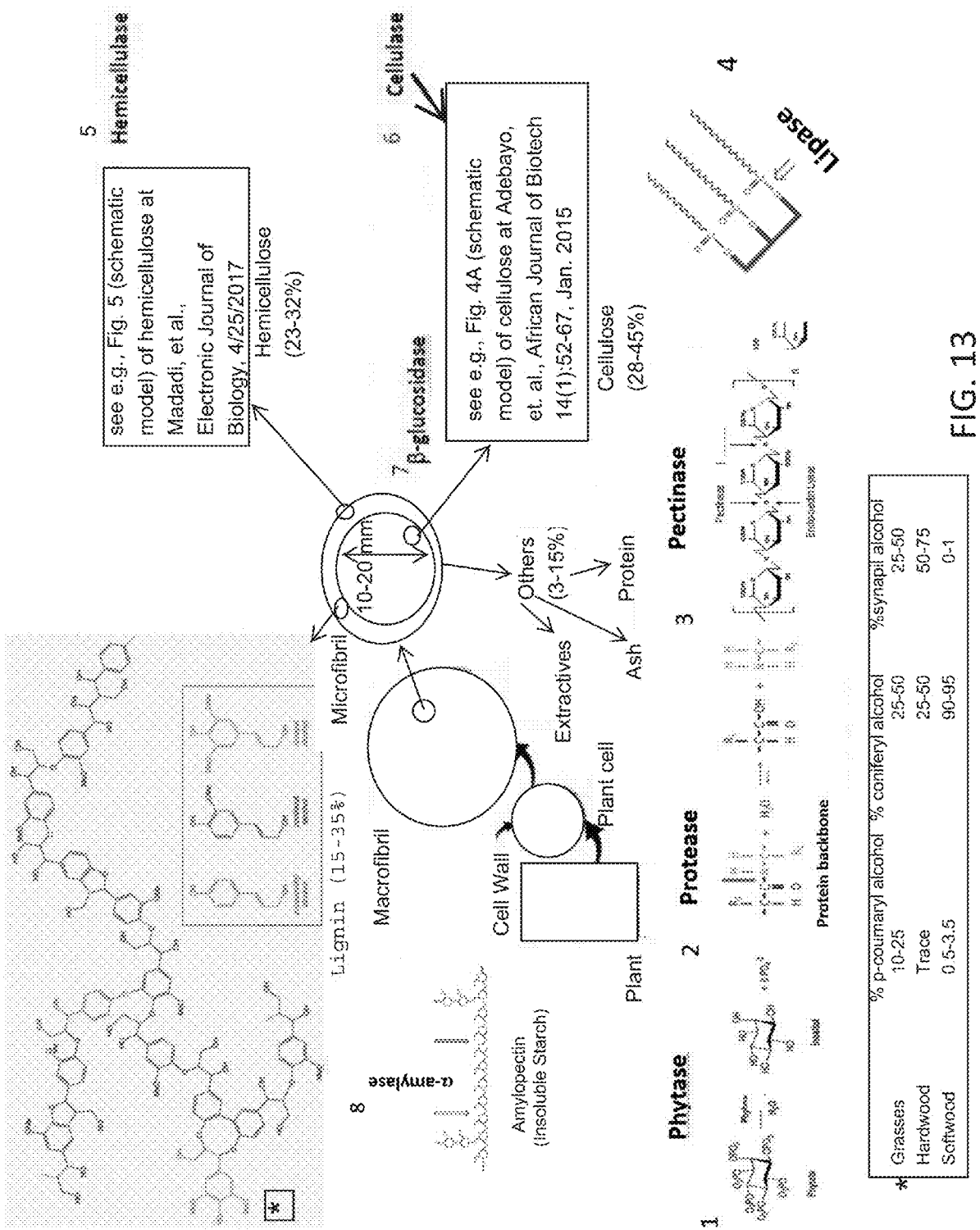
FIG. 13 is a schematic illustration showing plant cell wall composition and different enzymes acting on different components according to various embodiments.

Other digestive enzymes, such as the enzymes noted in FIG. 13 and Table 1 may also be used in embodiments in which animal feed is produced. In one embodiment, enzymes are added to the pretreated/CIII-densified biomass, and the product is subject to an additional densification step. The resulting animal feed is useful densified for improved digestion and to improve metabolizable energy. See, for example, FIG. 13 and Table 1.

TABLE 1

Digestive Enzymes and their benefits

| Enzyme | Substrate | Function |
| --- | --- | --- |
| Phytase | Phytate | Release phosphorous stored in phytate |
| Protease | Protein | Hydrolyze protein into smaller peptide/amino acid |
| Pectinase | Pectin | Break down indigestible pectin (reduce digestive viscosity) |
| Lipase | Lipids | Improve fat absorption |
| Sylanase | Xylan | Breaks down fiber |
| Cellulase | Cellulose | Breaks down fiber |
| β-gylcosidase | Cellobiose | Breaks down cellobiose to glucose |
| α-amylase | Starch | Improves starch digestibility |

| Total Benefits |
| --- |
| Improve feed conversion cropping and odor |
| Reduce feed cost |
| Use cheaper feeds |
| Greater uniformity |
| Reduce cost |
| Reduce phosphorous and nitrogen Excretion |
| Improve animal well-being (reduce mortality and need for antibiotic use) |

The resulting hydrolysis product can be obtained not only with lower ammonia loadings as compared to loose biomass, enzyme usage is reduced, as compared to conventional EA/cellulosic converted pretreated (loose) biomass. As such, in various embodiments, at least 7.5 mg/g of glucan is obtained. Additionally or alternatively, increased sugar conversion, such as at least 90% glucan and at least 70% xylan is also achieved. In other embodiments conversion of at least 91%, or at least 92%, or at least 93%, or at least 94%, or at least 95% glucan or higher can be achieved, such as from about 90 to about 97%, or from about 92 to about 96%, or from about 92 to about 93% glucan, including any range there between, and at least 75% or at least 80% conversion of xylan can be achieved. In embodiments in which an additional lignin extraction step is performed, an additional 1 to about 4% glucan can be obtained, such as at least 1%, at least 2%, at least 3% or at least 4%. In various embodiments additional xylan can also be obtained, such as an additional 0.5% to about 1% or more.

The novel densified cellulosic conversion pretreatment process and the densified cellulosic conversion-LE pretreatment process, can also reduce inhibitor products due to operating at less severe pretreatment conditions. In one embodiment, a fermentation step is performed and the reduced inhibitor products help avoid microbial inhibition during fermentation.

The various embodiments further include the following items:

1. A method of pretreating biomass comprising converting at least a majority of native cellulose $I_\beta$ to cellulose $III_I$ in densified biomass by pretreating the densified biomass with liquid ammonia, wherein the densified biomass is densified cellulosic biomass or densified lignocellulosic biomass and the liquid ammonia is anhydrous liquid ammonia or liquid ammonia comprising a solution of at least 80% ammonia, wherein the pretreating is performed at a temperature from about 4° C. to about 140° C. and at pressure from about 14.7 to about 200 psi to generate pretreated/CIII-densified biomass, wherein total moisture content of the densified biomass and the solution is 30% or less and a weight ratio of liquid ammonia to the densified biomass, is from about 0.3:1 to about 2:1, such as from about 0.5:1 to about 2:1.

2. The method of item 1 wherein the total moisture content (mwb) of the densified biomass and the solution is 20% or less and substantially all of the cellulose I is converted to cellulose III.

3. The method of claim 1 wherein the total moisture content (mwb) of the densified biomass and the solution is 10% or less and all of the cellulose I is converted to cellulose III and/or wherein the method further comprises a lignin extraction step following the converting step to convert additional glucan, such as an additional 1% to 4% by weight of glucan.

4. The method of item 1, wherein the densified biomass is densified cellulosic biomass and the pretreated/CIII densified biomass is pretreated/CIII densified cellulosic biomass or wherein the densified biomass is densified lignocellulosic biomass and the pretreated/CIII densified biomass is pretreated/CIII lignocellulosic densified biomass or pretreated-LE/cellulose III-containing densified biomass.

5. The method of item 4, wherein the densified lignocellulosic biomass is selected from corn stover, poplar, switchgrass, sugarcane bagasse, wheat straw, sorghum, energy cane, miscanthus, brewery spent grains, DDGS, soybean meal, and combinations thereof. Densified or non-densified CLM can also be used as the biomass.

6. The method of item any one of items 1 to 5, wherein the densified biomass is pretreated with the liquid ammonia for a period of time from about 10 minutes to about 10 hours, such as from about 30 minutes to about 10 hours.

7. The method of item 6, wherein the pretreatment is from about 1 to about 8 hours.

8. The method of item 6, wherein the temperature is from about 50° C. to about 120° C.

9. The method of item 6 wherein the weight ratio is from about 0.3:1 to about 1.2:1.

10. The method of item 6 wherein the densified biomass is untreated densified biomass or pretreated densified biomass containing no cellulose III.

11. The method of item 11 wherein the pretreated densified biomass is pretreated using a pretreatment selected from ammonia (such as AFEX™), dilute acid, concentrated acid, steam explosion, alkali (such as NaOH, KOH, CaOH, and the like), organosolv, ionic liquid, biological, tetrahydrofuran (THF) and combinations thereof.

12. The method of item 6, further comprising recycling the liquid ammonia in a batch mode, a semi-batch mode or continuously.

13. The method of item 6 wherein the pretreated/CIII densified biomass is redensified to produce animal feed with or without added digestive enzymes.

14. The method of item 6 further comprising an enzymatic hydrolysis step to hydrolyze the pretreated/CIII densified biomass product, wherein said enzymatic hydrolysis step proceeds at a rate that is at least 1.5 times faster than a hydrolysis step performed using densified biomass that has not been pretreated with the liquid ammonia.

15. The method of item 6, wherein the densified biomass is densified lignocellulosic biomass and the solution includes an organic solvent, wherein extractives present in the densified lignocellulosic biomass are removed during the liquid ammonia pretreatment.

16. The method of item 6, wherein the pretreated/CIII densified biomass is pretreated/CIII lignocellulosic densified biomass containing lignin and/or hemicellulose, and the method further comprises extracting at least a portion of the lignin and/or hemicellulose from the pretreated/CIII lignocellulosic densified biomass to produce an extracted product containing cellulose III and a pretreated densified biomass product, wherein said extracted product contains the lignin and/or hemicellulose.

17. The item of claim 16, wherein glucan and/or xylan is partially or wholly retained with the pretreated densified biomass product.

18. The method of item 15 or 16, wherein the solvent is water or an organic solvent.

19. The method of item 18, wherein the organic solvent is selected from acetone, ethanol, methanol, isopropanol, dichloromethane, methyl acetate, ethyl acetate, chloroform and combinations thereof.

20. The method of item 19, further comprising recycling the solvent in a batch mode, a semi-batch mode or continuously.

21. The method of item 16, wherein the lignin is one of a plurality of plant cell wall components which are extracted in the extracting step.

22. The method of item 21, wherein said plant cell wall components further include hemicellulose, arabinan, and combinations and degradation products thereof.

23. The method of item 19 wherein the pretreated/CIII densified biomass is redensified to produce animal feed with or without added digestive enzymes.

24. The method of item 6 further comprising a lignin extraction (LE) step.

24. A system comprising a reactor for converting at least a majority of native cellulose I to cellulose III in densified biomass by pretreating the densified biomass with liquid ammonia, wherein the densified biomass is densified cellulosic biomass or densified lignocellulosic biomass and the liquid ammonia is anhydrous liquid ammonia or liquid ammonia comprising a solution of at least 80% ammonia, wherein the pretreating is performed at a temperature from about 4° C. to about 140° C. and at a pressure from about 14.7 to about 200 psi to generate pretreated/CIII densified biomass, wherein total moisture content of the densified biomass and the solution is 30% or less and a weight ratio of liquid ammonia to the densified biomass, is from about 0.3:1 to about 2:1, such as from about 0.5:1 to about 2:1, and any suitable system controller or controllers known in the art for controlling the various parameters are connected to the reactor.

25. The system of item 24 further comprising a hydrolyzing tank.

26. The system of item 24 or 25 wherein the reactor is also an extraction vessel.

It is to be understood that the subject matter of each the method items listed herein is fully applicable to the system items listed herein, including, but not limited to, the additional lignin extraction (LE) step, which converts an additional 1% to about 4% additional glucan (by weight) of glucan, such as at least 1% additional glucan, at least 2% additional glucan, at least 3% additional glucan, such as at least 4% additional glucan. In various embodiments, an additional amount of xylan is converted as well.

The various embodiments will be further described by reference to the following examples, which are offered to further illustrate various embodiments. It should be understood, however, that many variations and modifications may be made while remaining within the scope of the various embodiments.

EXAMPLE 1

Materials and Methods

Poplar wood (P) from mature polar trees and corn stover (CS) were harvested from Idaho National Laboratories, were dried to a total moisture content (mwb) of approximately 15% and milled to 40 mesh particle size using a Wiley mill. The milled biomass was stored at 4° C. before being used in densification experiments. These materials were densified into pellets using a Buskirk Engineering PM800 pellet mill.

Moisture content was measured by an A&D moisture analyzer and raised to approximately 30% by adding deionized water before adding the milled biomass to the pelletizer. The sized reduced biomass was then fed to the pellet mill. Temperatures within the mill rose rapidly to as high as 150° C. due to heat dissipation generated by friction between the biomass, the rollers and the pellet dye. The densified biomass exiting the mill had a total moisture content (mwb) of about 15 to 20%. Thereafter, the densified biomass was annealed in an electrical oven set to 50° C. overnight to reduce the total moisture content to less than 8% (mwb).

Approximately 44.4 g of each material were pretreated with liquid anhydrous ammonia (source, 99.99%) in an 800 ML cylindrical make/model reactor custom designed at Michigan State University (See Sousa Article). In each instance, the reaction was allowed to proceed at ambient temperatures (25° C.) for 30 minutes, ramped to 70° C. and allowed to react for another 6 hours, after which the pressure was released. Biomass to ammonia loadings were varied from 0:1 to 1:1 in increments of 0.25, with testing for each loading carried out in triplicate. The pretreated materials were allowed to dry in a fume hood for approximately 24 hours. A mortar and pestle was used on the pretreated materials to ensure homogeneity for later testing. Table 2 shows the pretreatment conditions used. The materials were then extracted at 100° C. and 1500 psi in a DIONEX ASE 200 Accelerated Solvent Extractor with 95% ethanol.

TABLE 2

Pretreatment Conditions for Corn Stover (CS) and Poplar (P)
Pretreatment Condition

| Sample | Material | $NH_3$:BM | Pretreatment |
|---|---|---|---|
| 1 | CS | 0.1:1 | Densified Cellulosic Conversion Pretreatment |
| 2 | CS | 0.25:1 | Densified Cellulosic Conversion Pretreatment |
| 3 | CS | 0.5:1 | Densified Cellulosic Conversion Pretreatment |
| 4 | CS | 0.75:1 | Densified Cellulosic Conversion Pretreatment |
| 5 | CS | 1:1 | Densified Cellulosic Conversion Pretreatment |
| 6 | P | 0:1 | Densified Cellulosic Conversion Pretreatment |
| 7 | P | 0.25:1 | Densified Cellulosic Conversion Pretreatment |
| 8 | P | 0.5:1 | Densified Cellulosic Conversion Pretreatment |
| 9 | P | 0.75:1 | Densified Cellulosic Conversion Pretreatment |
| 10 | P | 1:1 | Densified Cellulosic Conversion Pretreatment |
| 11 | CS | 1:1 | AFEX™ (loose biomass) |

Figures 4A, 4B, 4C, 4D, 4E, 4F:
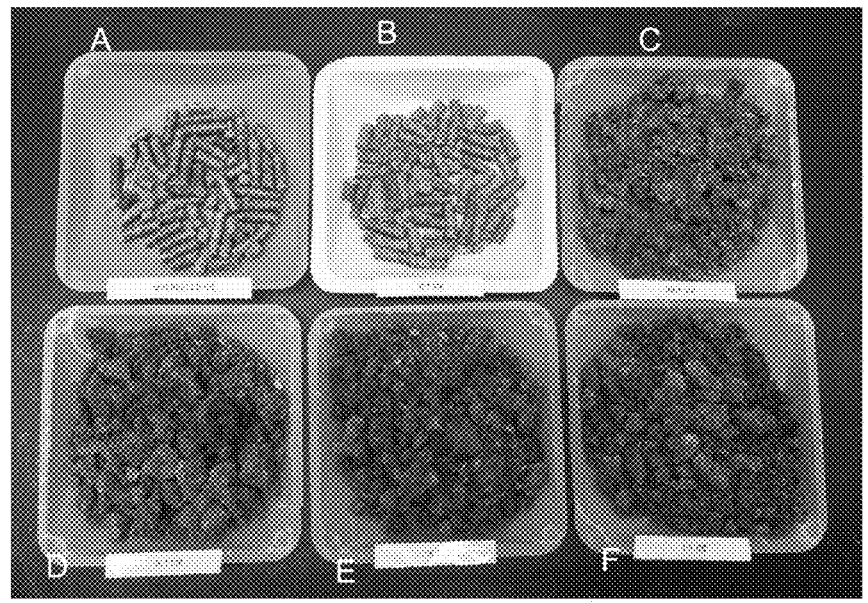
FIGS. 4A-4F are images of A) untreated densified corn stover particulates and pretreated/CIII-densified corn stover particulates at an ammonia to corn stover ratio of B) 0.1:1, C) 0.25:1, D) 0.5:1, E) 0.75:1 and F) 1:1 according to various embodiments.
Figures 5A, 5B, 5C, 5D, 5E, 5F:
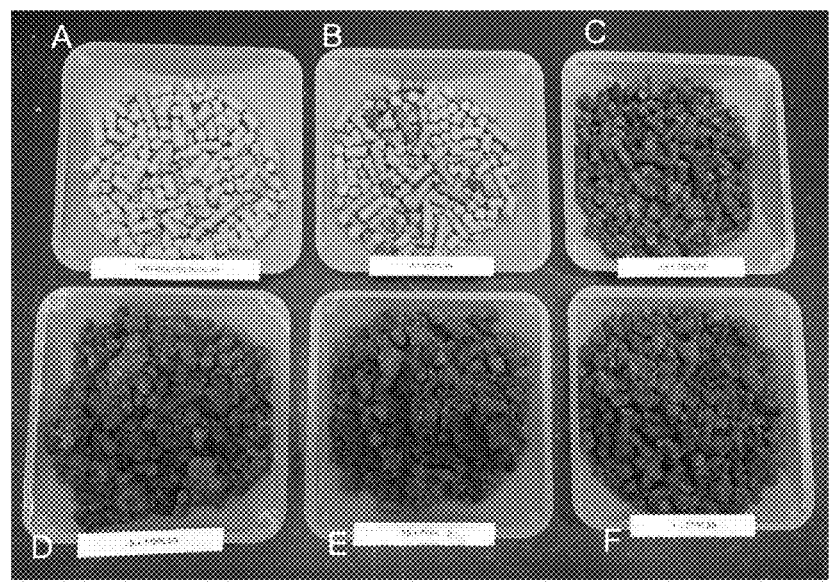
FIGS. 5A-5F are images of A) untreated densified poplar particulates and pretreated/CIII-densified poplar particulates at an ammonia to poplar ratio of B) 0.1:1, C) 0.25:1, D) 0.5:1, E) 0.75:1 and F) 1:1 according to various embodiments.

FIGS. 4 and 5 are photographs of various types of pretreated/CIII-densified biomass, including after a post-pretreatment extraction step according to the methods described herein. These figures show that the pretreated/CIII-densified biomass loosened up after the densified cellulosic-conversion pretreatment. It is clear that the density of the densified biomass changes over pretreatment time, but the liquid ammonia distribution within the densified biomass particulate has not been determined.

FIG. 4 are images of A) untreated densified corn stover particulates and pretreated/CIII-densified corn stover particulates at an ammonia to corn stover ratio of B) 0.1:1, C) 0.25:1, D) 0.5:1, E) 0.75:1 and F) 1:1.

FIG. 5 are images of A) untreated densified poplar particulates and pretreated/CIII-densified poplar particulates at an ammonia to poplar ratio of B) 0.1:1, C) 0.25:1, D) 0.5:1, E) 0.75:1 and F) 1:1.

In the case of samples which were subjected to extraction using ethanol (99.9% purity, Sigma-Aldrich), the samples were allowed to dry for 24 hours at ambient temperatures to allow the ethanol to evaporate. The weight and total moisture content of each sample was measured before extraction and after drying to construct a mass balance. The composition of the extracted materials was determined, and used to design the EH experiment.

After the composition was known, enzymatic hydrolysis was performed at 1% glucan loading in a total reaction volume of 10 ml. A cocktail of enzymes comprising "Second Generation" (2012-2014) NOVOZYMES enzymes, namely Cellic® "CTEC-2" (cellulase cocktail) and "HTEC-2" (hemicellulase cocktail) were loaded at a rate of 15 mg of enzyme per gram of glucan to the pretreated biomass in aqueous media. The reaction mixtures were then incubated at 250 rpm and 50° C. and sampled after 24 hours. The samples were then analyzed using a Shimadzu LC 2010 HPLC. This enzymatic hydrolysis procedure allowed the carbohydrate polymers to degrade to monomeric glucose and xylose, which were soluble in the water. Besides the water soluble sugars, this reaction resulted in unhydrolyzed solids, which were mostly composed by lignin and some unhydrolyzed cellulose/hemicellulose.

Table 3 shows the resulting pretreatment mass balance. Table 4 shows the resulting extraction mass balance when using ethanol. As can be seen, the lignin loss appears to correlate with ammonia loading.

TABLE 3

Pretreatment Mass Balance
Pretreatment Mass Balance

| Sample | Dry Mass In (g) | Dry Mass Out (g) | MC In % | MC Out % | Closure |
|---|---|---|---|---|---|
| 1 | 40 | 39.15 | 10 | 6.35% | 2.14% |
| 2 | 40 | 38.8 | 10 | 7.39% | 2.99% |
| 3 | 40 | 38.85 | 10 | 8.58% | 2.87% |
| 4 | 40 | 38.72 | 10 | 7.38% | 3.21% |
| 5 | 40 | 38.88 | 10 | 8.30% | 2.80% |
| 6 | 40 | 39.44 | 10 | 6.10% | 1.40% |
| 7 | 40 | 39.28 | 10 | 9.08% | 1.81% |
| 8 | 40 | 37.74 | 10 | 10.56% | 5.64% |
| 9 | 40 | 38.21 | 10 | 10.09% | 4.47% |
| 10 | 40 | 38.98 | 10 | 8.72% | 2.56% |
| 11 | N/A | N/A | N/A | 6.77% | N/A |

TABLE 4

Extraction Mass Balance
Extraction Mass Balance

| Sample | Glucan Lost | Xylan Lost | Lignin Lost | Std (G) |
|---|---|---|---|---|
| 1 | 15.71% | 6.49% | 4.88% | 0.01% |
| 2 | 12.60% | 6.21% | 31.09% | 0.02% |
| 3 | 15.85% | 2.03% | 15.11% | 0.01% |
| 4 | 14.55% | 8.95% | 32.28% | 0.01% |
| 5 | 14.11% | 7.68% | 35.55% | 0.01% |
| 6 | 10.94% | 6.44% | 1.30% | 0.01% |
| 7 | 12.96% | 4.74% | 3.86% | 0.01% |
| 8 | 12.77% | 7.13% | 11.33% | 0.01% |
| 9 | 13.92% | 7.24% | 11.54% | 0.02% |
| 10 | 14.18% | 8.96% | 15.64% | 0.02% |
| 11 | 26.03% | 10.29% | −0.08% | 0.01% |

Tables 5 and 6 show the composition analysis of unextracted material (Table 5) and extracted material (Table 6). Because the composition of the material remains unchanged during AFEX™ pretreatment, the untreated compositions in Table 5 were used to design an EH experiment for the unextracted materials, with the results show in Table 7 (sample 11). Similarly, the compositions in Table 6 were used to design the second set of EH experiments, with the results shown in Table 7 (Extracted EH). As can be seen, carbohydrate conversion during enzymatic hydrolysis increases for the higher ammonia loadings during pretreatment. Ethanol extraction improved carbohydrate conversion during EH of corn stover, however, it showed a negative impact in the enzymatic digestibility of poplar (Table 7). Ethanol extraction removed 11-15% of glucan and 2-9% of xylan using the conditions tested herein (Table 4). A larger amount of lignin was removed during ethanol extraction, ranging from 1 to 36% of the lignin present in the untreated biomasses (Table 4). In general, lignin extraction was more evident for corn stover than for poplar, under similar experimental conditions (Table 4). When compared to AFEX™ pretreated biomass (sample 11, Table 4), the pretreated/CIII-densified biomass pretreated samples allowed a better lignin extractability and lower carbohydrate extractability.

Composition Analysis

TABLE 5

Unextracted Material Composition
Unextracted Materials Composition

|  | % Glucan | % Xylan | STDEV | % Lignin | STDEV (Lignin) | Ash % | STDEV (ash) |
|---|---|---|---|---|---|---|---|
| CS | 37.81% | 22.26% | 0.35% | 18.93% | 0.35% | 3.86% | 0.10% |
| P | 38.76% | 18.40% | 0.86% | 22.89% | 0.00% | 0.24% | 0.11% |
| AFEX CS | 37.81% | 22.26% | 0.35% | 18.93% | 0.35% | 3.86% | 0.10% |

TABLE 6

Extracted Material Composition
Composition of Extracted Materials

| Sample | Average % Glucan | Average % Xylan | STDEV (G) | Average % Lignin | Lignin STDEV | Ave Ash % | Ash STDEV |
|---|---|---|---|---|---|---|---|
| 1 | 34.90% | 22.79% | 1.20% | 19.72% | 1.90% | 21.69% | 2.86% |
| 2 | 37.59% | 23.75% | 0.53% | 14.84% | 2.20% | 28.83% | 4.25% |
| 3 | 36.01% | 24.68% | 0.18% | 18.19% | 0.54% | 20.67% | 0.33% |
| 4 | 37.61% | 23.59% | 0.98% | 14.92% | 0.99% | 26.76% | 0.13% |
| 5 | 37.01% | 23.42% | 0.02% | 13.90% | 0.17% | 32.35% | 3.14% |
| 6 | 37.40% | 18.65% | 0.51% | 24.48% | 0.35% | 0.24% | 1.69% |
| 7 | 37.78% | 19.63% | 0.76% | 24.64% | 0.36% | 1.44% | 0.94% |
| 8 | 38.13% | 19.27% | 0.40% | 22.89% | 0.08% | 1.76% | 0.58% |
| 9 | 37.88% | 19.38% | 0.16% | 22.99% | 0.95% | 1.58% | 0.18% |
| 10 | 38.59% | 19.43% | 0.29% | 22.40% | 0.04% | 2.13% | 0.35% |
| 11 | 31.48% | 22.47% | 0.04% | 21.32% | 0.03% | 17.99% | 0.76% |

TABLE 7

Enzymatic Hydrolysis
Enzymatic Hydrolysis Conversions

|  | Unextracted EH Conversion 24 Hours | | Extracted EH Conversion 24 Hours | |
|---|---|---|---|---|
| Sample | Glucose | Xylose | Glucose | Xylose |
| 1 | 19.34% | 7.50% | 19.85% | 5.54% |
| 2 | 51.78% | 24.35% | 52.89% | 25.65% |
| 3 | 67.47% | 30.56% | 69.26% | 33.31% |
| 4 | 73.33% | 33.11% | 77.70% | 36.29% |
| 5 | 67.64% | 30.92% | 71.29% | 32.64% |
| 6 | 15.22% | 5.51% | 12.38% | 2.79% |
| 7 | 24.99% | 14.50% | 21.95% | 14.72% |
| 8 | 27.32% | 16.23% | 22.10% | 16.27% |
| 9 | 28.99% | 17.79% | 21.52% | 18.31% |
| 10 | 36.75% | 21.39% | 28.67% | 21.30% |
| 11 | 66.29% | 64.01% | 55.18% | 41.33% |

Conclusion

These results show that a peak conversion can be achieved in Corn Stover with an ammonia loading of 0.75:1. This peak occurs at a value of 77.7% and includes the extraction of the material with ethanol. It can also be shown that the conversion in poplar using AFEX™ technologies and temperature ramping is extremely small at these loading but increases continuously. Further testing could show that loadings over 1:1 achieve conversions more similar to corn stover.

The extraction of these materials shows that a significant amount of glucan, xylan, and lignin can be lost using ethanol extraction. Although extraction does not result in a large increase in enzymatic hydrolysis conversion, solubilizing these sugars can have a significant industrial impact regarding fermentability of the hydrolysates.

The results in table 6 shows the same experimentation on regular 1:1 AFEX™ pretreated pellets, with conversions about 1% lower than pretreated/CIII densified pellets obtained using an ammonia to biomass ratio of 1:1. The AFEX™ pellets are also about 7% lower than the 0.75:1 densified cellulosic conversion pretreated pellets. This shows that the same conversion can be achieved with less ammonia if densified cellulosic conversion pretreatment is used, rather than AFEX™. In one embodiment, higher conversion is obtained in a densified cellulosic conversion pretreatment when reactor packing is optimized to minimize void space above the biomass to reduce the amount of gaseous ammonia occupying the void space.

Figure 6:
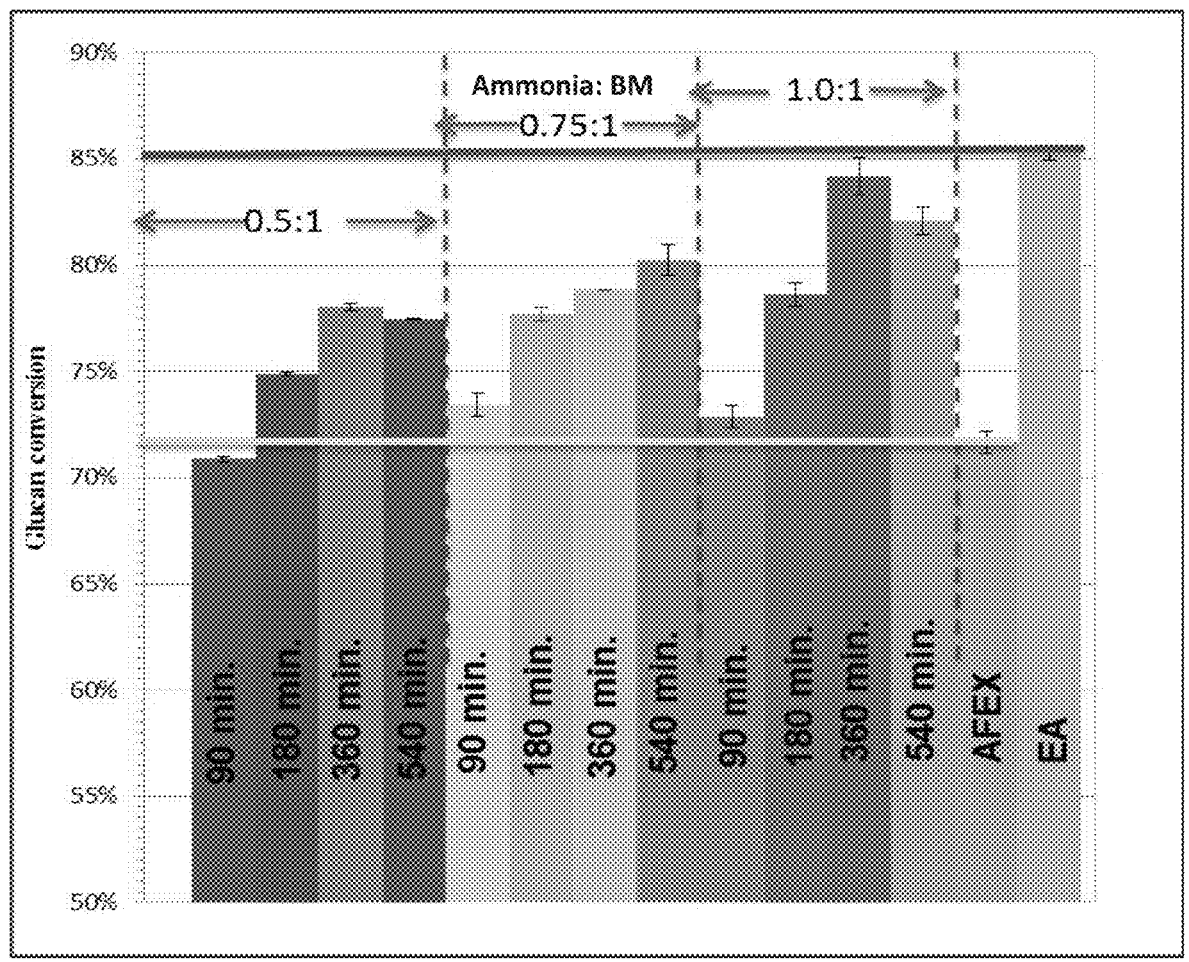
FIG. 6 is a graph showing glucan conversion in densified corn stover using a densified cellulosic conversion pretreatment at three ammonia to corn stover loadings (0.5:1, 0.75:1, and 1:1) at four different residence times (90, 180, 360 and 540 minutes), as compared with an AFEX™ pretreatment of densified corn stover particulates and a conventional EA pretreatment (with loose corn stover) according to various embodiments.

FIG. 6 is a graph showing glucan conversion in corn stover using a densified cellulosic conversion pretreatment at three ammonia to biomass loadings (0.5:1, 0.75:1, and 1:1) at four residence times (90, 180, 360 and 540 minutes) as compared with an AFEX pretreatment of densified corn stover particulates and a conventional EA pretreatment (with loose corn stover).

Figure 7:
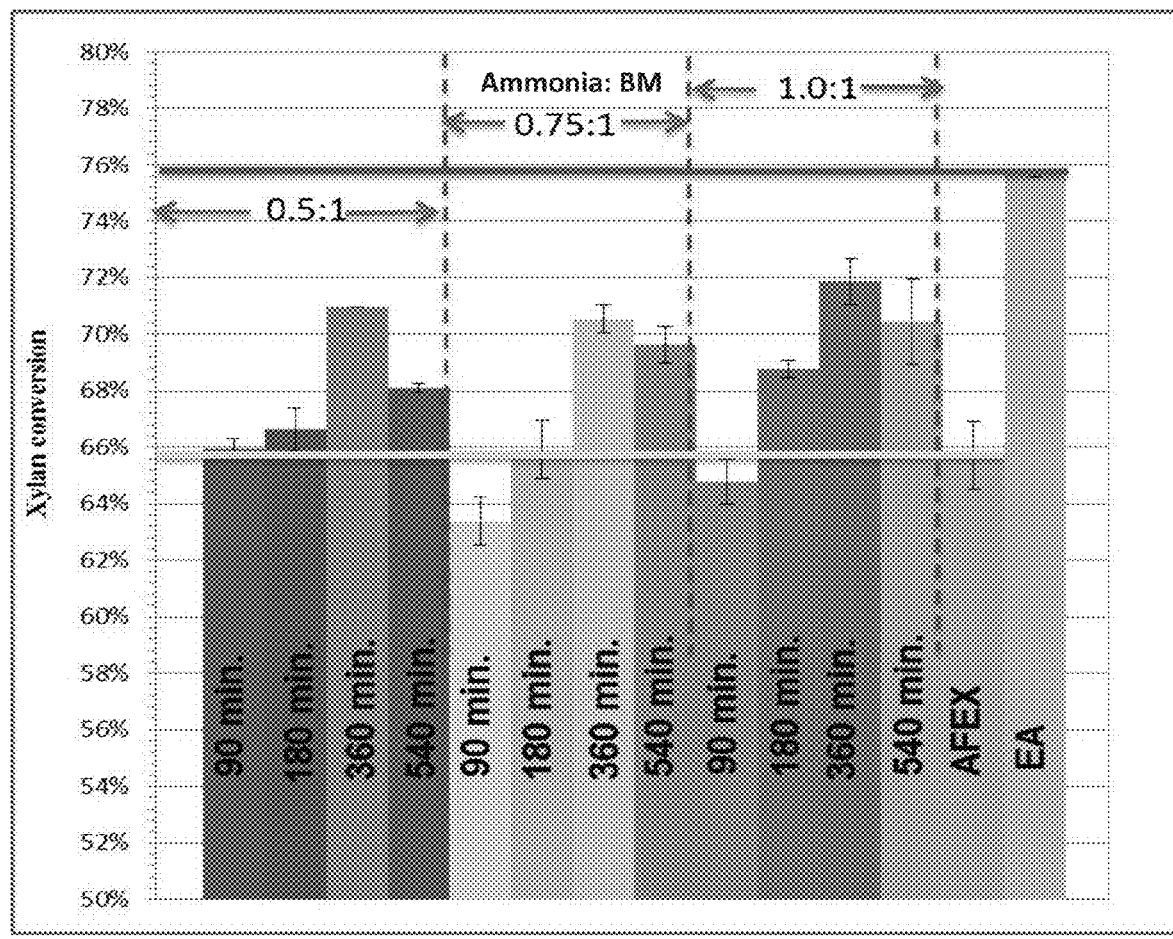
FIG. 7 is a graph showing xylan conversion in densified corn stover using a densified cellulosic conversion pretreatment at three ammonia to corn stover loadings (0.5:1, 0.75:1, and 1:1) at four residence times (90, 180, 360 and 540 minutes) as compared with an AFEX™ pretreatment of densified corn stover particulates and a conventional EA pretreatment (with loose corn stover) according to various embodiments.

FIG. 7 is a graph showing xylan conversion in corn stover using a densified cellulosic conversion pretreatment at three ammonia to biomass loadings (0.5:1, 0.75:1, and 1:1) at four residence times (90, 180, 360 and 540 minutes) as compared with an AFEX pretreatment of densified corn stover particulates and a conventional EA pretreatment (with loose corn stover).

Conventional EA Pretreatment

For comparative purposes, a conventional EA pretreatment using loose corn stover obtained from Michigan State University farms was conducted in 1 Liter (L) high pressure, stainless steel tubular reactors custom built using components purchased from McMaster Car Company, USA, and equipped with individual heating mantles, temperature and pressure indicators. The reactors were connected to the temperature controlled, high pressure 1 L collection vessel to allow separation of ammonia from the extractives by evaporation. In each reactor, 40 grams of corn stover (dry weight basis), containing 10% moisture (wet weight basis) reacted with 240 grams of ammonia for 30 minutes at 120° C. Set point temperature was achieved in the first 7 minutes of reaction, allowing the pressure to reach 83 bar. The pressure in the flash tank was equilibrated with nitrogen to the same pressure observed in the reactor during pretreatment.

Upon reaction completion, the bottom valve in the reactor was open, allowing liquid ammonia and soluble extractives to pass through a stainless steel filter of 50 μm pore size. The ammonia gas was then released from the top of the flash tank by opening a valve, while pressure was maintained in the reactor at 83 bar using nitrogen for 10 minutes. This procedure was designed to maintain ammonia in the liquid state during extraction and allow residual ammonia to be efficiently released from the biomass. After extraction, the reactor and flash tank pressures were equalized to ambient pressure by releasing the ammonia and nitrogen gas from the top of the flash tank. During evaporation, the liquid extractives precipitated in the bottom of the flash tank.

The biomass was then removed from the tubular reactors and allowed to dry overnight in the hood. The system lines were further cleaned with 70% ethanol and 90% acetone (Research Grade, BD Chemicals) to remove residual extractives from the lines, which were collected in the flash tank. All the EA extractives were then drained from the flash tank, collected in a 1 L round bottom flask and further concentrated in vacuum using the rotary evaporator (BUCHI, Switzerland) set at 70° C. The EA extractives were then dried with the Labconco freeze dryer. The dry weight of the extractives and conventionally EA pretreated biomass was further recorded for mass balance purposes. The dried samples were stored at 4° C. in sealed containers to avoid major moisture exposure.

EXAMPLE 2

Enzyme hydrolysis was carried out at 1% glucan loading using enzymatic 7.5 mg Cellic® CTec2, 3.75 mg Htec2, 3.75 mg Pectinex for densified cellulosic conversion pretreatment (at three different ammonia to biomass loading and four different residence times respectively), compared with a conventional EA (loose biomass) pretreatment and AFEX™ (loose biomass) pretreatment.

The samples were aliquoted after 72 hours and subjected to HPLC sugar analysis. Glucan and xylan conversion are shown in FIGS. 6 and 7, respectively. Increase in residence time, showed increased in sugar conversion for densified biomass pretreated samples. The sugar conversion was higher for pretreated/CIII-densified biomass for residence times above 180 minutes when compared to AFEX™ samples. However, all the glucan and xylan conversions were found to be lower when compared to conventional EA pretreatment process.

EXAMPLE 3

These experiments were performed using a modified version of the tubular reactor described in U.S. patent application Ser. No. 13/886,021. In this testing however, the overhead pressure of 400 psi was maintained for a certain residence time and then the pressure was released from the top.

Figure 8:
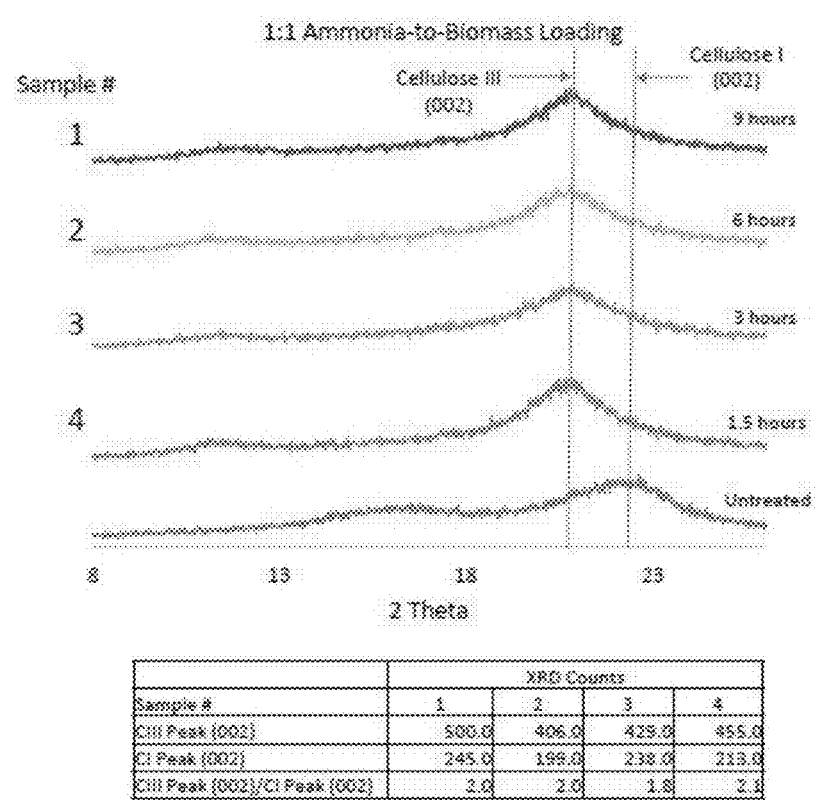
FIG. 8 is an XRD pattern of pretreated/CIII-densified corn stover particulates using a 1:1 ammonia to corn stover loading at various residence times, with untreated densified corn stover particulates used as a control, according to various embodiments.
Figure 9:
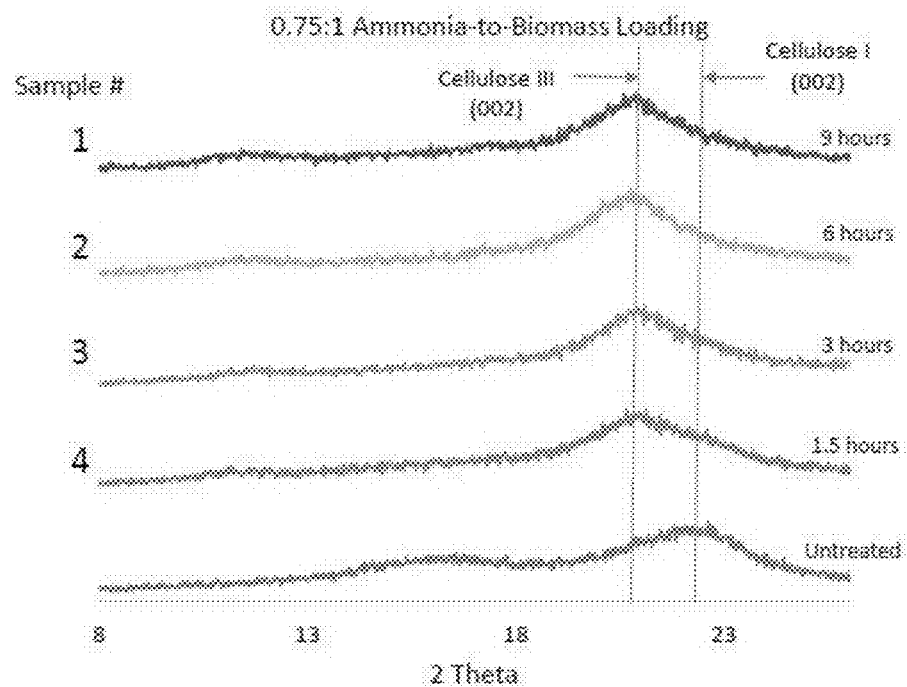
FIG. 9 is an XRD pattern of pretreated/CIII-densified corn stover particulates using a 0.75:1 ammonia to corn stover loading at various residence times with untreated densified corn stover particulates as a control according to various embodiments.
Figure 10:
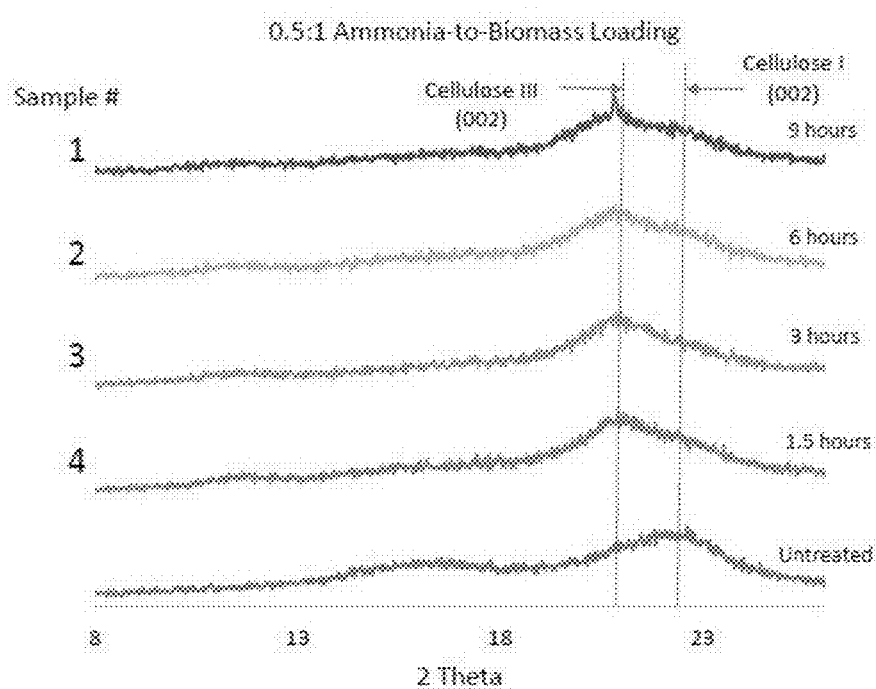
FIG. 10 is an XRD pattern of pretreated/CIII-densified corn stover particulates using a 0.5:1 ammonia to corn stover loading at various residence times with untreated densified corn stover particulates as a control according to various embodiments.

Densified cellulosic conversion pretreatments were carried out using untreated densified corn stover from the source described in Example 1. The densified corn stover was used to produce the results shown in FIGS. 8-10 and 12. The densified corn stover, which contained approximately 10% moisture, was placed inside a stainless steel vessel. Liquid anhydrous ammonia (source as in Example 1) was then added to the reactor at ammonia-to-biomass loadings of 1:1 (FIG. 8), 0.75:1 (FIG. 9) and 0.5:1 (FIG. 10). Heat was supplied to the pretreatment vessel to increase the temperature to 70° C. which was further maintained up to 9 hours (FIGS. 8-10). At 1:1 ammonia loading cellulose I as completely converted to cellulose III at all residence times, while at 0.75:1 ammonia loading full conversion to cellulose III was obtained after 3 hours of pretreatment time.

Figure 11:
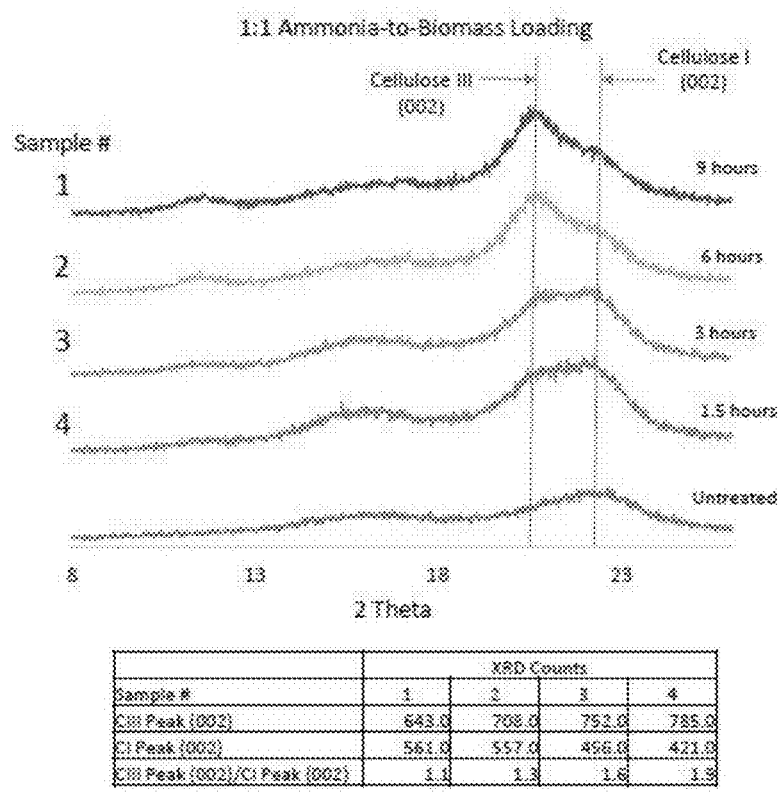
FIG. 11 is an XRD pattern of conventional EA pretreated/CIII-containing (loose) corn stover using a 1:1 ammonia to corn stover loading at various residence times with untreated loose corn stover as a control.

In contrast, when loose biomass was used with 1:1 ammonia-to-biomass loading cellulose III was never fully formed, even at residence times of 9 hours (FIG. 11). At 0.5:1 ammonia loading, full conversion to cellulose III was never obtained for pelletized corn stover, however, the cellulose III peaks show much higher intensity than those associated to cellulose I for all residence times (FIG. 10).

Figure 12:
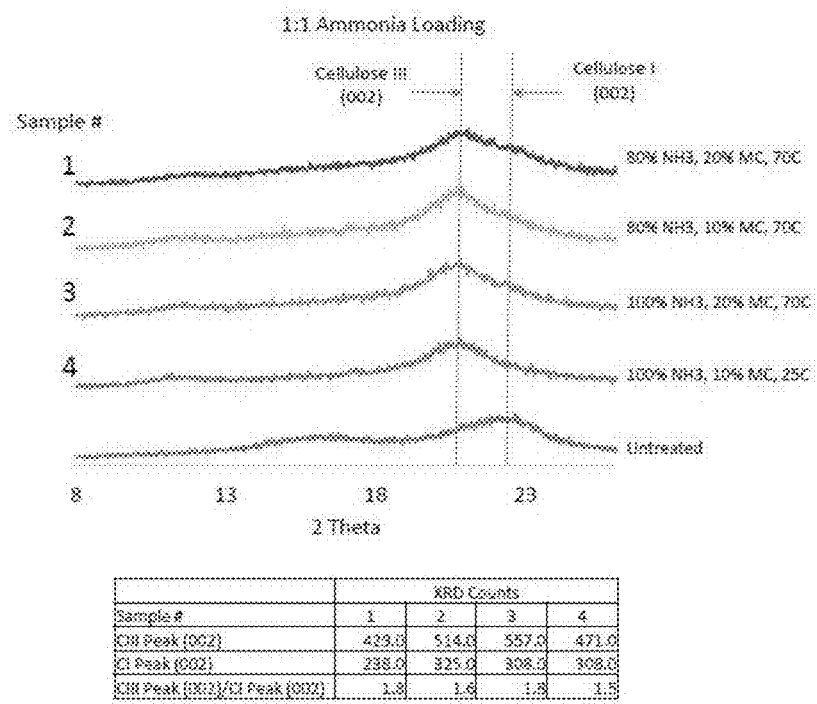
FIG. 12 is an XRD pattern of pretreated/CIII-densified corn stover particulates using a 1:1 ammonia to corn stover loading at various moisture contents and temperatures with untreated densified corn stover particulates as a control according to various embodiments.

The experiments from FIG. 12 were performed using densified biomass with up to 20% moisture content (mwb), ammonia concentrations as low as 80 wt % ammonia and temperatures as low as 25° C. FIG. 12 shows that cellulose III was fully formed even at 25° C., when the densified biomass contained 10% moisture (mwb) and 100% liquid ammonia was used. When high biomass moisture content and 80% ammonia concentration was used, there was some small amount of unconverted cellulose I in the biomass. However, in all the cases tested in FIG. 12, the cellulose III peaks are always the most predominant.

EXAMPLE 4

Raw Materials and Chemicals

Sugarcane bagasse composed of 39.5±0.4% glucan, 25.2±0.1% xylan and 19.4±0.1% lignin was collected from two industrial South African sugarcane sources located in Malelane (TSB Sugar, Mpumalanga) and Mount Edgecombe (SASRI, Kwazulu Natal). The bagasse was milled through a disk mill (Condux LV15M, Netzch-Condux GmbH, Germany) equipped with a 20 mm screen. The size-reduced bagasse samples were sieved in a stacked-sieve system to remove mineral impurities (e.g., sand), bagasse pith and fines smaller than 600 μm×600 μm. Prior to densification, the sugarcane bagasse was milled through a 40 mesh screen.

Corn stover (Pioneer 36H56) composed of 33.7±0.6% glucan, 25.4±0.5% xylan and 14.4±0.8% lignin was harvested from Michigan State University farms (Lansing, Mich.) in November 2014 and milled through a 40 mesh screen. *Miscanthus x giganteus* composed of 44.0±0.1% glucan, 17.9±0.4% xylan and 21.8±0.6% lignin, produced at Michigan State University farms (Lansing, Mich.), was harvested in the spring of 2014 and milled through a 40 mesh screen prior to further usage. Prairie cord grass composed of 42.1±1% glucan, 25.1±0.6% xylan and 18.1%±0.2% lignin was harvested in Brookings, S. Dak. in 2009 and milled through a 4 mm screen. Hybrid poplar (*Populus nigra* var. charkoviensis x caudina cv. NE-19) composed of 34.9±0.2% glucan, 12.7±0.1% xylan and 25.3±1.2% lignin was harvested at the University of Wisconsin Arlington Agricultural Research Station in 2010 and milled through a 20-mesh screen prior to further usage. All the feedstocks were stored at 4° C. in zip-lock bags before usage.

Airgas brand anhydrous liquid ammonia cylinders (Radnor, Pa.) equipped with a dip tube were used for the densified cellulosic conversion pretreatment process. Solvents, sugar standards, acids and bases were from Sigma Aldrich (St. Louis, Mo., USA). The chemicals for the AFEX™ pretreatment were obtained from Airgas (Radnor, Pa.). AFEX™ was performed on sugarcane bagasse according to the methods described in Krishnan, C., Sousa, L. d. C., Jin, M., Chang, L., Dale, B. E. and Balan, V. (2010), Alkali-based AFEX pretreatment for the conversion of sugarcane bagasse and cane leaf residues to ethanol. Biotechnol. Bioeng., 107: 441-450. doi:10.1002/bit.22824, which is hereby incorporated by reference herein in its entirety.

NOVOZYMES (North America, Inc. (Franklinton, N.C., USA) Cellic® brand CTec3 (batch number VDNI0002), Cellic® brand HTec3 (batch number VIN00001) enzymes and DuPont Industrial Biosciences (Palo Alto, Calif., USA) Multifect Pectinase (batch number 4861295753) enzymes were used for hydrolysis.

Biomass Densification

The untreated and AFEX™ pretreated biomass were both mixed with water until a moisture content of approximately 25% (mwb) was reached. The moist biomass was stored in a closed container and placed at 4° C. overnight to allow for substantially complete adsorption of the moisture by the biomass. The moist untreated and AFEX™-pretreated biomass were allowed to reach room temperature prior to densification.

All untreated biomasses, including sugarcane bagasse, corn stover, poplar, Miscanthus and prairie cord grass, were densified in a Buskirk Engineering PM810 (Ossian Ind.) flat die pellet mill using the densification process according to MSU Densification Technologies. The die temperature was maintained at around 70° C. during densification. The densified biomass was collected in a plastic container and allowed to cool to room temperature. Thereafter, the untreated and AFEX™-pretreated densified biomass were oven dried at 50° C. for 48 hr and stored at room temperature in sealed plastic bags before usage.

Densified Cellulosic Conversion Pretreatment of Densified Sugarcane Bagasse

Densified cellulosic conversion pretreatment of densified sugarcane bagasse was performed in 33 mL in-house designed reactors coupled to a control unit to monitor and to control temperature per the process described in L. da Costa Sousa, et. al., *Energ. Environ. Sci.*, 2016, 9, 1215-1223, which is hereby incorporated by reference in its entirety. The reactors were filled with the desired amount of AFEX™ pretreated or untreated densified sugarcane bagasse (10% mwb) together with the anhydrous liquid ammonia which was added to the reactor with a high-pressure syringe pump (Harvard Apparatus, model PHD 2000, Holliston, Mass., USA). Once the anhydrous liquid ammonia was loaded, the reactors were heated up to the desired temperature (between 50° C. and 100° C.) and maintained for the desired reaction time (between 1 hour and 6 hours). After reaching the desired reaction time, the ammonia was released from the system slowly over an approximately two minutes time period. Thereafter, the resulting pretreated/CIII-densified sugarcane bagasse was transferred out of the reactor and left under the fume hood overnight to remove any residual ammonia. After drying, the moisture content of the pretreated/CIII-densified sugarcane bagasse was determined using a moisture analyzer (A&D MX-50, A&D Engineering, Inc., San Jose, Calif., USA) to be around 9% mwb.

A large-scale densified cellulosic conversion pretreatment with high solid-loading enzymatic hydrolysis (HSH-EH) was carried out using 700 mL in-house reactor with a design similar to the 33 mL reactor. The desired amount of densified sugarcane bagasse (dwb) was added to the reactor. Thereafter, the anhydrous liquid ammonia was loaded gravimetrically by weighing the ammonia transferred from a pre-weighed vessel to the reactors. Immediately after filling the system with the ammonia, the reactors were heated to 75° C. or 100° C. and kept at this temperature for the desired reaction time. All subsequent steps were identical to those described for the small-scale reactors.

To assess the influence of lignin removal on enzymatic hydrolysis yields, the densified cellulosic conversion pretreatment process was also performed with lignin extraction (LE), hereinafter referred to as "densified cellulosic conversion-LE pretreatment." Densified cellulosic conversion-LE pretreatment was carried out at the same operational conditions as the densified cellulosic conversion pretreatment. However, in densified cellulosic conversion-LE pretreatment, the bottom of the reactor was connected to a high-pressure lignin collection vessel, while the top of the reactor was connected to a nitrogen line. After reaching the required reaction time, the ammonia was drained along with the dissolved lignin from the reactor to the lignin collection vessel. The exhaust valve from the lignin collector was opened to remove ammonia from the system. Nitrogen was then introduced through the top of the reactor to keep the pressure in the system at approximately 300 psi. This procedure allowed the nitrogen flowing through the system, and allowed the liquid ammonia to flow out together with the dissolved lignin to the lignin collector.

After lignin extraction, the nitrogen flow was cut off to allow the system to release the pressure slowly, i.e., over a period of two minutes. For mass balance purposes, the pretreated-LE/CIII-densified sugarcane bagasse was transferred from the reactor to a pre-weighted tray, which was placed under the fume hood for 48 hr to remove any potential traces of ammonia. The pretreated-LE/CIII-densified sugarcane bagasse was weighed and its moisture content was measured as described above. The extracted pretreated-LE/CIII-densified sugarcane bagasse produced at 100° C. and 75° C. weighed 12% and 2% of the initial densified sugarcane bagasse s input, respectively. The moisture content of the pretreated-LE/CIII-densified sugarcane bagasse after 48 h hood drying for 100° C. and 75° C. pretreatment were 9.7% and 9.6%, respectively.

Experimental Design for Densified Cellulosic Conversion Pretreatment Conditions

A statistical design of experiments (DoE) was applied to assess the effect of temperature (X1), reaction time (X2) and ammonia-to-biomass ratio ($NH_3$:BM) (X3) on conversion of glucan and xylan enzymatic into their respective monomers at 72 hr. To achieve this, a Box-Behnken DoE was employed using software (Minitab Inc., State College, Pa., USA) with 30 experimental points, including replicates and four center point replicates with high and low values of temperature (100° C. and 50° C.), residence time (1 hr and 6 hr) and $NH_3$:BM (0.5:1 and 1:1 (g/g)), respectively.

A quadratic response was carried out on the experimental data as a function of temperature, residence time and $NH_3$:BM ratio (g/g) as independent variables. The interactions between all independent variables were considered in the response surface design. The parameters describing the effect of those variables were considered according to their statistical significance, i.e. p-value ($p<0.05$) and model predictive ability ($R2$ predicted). The regression equations describing the response surface design were used to predict the responses of the various effects within the range of experimental domains. The 72 hr glucan conversion variation as a function of densified cellulosic conversion pretreatment conditions on densified sugarcane bagasse follows the regression equation 72 hr glucan conversion=$17.07+0.1700 X_1+4.684 X_2+3.73 X_3-0.205 X_2^2+0.227 X_1 X_3$. The 72 hr xylan conversion variation as a function of densified cellulosic conversion pretreatment conditions follows the regression equation 72 hr xylan conversion=$-33.90+1.306 X_1+7.86 X_2+21.78 X_3-0.00588 X_1^2-0.355 X_2^2-1.98 X_2 X_3$.

Low Solid Loading Enzymatic Hydrolysis

Low solid loading enzymatic hydrolysis was performed aiming to evaluate the effect of densified cellulosic conversion pretreatment operational conditions on both glucan and xylan conversion into their respective monomers. For this purpose, enzymatic hydrolysis was performed in 20 mL screw-cap scintillation vials with 1% glucan loading (w/w, glucan) and 15 mg of protein/g of glucan in 50 mM citrate buffer (pH 4.8), with 15 mL of reaction volume, and incubated at 50° C. in an orbital shaking incubator (New Brunswick, USA) at 250 rpm for 72 hr. Sodium azide (0.02% w/v) was added as antibiotic to prevent any microbial contamination during the enzymatic reaction. The enzymes were Cellic® CTec3, HTec3 and Multifect Pectinase in ratios (protein dwb) of 68%, 22% and 10%, respectively.

These ratios were previously optimized to maximize total sugar conversion on AFEX™-pretreated/CIII-densified sugarcane bagasse as described in Mokomele et. al., *Biotechnol. Biofuels*, (Submitted 2018, to be published) (hereinafter "Mokomele, et. al."), which is hereby incorporated herein by reference in its entirety. Specifically, a pre-pilot scale AFEX™ pretreatment was performed in a 3.8 L high-pressure reaction vessel (Parr) equipped with temperature and pressure sensors, as described in Lau, M. W., Gunawan, C. & Dale, B. E., *The impacts of pretreatment on the fermentability of pretreated lignocellulosic biomass: a comparative evaluation between ammonia fiber expansion and dilute acid pretreatment*. Biotechnol. Biofuels 11, 1-11 (2009), which is hereby incorporated by reference herein in its entirety.

Densified sugarcane bagasse was treated with AFEX™ at 0.6 g $H_2O$/g dry biomass, and 1.0 g $NH_3$/g dry biomass, 140±2° C., and 60 min. AFEX™-treatment of CLM was performed at 0.7 g $H_2O$/g dry biomass, and 1.0 g $NH_3$/g dry biomass, 135±2° C., and 30 min. Each pretreatment was performed in duplicate. Pretreated samples were stored in sealed bags at 4° C. prior to enzymatic hydrolysis at low and high solids loading.

A second-degree simplex lattice mixture design was carried out to determine optimal combinations of commercial enzymes Cellic® CTec3, Cellic® HTec3 and Pectinex Ultra-SP for the release of sugars from optimally pretreated AFEX™ and StEx sugarcane bagasse and harvested cane leaf matter (CLM). The total enzyme dosage was fixed at 15 mg total protein/g glucan and the ratio of the enzymes ranged from 0 to 1. A total of 40 experiments were generated in Minitab software for each pretreated substrate, including replicates (Minitab Inc.).

The monomeric combined sugar yield (glucose+xylose) from low solids loading enzymatic hydrolysis was used to evaluate the effect of the different enzyme mixtures. Refined cubic regression models were generated, validated and used to predict the optimum enzyme combinations based on the combined sugar yield. Optimal commercial enzyme combinations (CTec3: HTec3: Pectinex Ultra-SP) for AFEX™ and StEx treated bagasse and CLM were used to maximize the saccharification yields for each pretreated substrate (FIGS. 24A, 24B, and 25A-25D).

After 72 hr of enzymatic hydrolysis, the hydrolysates were filtered through a 0.2 µm filter, and soluble sugars, mainly glucose and xylose, were determined using an HPLC equipped with a Bio-Rad Aminex HPX-87H column (Bio-Rad, Hercules, Calif., USA) according to the method described in V. Balan, et. Al., *J. Ind. Microbiol. Biotechnol.*, 2008, 35, 293-301.

High Solid Loading Enzymatic Hydrolysis

For the purpose of evaluating the pretreatment potential under industrially relevant conditions, pretreated/CIII-densified sugarcane bagasse, pretreated-LE/CIII-densified sugarcane bagasse and EA pretreated/CIII-non-densified sugarcane bagasse were subject to EH at a high solid loading (6% glucan loading, w/w). The tests were carried out in duplicate in 250 mL Erlenmeyer flasks with 100 mL reaction volume, in 50 mM sodium buffer (pH 4.6), and incubated at 50° C. in an orbital shaking incubator (New Brunswick, USA) at 250 rpm for 96 hr. Chloramphenicol (50 µg/mL) was added to prevent any microbial contamination during the enzymatic and fermentative reaction. The optimized cocktail of Cellic® CTec3, HTec3 and Multifect Pectinase from Mokomele, et. al., was used for pretreated/CIII-densified sugarcane bagasse at various enzyme loadings of 15, 10 and 7.5 mg protein/g glucan (data not shown). In the first 6 hr of enzymatic hydrolysis, the pH was monitored and adjusted, as needed, to 4.8 using 12.1 M HCl every 2 hr. The blank reactions for both substrate and enzyme complexes were carried out at the same conditions. At the desired enzymatic hydrolysis time (24, 48, 72 and 96 hr), 0.5 mL of sample was taken, incubated at 95° C. for 10 min (Eppendorf, Westbury, USA) to denature the enzymes, centrifuged for 4 min at 3500 rpm.

The supernatant was sampled, diluted (10-fold), filtered through a 0.2 µm filter and analyzed for monomeric sugars as described V. Balan, et. al., *J. Ind. Microbiol. Biotechnol.*, 2008, 35, 293-301, which is incorporated by reference herein in its entirety. After 96 hr of enzymatic hydrolysis, the whole slurry was centrifuged at 10,000 g for 30 min to separate the remaining solids from the hydrolysate. The solid streams were washed with 100 mL of water, centrifuged at 10,000 g for 30 min and the washing water was analyzed in terms of sugar content for mass balance closure purposes. The washed solids were then dried in a freeze-dryer for 72 hr before being subjected to compositional analysis. A sample of the hydrolysate was taken, processed and analyzed for monomeric and oligomeric sugar content. Due to the presence of soluble oligosaccharides in hydrolysates, an acid hydrolysis procedure for estimating the oligomeric sugar content was performed as recommended by NREL/TP-510-42623.[13]

The oligosaccharide content was determined from the increase in concentration of the monomeric sugars after acid hydrolysis. In preparation for fermentation, the pH of the hydrolysates was adjusted to 5.5 using 10 M KOH, sterilized using a 0.22 µm filter and stored at 4° C.

Fermentation

The genetically modified xylose-fermenting strain *Sacchromyces cerevisiae* 424A (LNH-ST) used in the fermentation experiments was obtained from Purdue University. The seed culture of this strain was prepared in 250 mL Erlenmeyer flasks containing 100 mL YPDX (75 g/L glucose, 25 g/L xylose, 10 g/L yeast extract, 20 g/L tryptone)

seed culture medium. A frozen glycerol stock stored at −80° C. was used for seed culture inoculation at an initial optical density of 0.1. The seed culture was incubated at 30° C. and 150 rpm under micro-aerobic conditions for 18 hours. The seed culture reached at optical density (OD600) of about 12 within 18 hours. This seed culture was harvested and used as inoculum for fermentations of the various hydrolysates. The fermentations experiments were initiated with an initial OD600 of 2 (or initial yeast density of 0.96 g/L). Samples were taken at various time points during the fermentation and cell-free supernatants were submitted for HPLC analysis. The total ethanol yield was determined based on the sugar yield during enzymatic hydrolysis, the sugar consumption and metabolic yield during fermentation.

Chemical Analysis

High solid loading unhydrolyzed sugarcane bagasse solids were milled in a knife mill to a particle size of 0.5 mm and characterized for their carbohydrate and lignin content according to the NREL/TP-510-42618.[14] The composition of carbohydrates was determined using Shimadzu HPLC system equipped with an Aminex HPX-87-HR (Bio-Rad, Hercules, Calif., USA) column at 50° C. that was eluted with 5 mM H2SO4 at a flow rate of 0.6 mL/min. The same HPLC analysis conditions were used for the chemical analysis of water-soluble fraction after enzymatic hydrolysis and fermentation. Shimadzu refractive index detector (RID) was used to identify and to quantify glucose, xylose, arabinose, lactic acid and ethanol by means of external calibration. The acid insoluble lignin obtained after acid hydrolysis was quantified gravimetrically and then corrected for the acid insoluble ash that was determined by igniting the content at 550° C. for 5 hr. The acid soluble lignin was determined by ultraviolet spectrophotometry of biomass acid hydrolysates at 320 nm and using an absorptivity of 30 L·(g·cm)$^{-1}$ as is known in the art.

X-Ray Powder Diffraction (XRD)

XRD experiments were carried out on an X-ray powder diffractometer with its beam parallelized by a Gobel mirror (D8 Advance with Lynxeye detector; Bruker, Bruker AXS Inc., Madison, Wis., USA). CuKα radiation (wavelength=1.5418 Å) was generated at 40 kV and 40 mA. The detector slit was set to 2.000 mm. Samples were analyzed using a coupled 2θ/θ scan type with a continuous PSD fast scan mode; 2θ started at 8.000° and ended at 30.0277° with increments of 0.02151°, 136 while θ started at 4.0000° and ended at 15.0138° with increments of 0.01075°. Step time was 1.000 sec (i.e., 1025 total steps, effective total time 1157 sec per run). Cellulose samples (approximately 0.5 g) were placed in a specimen holder ring made of PMMA with 25 mm diameter and 8.5 mm height, rotating at 5 degrees per minute during analysis.

Results and Discussion

Influence of Densified Cellulosic Conversion Pretreatment on the Performance of Low-Solid Enzymatic Hydrolysis The release of sugars obtained during enzymatic hydrolysis of pretreated/CIII-densified sugarcane bagasse is highly affected by the pretreatment conditions, including temperature, residence time and ammonia-to-biomass ratio (NH$_3$:BM, g/g). Enzymatic hydrolysis tests were carried out at 15 mg protein/g glucan with 1% glucan loading (w/w, glucan). An enzyme cocktail of CTec3, HTec3 and Multifect Pectinase from Mokomele, et. al., was used as the optimum for AFEX™ pretreated/densified sugarcane bagasse and pretreated/CIII-densified sugarcane bagasse. Enzymatic hydrolysis performance for pretreated/CIII-densified sugarcane bagasse pretreated under various operational conditions was determined.

Figures 14A, 14B, 14C, 14D, 14E, 14F:
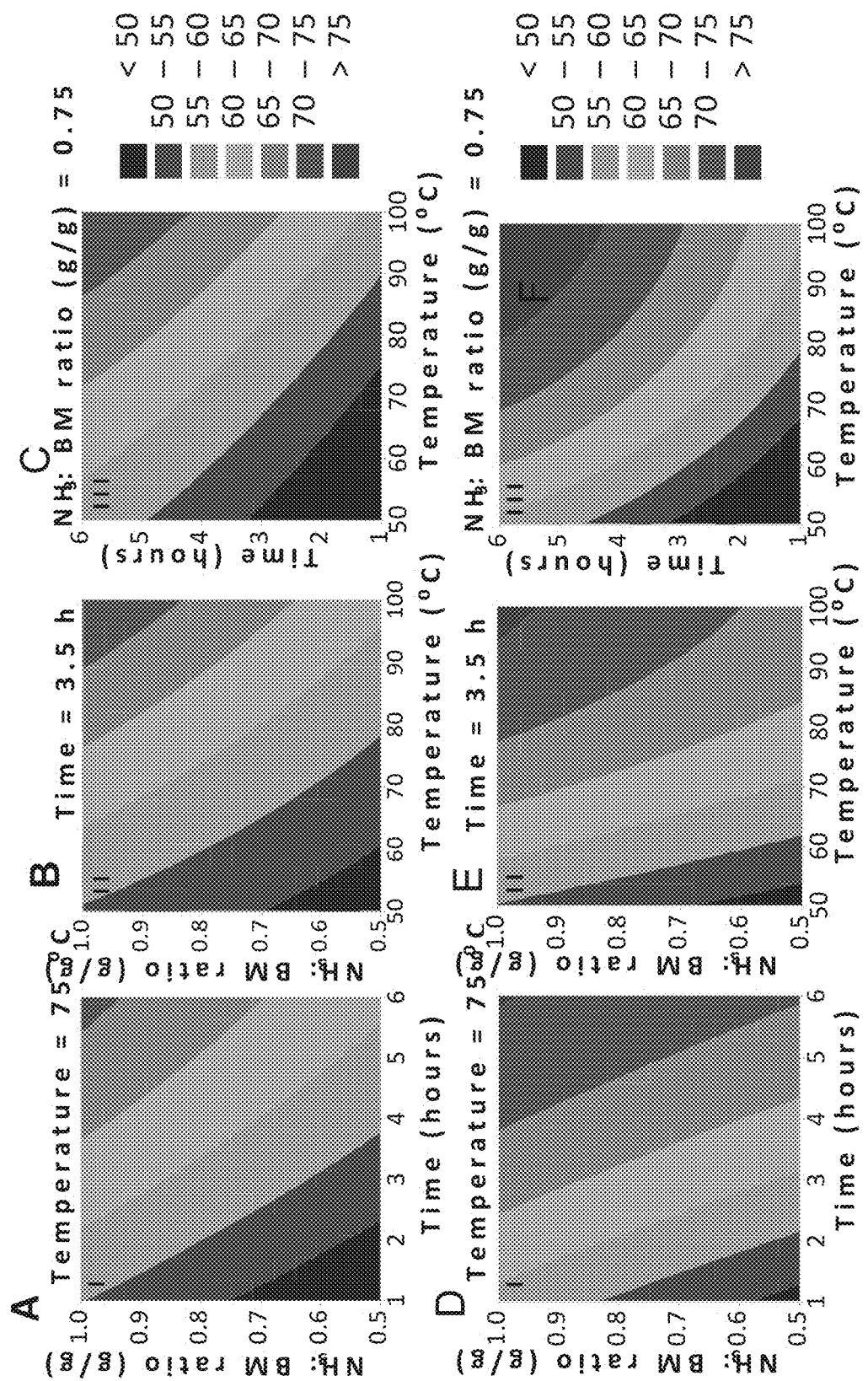
FIGS. 14A-14F are contour plots showing the effect of various densified cellulosic conversion pretreatment conditions (temperature, residence time and ammonia:biomass (NH$_3$:biomass (BM) (g/g)) loading) on 72 hr of enzymatic conversion of (A-C) glucan to glucose and (D-F) xylan to xylose according to various embodiments.

Contour plots and regression models depicting the influence of operational conditions (temperature, residence time and ammonia: biomass (NH$_3$:BM (g/g)) loading) on 72 hr of enzymatic conversion of glucan to glucose are shown in FIGS. 14A-14C; with the effect of conversion of xylan to xylose shown in FIGS. 14D-14F. These contour maps show that the calculated results after pretreated/CIII-densified sugarcane bagasse was subject to EH at 75° C. for 3.5 hr at 0.75:1 NH$_3$:BM (g/g) loading allowed up to 55-60% glucan and xylan enzymatic hydrolysis into their monomers. Significant improvements in carbohydrate susceptibility to enzymatic hydrolysis were observed at 100° C., NH$_3$:BM loading of 1:1 (g/g) for 3.5 hr of reaction time resulting in 78.6±1.8% glucan and 80.6±1% xylan conversion.

The equations for predicting the 72 hr glucan and xylan conversions as a function of densified cellulosic conversion pretreatment are the following:

$$72 \text{ hr glucan conversion}=17.07+0.1700\ X_1+4.684\ X_2+3.73\ X_3-0.205\ X_2^2+0.227\ X_1X_3 \text{ (Adjusted } R^2=0.94\text{); and} \quad 1$$

$$72 \text{ hr xylan conversion}=-33.90+1.306\ X_1+7.86\ X_2+21.78\ X_3-0.00588\ X_1^2-0.355\ X_2^2-1.98\ X_2X_3 \text{ (Adjusted } R^2=0.96\text{); wherein } X_1\text{=temperature}, X_2\text{=reaction time}, X_3\text{=ammonia-to-biomass ratio (NH}_3\text{:BM).} \quad 2$$

Figure 15A:
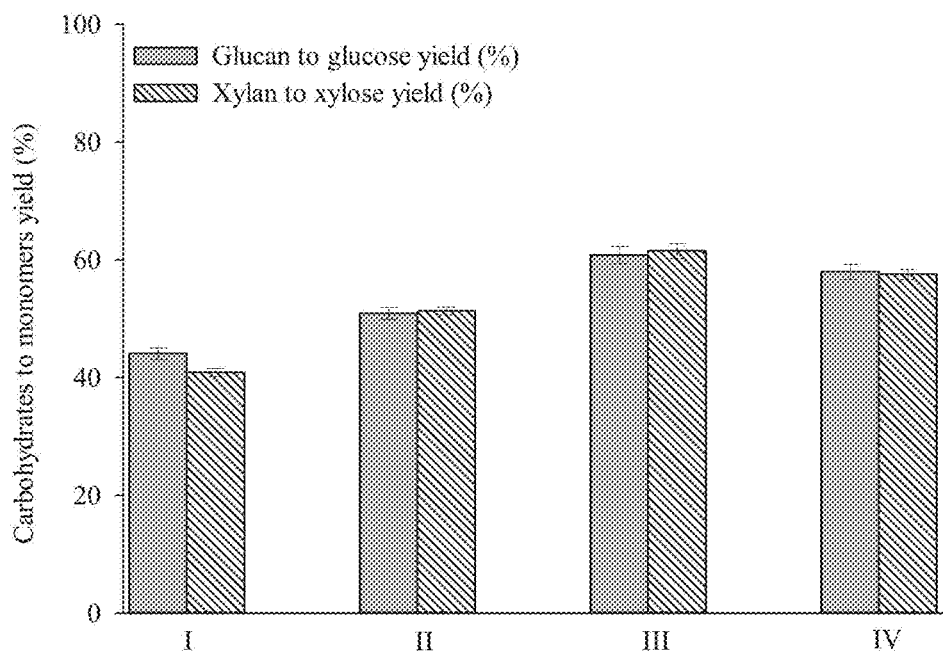
FIGS. 15A-15C are bar graphs showing the effect of various densified cellulosic conversion pretreatment process conditions on a 72 hr low-solid loading enzymatic hydrolysis of pretreated/CIII-densified sugarcane bagasse according to various embodiments.
Figure 15B:
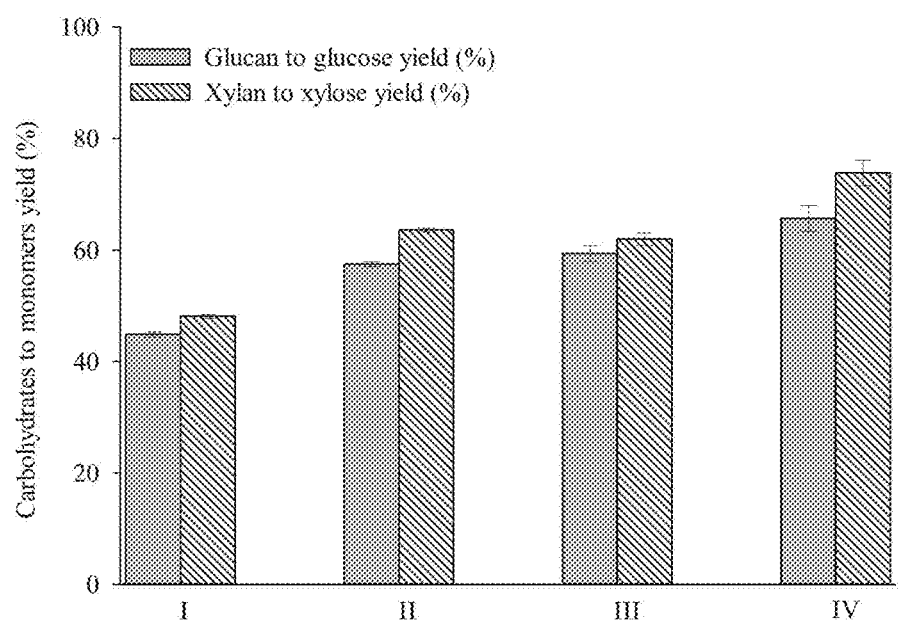
Figure 15C:
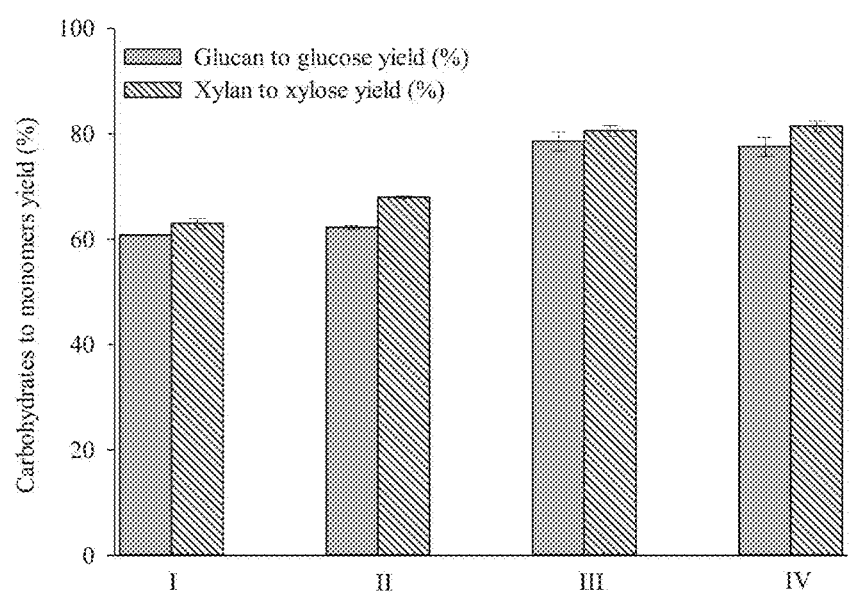

All pretreatment variables studied were found to affect the release of fermentable sugars during enzymatic hydrolysis. FIGS. 15A-15C are bar graphs showing the effect of densified cellulosic conversion pretreatment process conditions on 72 hr low-solid loading enzymatic hydrolysis of pretreated/CIII-densified sugarcane bagasse using the 1% w/w, glucan loading noted above. The enzymatic hydrolysis experiments were conducted with 1% glucan loading and 15 mg enzyme/g glucan.

Potential of Densified Cellulosic Conversion Pretreatment Enzymatic Conversion of Densified Sugarcane Bagasse to Fermentable Sugars at High Solid Loadings To understand the potential benefits of a densified cellulosic conversion pretreatment process for enzymatic hydrolysis, testing with conventionally pretreated densified and non-densified sugarcane bagasse under industrially-relevant conditions was performed. Pretreatment conditions were selected based on i) the optimal parameters that maximize sugar yields as defined in FIGS. 14A-14F (100° C., 3.5 hr with 1:1 NH$_3$:BM (g/g), 800 psi); ii) usage of low temperatures (about 75° C.) and pressures (about 450 psi) in order to decrease both capital expenditure (CAPEX) and operating expenditure (OPEX) (75° C., 4 hr with 1:1 NH$_3$:BM (g/g), 450 psi) and iii) low ammonia loadings (75° C., 4 hr with 0.75:1 NH33:BM (g/g), 450 psi), which are beneficial in terms of energy savings for ammonia recovery operations. All the pretreatment conditions selected allow total carbohydrate conversions (glucan+xylan) higher than 75%. Furthermore, for the densified cellulosic conversion pretreatment, the enzymes were Cellic® CTec3, HTec3 and Multifect Pectinase in ratios (protein dwb) of 71%, 23% and 16%, respectively, in an effort to optimize the enzymatic hydrolysis performance in terms of combined sugar (glucose+xylose) yields.

Figure 16A:
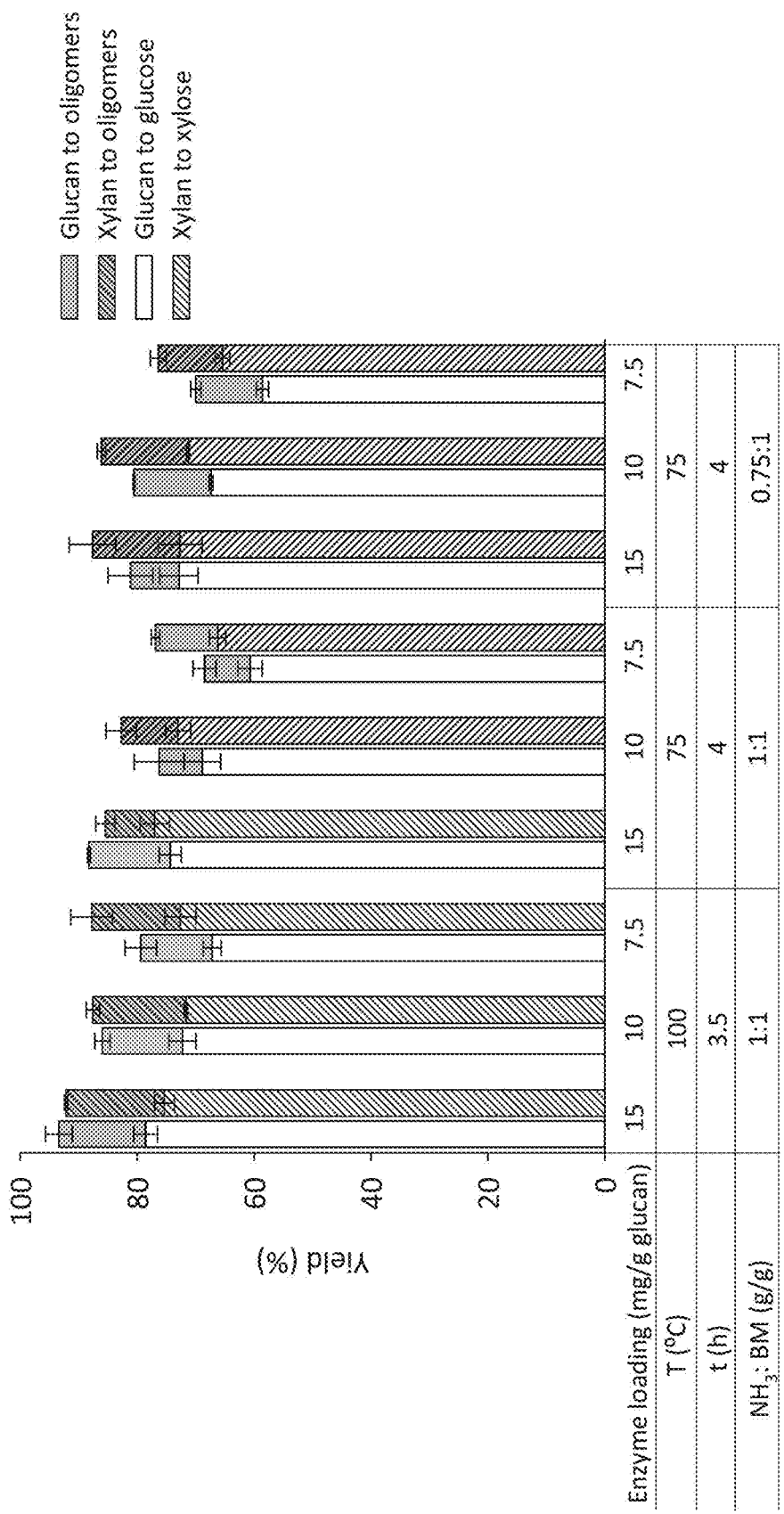
FIG. 16A is a bar graph showing the % yield (kg/100 kg densified sugarcane bagasse) of glucose and gluco-oligomers, xylose and xylo-oligomers following High Solids Loadings-Enzymatic Hydrolysis (HSL-EH) of pretreated/CIII-densified sugarcane bagasse produced under various enzyme loadings according to various embodiments.

FIG. 16A is a bar graph showing the influence of densified cellulosic conversion pretreatment process conditions on glucan to glucose and to gluco-oligomers and on xylan to xylose and to xylo-oligomers yields from sugarcane bagasse under various enzyme loadings. All enzymatic hydrolyses were performed using the optimized enzyme cocktail mixture of Cellic® CTec3, HTec3 and Multifect Pectinase in ratios (protein dwb) of 71%, 23% and 6%, respectively. Solids loading was kept at 6% glucan loading, pH 4.8, and incubated at 50° C. for 96 hr.

Figure 16B:
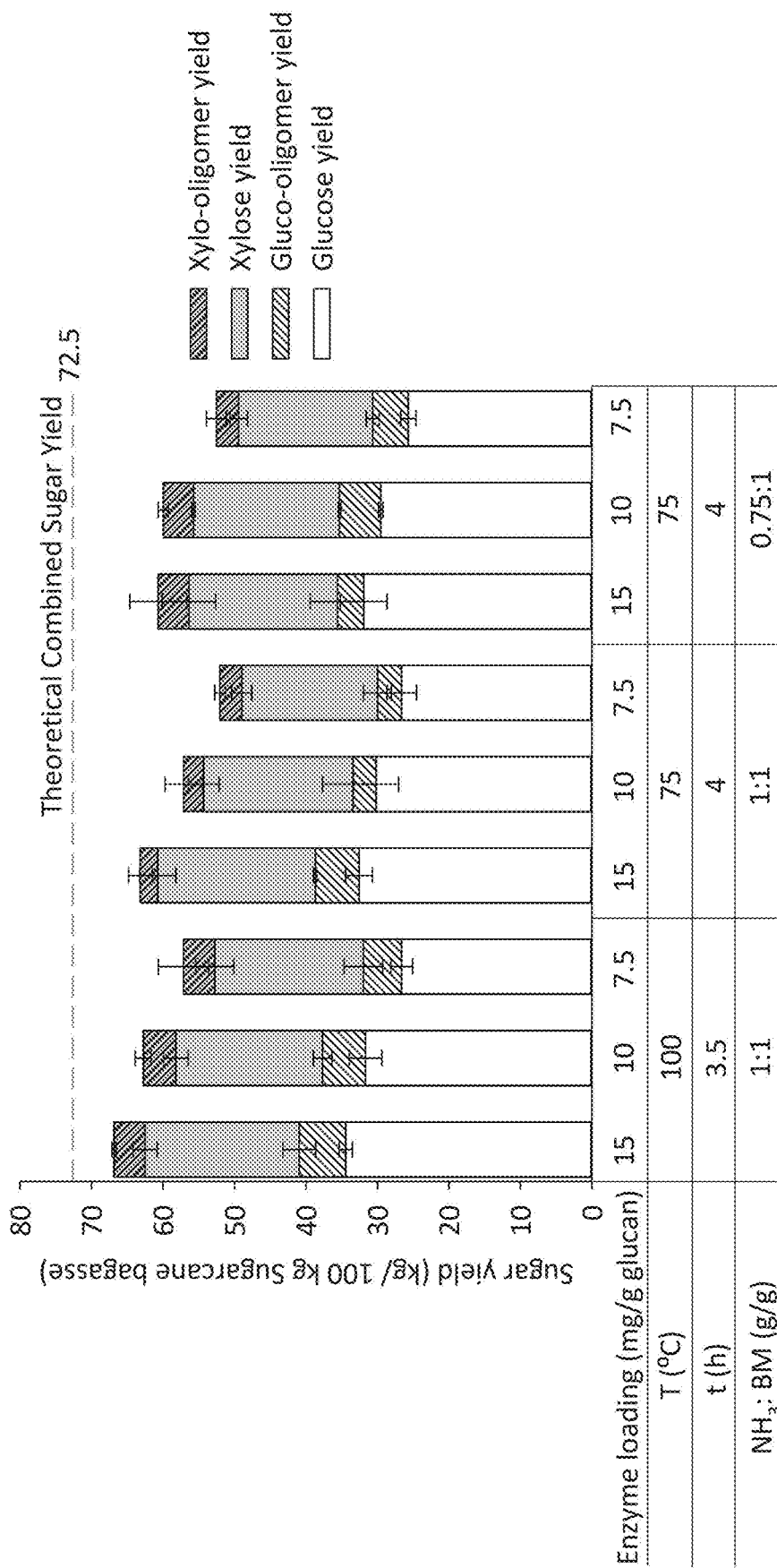
FIG. 16B is a bar graph showing the % yield (kg/100 kg densified sugarcane bagasse) of glucose and gluco-oligomers, xylose and xylo-oligomers following HSL-EH of pretreated/CIII-densified sugarcane bagasse produced under various pretreatment conditions according to various embodiments.

FIG. 16B is a bar graph showing the influence of a densified cellulosic conversion pretreatment and respective operational conditions on HSL-EH of sugarcane bagasse. This graph shows the sugar yields (both monomeric and oligomeric) per 100 Kg of dry sugarcane bagasse loaded in the pretreatment reactor.

Figure 17:
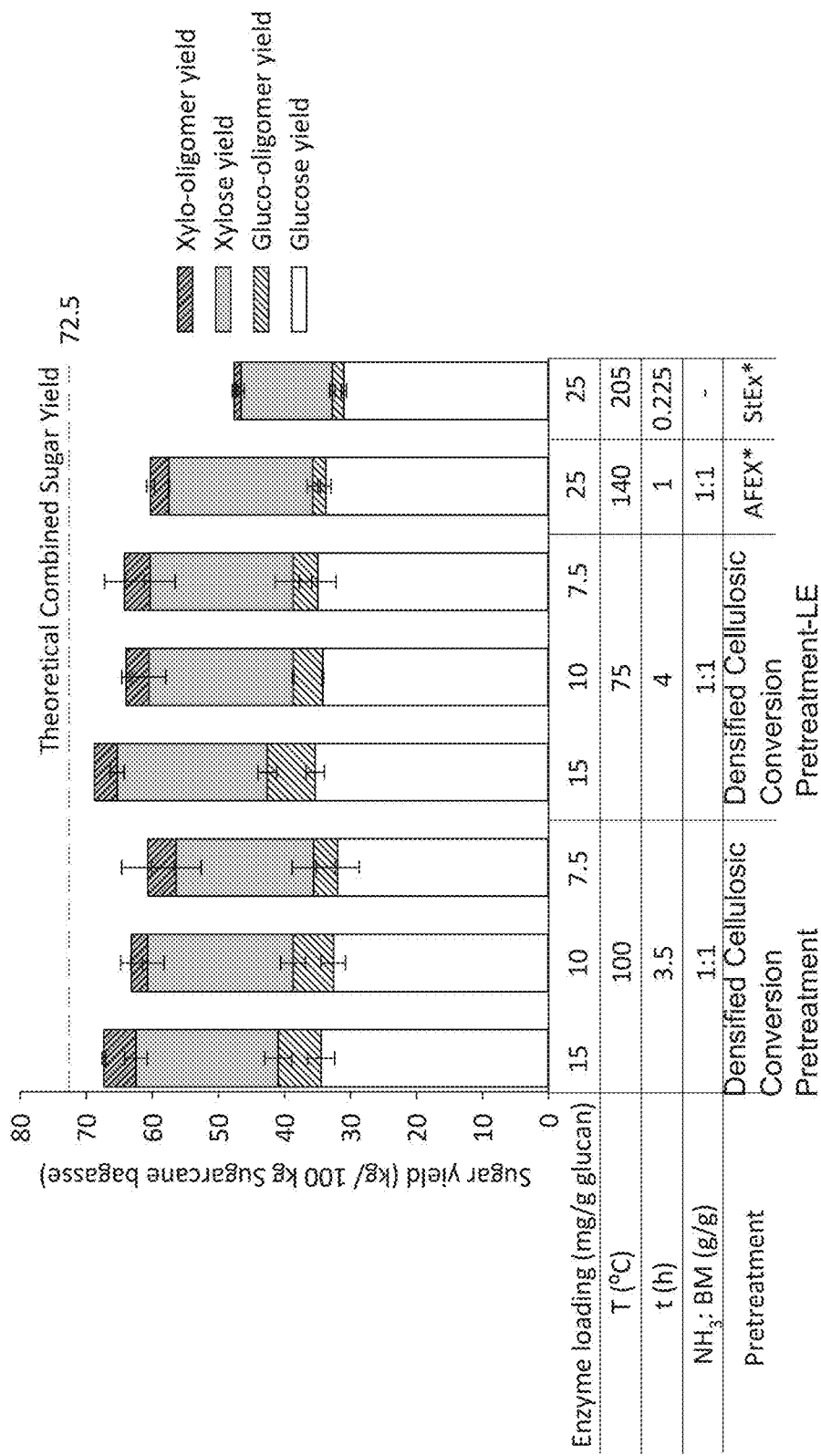
FIG. 17 is a bar graph showing a comparison of the % yield (kg/100 kg densified sugarcane bagasse) of glucose and gluco-oligomers, xylose and xylo-oligomers following HSL-EH at various enzyme loadings on pretreated/CIII-densified sugarcane bagasse to the % yield of these components following HSL-EH at an enzyme loading of 25 mg/g glucan on AFEX™ pretreated/densified sugarcane bagasse and steam explosion (StEx) pretreated/sugarcane bagasse whole slurry according to various embodiments.
Figure 18A:
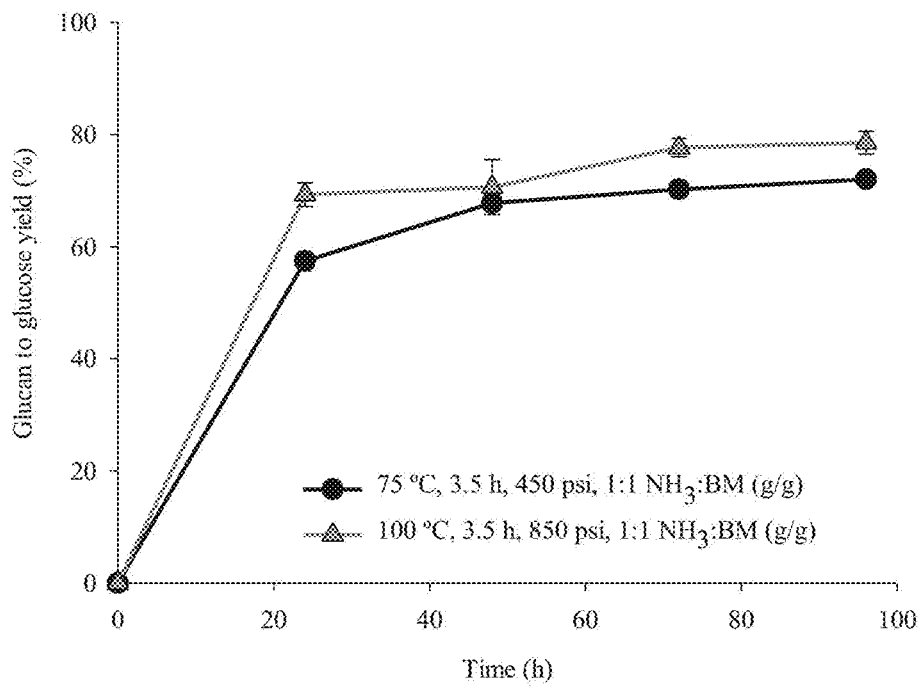
FIGS. 18A and 18B show the % yield (kg/100 kg densified sugarcane bagasse) of (A) glucose and B) xylose following HSL-EH of pretreated/CIII-densified sugarcane bagasse produced at different pretreatment temperatures according to various embodiments.
Figure 18B:
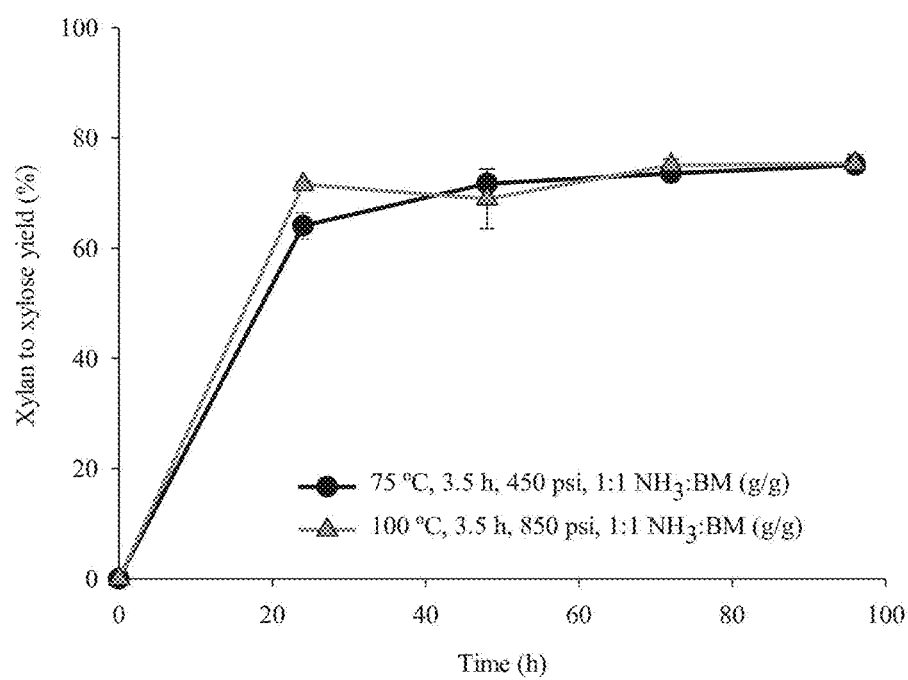

FIGS. 17A and 17B are graphs showing the effect of densified cellulosic conversion pretreatment process temperature on conversion rates of (A) glucan and (B) xylan into glucose and xylose, respectively.

To demonstrate the effect of pretreatment temperature on enzymatic hydrolysis rates and yields, the densified cellulosic conversion pretreatment process was performed at a high temperature of 100° C. with 1:1 $NH_3$:BM loading (g/g) at 15 mg enzyme/g glucan. This resulted in 78.6±2% glucan to glucose and 75.3±1.7% xylan to xylose conversion yields, which correspond to a total monomeric yield of 56±1.9 kg/100 kg of densified sugarcane bagasse. These results show the benefits of performing a densified cellulosic conversion pretreatment at high temperatures. However, high operation temperatures result in higher OPEX and CAPEX, each of which is associated with high energy inputs and operating pressures (approximately 850 psi at 100° C.), respectively. High pressures, however, are less desirable in continuous operations. Thus, the optimal temperature for the enzymatic conversion of densified sugarcane bagasse appears to be a compromise between a temperature high enough to promote de-esterification reactions and, at the same time, a temperature as low as possible to minimize both OPEX and CAPEX.

Figure 19:
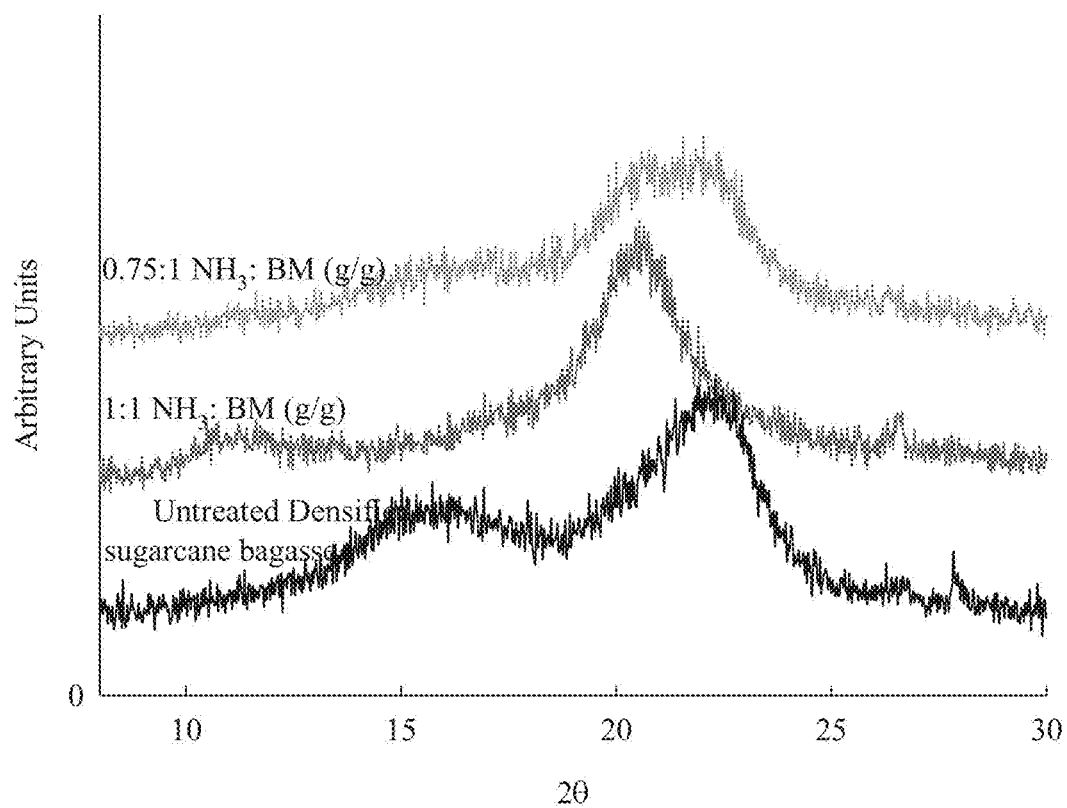
FIG. 19 is an XRD pattern of the crystallinity of pretreated/CIII-densified sugarcane bagasse produced under various ammonia loadings as compared to untreated/CIII-densified sugarcane bagasse according to various embodiments.

Ammonia-based technologies are also evaluated based on the amount of ammonia used in the pretreatment step, as the costs for recovery and reuse are highly dependent on the amount of ammonia added to the process. As such, additional tests were performed to evaluate ammonia use. Specifically, densified sugarcane bagasse pretreated with 0.75:1 $NH_3$:BM loading (g/g) resulted in a slight reduction, i.e., 1-3 kg of monomeric sugar/100 kg of densified sugarcane bagasse, over those obtained when densified sugarcane bagasse was pretreated with 1:1 $NH_3$:BM loading at 75° C. and 100° C., even when not all native cellulose was converted into CIII as shown in FIG. 19.

When restricting the temperature to 75° C. and a pressure of approximately 450 psi, in a densified cellulosic conversion pretreatment process, longer residence times of approximately four hours were needed to guarantee that all densified sugarcane bagasse was completely submerged in the liquid anhydrous ammonia to ensure that effective ammonia-related reactions could take place to produce high enzymatic hydrolysis yields sugarcane bagasse subject to a densified cellulosic conversion pretreatment process at 75° C. with 1:1 $NH_3$:BM loading for 4 hr at 15 mg enzyme/g glucan, resulted in a total monomeric yield of 54.7 kg±3.1/ 100 kg of densified sugarcane bagasse, which corresponds to a very similar yield to that found for densified sugarcane bagasse subject to a densified cellulosic conversion pretreatment process at 100° C. (56.0±1.9 kg/100 kg of densified sugarcane bagasse).

Referring again to FIGS. 16A and 16B, these bar graphs show the influence of densified cellulosic conversion pretreatment conditions on sugarcane bagasse enzymatic hydrolysis performed under various enzyme loadings based on (A) glucan (glucose and gluco-oligomers) and xylan (xylose and xylo-oligomers) conversion yields and (B) total sugar yield on the basis of 100 kg of untreated sugarcane bagasse. All enzymatic hydrolyses were performed using the optimized enzyme cocktail mixture of Cellic® brand CTec3, HTec3 and Multifect Pectinase in ratios (protein dwb) of 71%, 23% and 6%, respectively. The solid loading was kept at 6% glucan loading (w/w glucan)), pH 4.8, and the biomass was incubated at 50° C. for 96 hr.

The total amount of oligossacharides produced was measured using methods known in the art. Substantial oligosaccharide accumulation, which represents a potential yield loss was also observed. High oligomeric sugar yields, reaching up to 15% and 17% for gluco- and xylo-oligomers, respectively, were found at 100° C., 1:1 $NH_3$:BM loading (g/g) for 3.5 hr. This is equivalent to a sugar yield loss of from about 8 to about 14 kg of monomeric sugars per 100 kg of dry sugarcane bagasse when compared to the theoretical yield if oligosaccharides would be converted to respective monosaccharides.

The use of high enzyme loadings enhances the fermentable sugar yields. However, considering the economics of the process it is undesirable. Thus, the effect of different enzyme loadings (15, 10 and 7.5 mg/g glucan) was explored at the same enzymatic conditions. For all reaction conditions studied, the performance of high-solid loading enzymatic hydrolysis was greatly impaired by the decrease of enzyme loading. For example, at 7.5 mg enzyme/g glucan, a decrease of about 15% on total sugar yield per 100 kg of sugarcane bagasse was observed over those found for 15 mg enzyme/g glucan. However, to achieve similar sugar yields as those obtained under high enzyme loadings, higher pretreatment temperature or ammonia loadings could be needed. Therefore, the ultimate choice between pretreatment options and enzyme loading will depend on a techno-economic analysis.

FIG. 19 shows the performance of a densified cellulosic conversion pretreatment process on a high solids loading enzymatic hydrolysis (HSL-EH) of sugarcane bagasse at various enzyme loadings according to various embodiments. The evaluation of the effect of densified cellulosic conversion pretreatment conditions at various enzyme loadings on enzymatic glucose and xylose monomeric yield from sugarcane bagasse, on the basis of 100 kg of untreated sugarcane bagasse. The optimized enzyme cocktail mixture of Cellic® brand CTec3, HTec3 and Multifect Pectinase in ratios (protein dwb) of 71%, 23% and 6%, respectively, were used for all enzymatic hydrolyses. The solids loading was kept at 6% glucan loading, pH 4.8, and incubated at 50° C. for 96 hr.

The highest monomeric sugar yield of 56±1.7 kg sugar/ 100 kg biomass was found for densified cellulosic conversion pretreatment process performed at the severest conditions, followed by the densified cellulosic conversion pretreatment process at 75° C., 4 hr 1:1 $NH_3$:BM, which resulted in a monomeric sugar yield of 54.7±4.4/100 kg biomass. Besides the lower sugar yield found for 0.75:1 $NH_3$:BM ratio condition (52.8±3.3 kg sugar/100 kg biomass), the usage of lower $NH_3$ loadings are beneficial in terms of energy savings and CAPEX for ammonia recovery operations. However, it is important to point out that in the lower $NH_3$ loading case, longer residence time could be required in order to guarantee that all biomass is in contact with ammonia to completely convert cellulose I to cellulose III. Therefore, densified cellulosic conversion pretreatment process performed at 100° C. and 75° C., 4 h and $NH_3$:BM ratio of 1:1 and 0.75:1 were selected and compared to EA and AFEX™.

The strategy for improving carbohydrate conversion, without using higher enzyme loadings and/or more severe pretreatment conditions, was to perform densified cellulosic conversion pretreatment with lignin extraction (densified cellulosic conversion-LE pretreatment). The process relied on the pretreatment of densified sugarcane bagasse with subsequent lignin removal as described above. A densified cellulosic conversion pretreatment process performed on densified sugarcane bagasse at both 100° C. and 75° C. with 1:1 $NH_3$:BM (g/g) loading was used as a control. The densified cellulosic conversion-LE pretreatment conducted at 100° C. resulted in an effective lignin delignification of 30%. However, when the process was performed at 75° C., a substantial decrease on the delignification yield up to 19% was observed.

Figure 20:
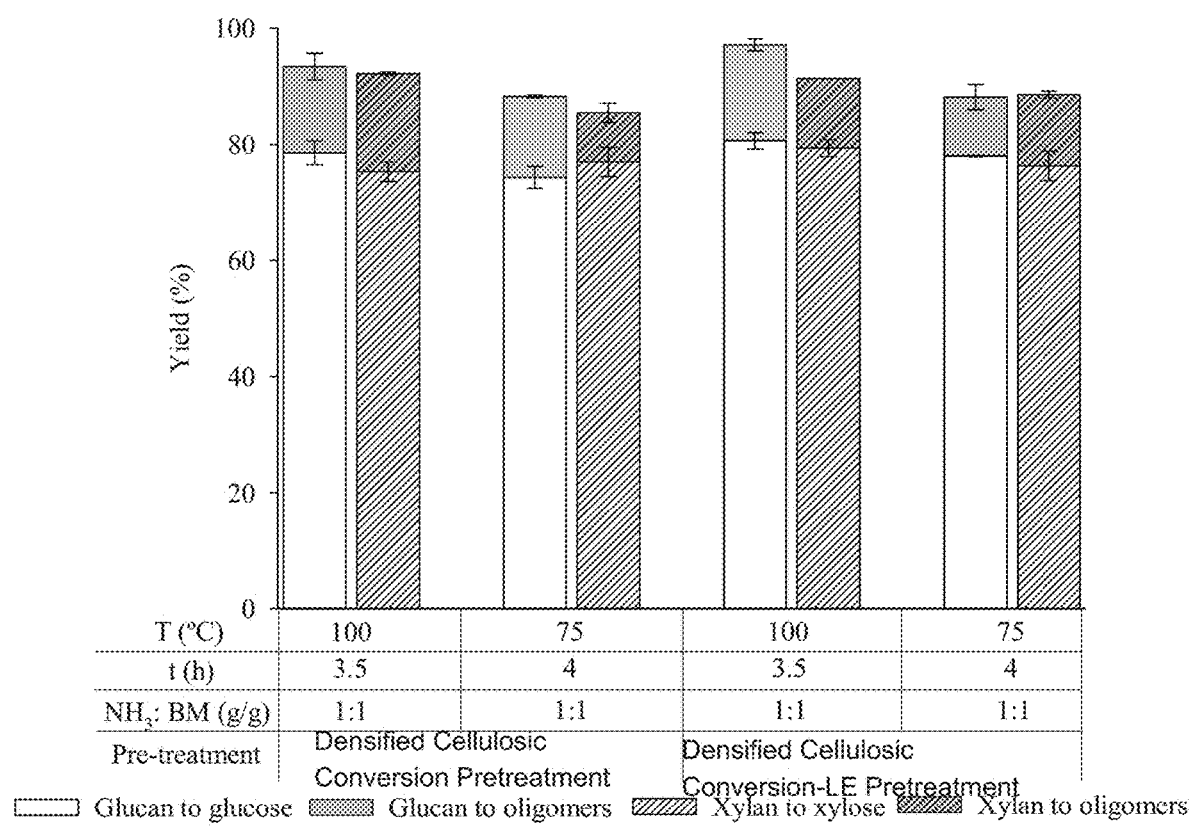
FIG. 20 is a bar graph showing the % yield (kg/100 kg densified sugarcane bagasse of glucose and xylose following HSL-EH of pretreated/CIII-densified sugarcane bagasse subject to a subsequent lignin extraction step (hereinafter "pretreated-LE/CIII-densified sugarcane biomass) according to various embodiments.

FIG. 20 depicts the influence of delignification extraction on total glucan (glucose and gluco-oligomers) and xylan (xylose and xylo-oligomers) conversion yields obtained both the densified cellulosic conversion pretreatment and the densified cellulosic conversion-LE pretreatment under different pretreatment conditions.

At 100° C., densified cellulosic conversion-LE pretreatment resulted in an improvement of total glucan conversion by 4% over that found for densified cellulosic conversion pretreatment, yielding 97% overall glucan conversion. Regarding the densified cellulosic conversion-LE pretreatment performed at 75° C., no significant improvement on total glucan conversion was found, probably due to low delignification yield. This comparison demonstrates the advantages of extracting lignin to obtain higher glucan conversion yields without increasing enzyme and/or ammonia loadings. The high sugar yields associated with a densified cellulosic conversion-LE pretreatment can be attributed to the ability of ammonia to dissolve lignin. This, in turn, contributed to an increase of the susceptibility of biomass surface to enzymatic hydrolysis.

Comparison With Various Technologies

Figure 21A:
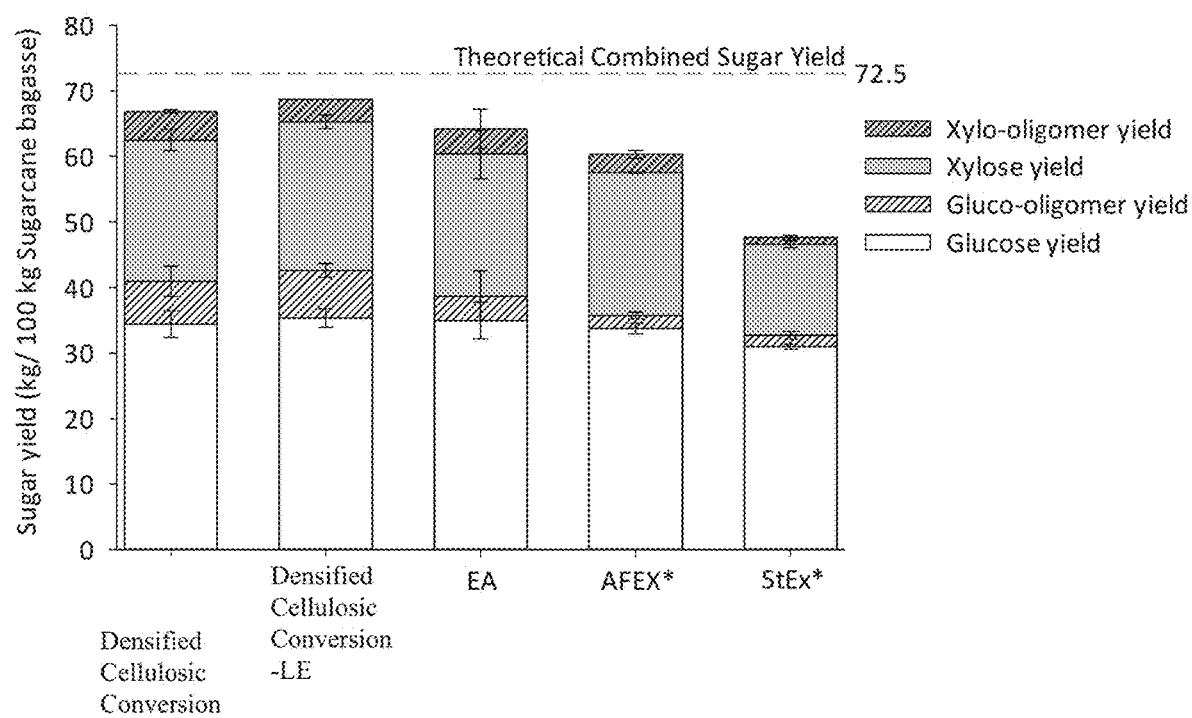
FIG. 21A is a bar graph showing a comparison of the % yield (kg/100 kg densified sugarcane bagasse) of glucose and xylose following HSL-EH at an enzyme loading of 15 mg/g glucan on pretreated/CIII-densified sugarcane bagasse to the % yield of these components following HSL-EH at the same enzyme loading on EA-pretreated/CIII-loose sugarcane bagasse, and at an enzyme loading of 25 mg/g glucan on AFEX™ pretreated/densified sugarcane bagasse, and on StEx pretreated/sugarcane bagasse whole slurry according to various embodiments.
Figure 21B:
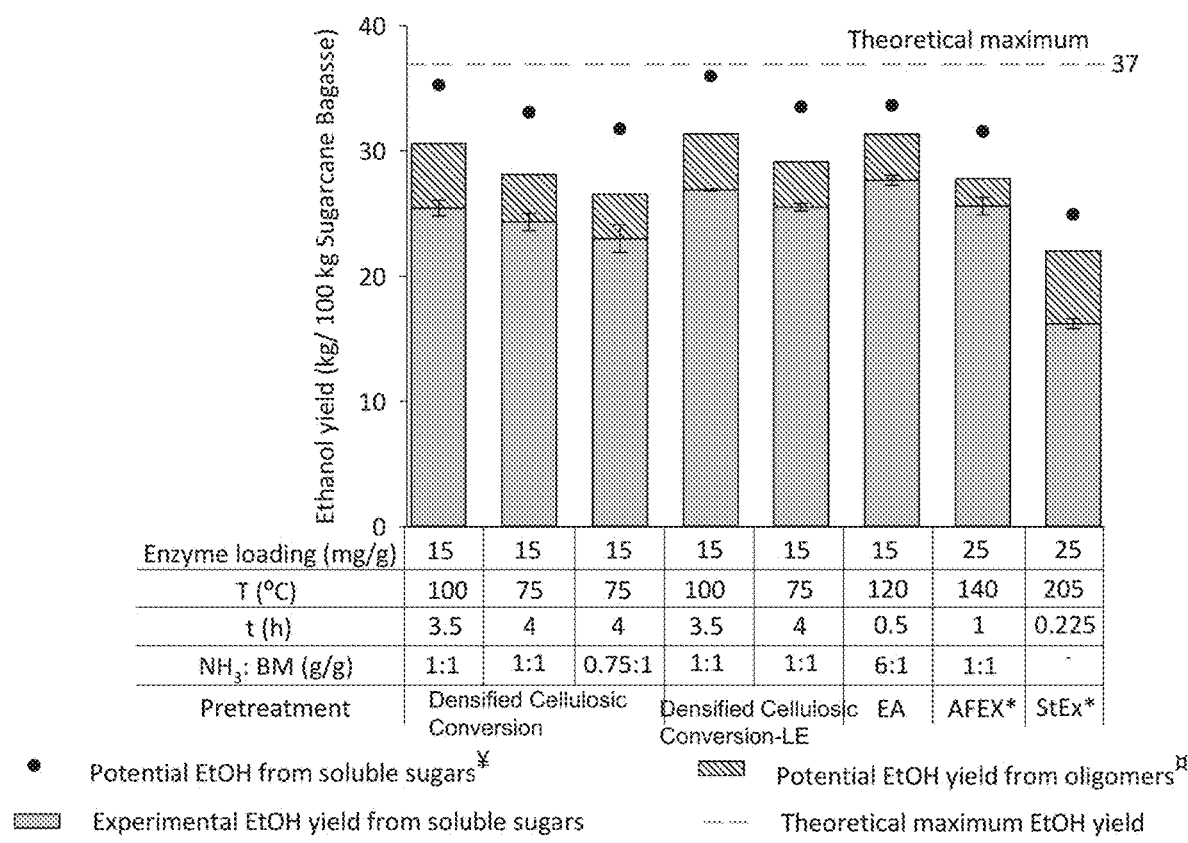
FIG. 21B is a bar graph showing fermentation performance, i.e., ethanol yields, using the pretreatments and biomass as described in FIG. 21A according to various embodiments.

One embodiment of a densified cellulosic conversion-LE pretreatment was compared with conventional technologies, namely, EA (with loose sugarcane bagasse), AFEX™ on densified sugarcane bagasse, and StEx on loose sugarcane bagasse, on the basis of the production of fermentable sugars (FIG. 21A) and ethanol (FIG. 21B). An embodiment of the novel densified cellulosic conversion pretreatment process was used as a control.

The EA was performed with the following parameters: 1) 3:1 ammonia to biomass ratio, at 190° C., 10% moisture and 2) 6:1 ammonia to biomass ratio at 120° C. and 10% moisture, both of which are discussed as possible EA pretreatment parameters in U.S. Pat. No. 9,644,222 to Applicant, which is hereby incorporated herein by reference in its entirety. Stex was performed in an automated batch pilot-scale unit (IAP GmBH, Graz, Austria) equipped with a 19 L reaction vessel, a 100 L expansion vessel and a 40 bar steam boiler according to the method discussed in Agudelo, Roberto A., et. al., *Steam explosion pretreatment of triticale (x Triticosecale Wittmack) straw for sugar production*, New Biotechnology, Vol. 33, 153-163, January 2016, which is hereby incorporated herein by reference in its entirety. The StEx reaction vessel, preheated to 185° C., was top-loaded with 500 g (dry basis) of water-impregnated bagasse or CLM and was directly heated to the desired temperature using 30 bar (absolute) saturated. The bagasse and the CLM were pretreated at temperatures and residence times ranging from 185 and 215° C. and 10 and 15 min, respectively (FIGS. 24A-24D and FIGS. 25A-25D).

After the required pretreatment time had elapsed, the reactor contents were discharged into the expansion vessel maintained at atmospheric pressure. Each pretreatment was performed in duplicate. About 100 gram samples of the pretreatment slurry were characterized in terms of the total solids (TS), water soluble solids (WSS), water insoluble solids (WIS), and pH in triplicate. The remaining slurry was separated into a solid (pressed solids) and a liquid fraction (pretreatment $C_5$-liquor) using a pneumatic piston press (Eurotool TY5001, South Africa). The pressed (unwashed) solids with an approximate moisture content of 65% (w/w) were air dried at 35° C. to a moisture content of 15% (w/w).

These pretreatments were selected for comparison as they are all alkaline-type pretreatments. EA is a known alkaline-type technology with a similar reaction method as a densified cellulosic conversion-LE pretreatment, i.e., both extract lignin and modify the cellulose crystalline structure. In addition, EA has been reported as the most effective ammonia-based pretreatment for fermentable sugars and ethanol production[8]. AFEX™ is also a known conventional alkaline-type technology which does not result in CIII formation or lignin removal. StEx, an acidic-type pretreatment, was used as a comparison to alkaline-type pretreatments.

For this testing, 100 kg of untreated sugarcane bagasse was used. AFEX™ and StEX enzymatic hydrolysis was carried out using 25 mg of protein/g of glucan. Densified cellulosic conversion LE-pretreatment and EA enzymatic hydrolysis was carried out using 15 mg of protein/g of glucan. The optimized enzyme cocktail mixture of Cellic® brand CTec3, HTec3 and Multifect Pectinase in ratios (protein dwb) of 71%, 23% and 6%, respectively, was used. Solids loading was kept at 6% glucan loading, pH=4.8. The mixture was incubated at 50° C. for 96 hr. The same pretreatments, pretreatment conditions and types of biomass were used to determine total sugar yields, namely glucose, gluco-oligomers, xylose and xylo-oligomers (FIG. 21A) and ethanol (EtOH) yields (FIG. 21B). Ethanol yields were calculated on the basis of 100 kg of untreated densified sugarcane bagasse input. The theoretical maximum for sugar and ethanol yields was calculated based on the initial glucan and xylan contents in untreated densified sugarcane bagasse. AFEX™ and StEx sugar and ethanol yields were obtained using the process discussed in Mokomele. et al. The potential ethanol yield from oligomers was estimated based on the metabolic yields and sugar consumption obtained in each operational condition (See Table 8). The potential ethanol yield from soluble sugars was estimated using the assumption that all soluble sugars could converted into ethanol, in a scenario where enzymes and microorganisms are 100% efficient in converting soluble sugars into ethanol. The highest metabolic yield obtained was 97.5% using densified cellulosic conversion-LE pretreatment at 100° C. for 3.5 hr and 1:1 $NH_3$:BM (g/g).

TABLE 8

Metabolic yields and sugar consumption obtained in various operational conditions

| Pre-treatment | Operational conditions | Initial concentration Glucose (g/L) | Initial concentration Xylose (g/L) | Consumption (%) Glucose | Consumption (%) Xylose | $Y_{x/s}$ ($g_{CDW}/g_{sugar}$) | Metabolic Yield (%) | $Y_{p/s}$ ($g_{EtOH}/g_{sugar}$) | EtOH Concentration (g/L) | EtOH Productivity (g/L/hr) | Process Yield (%) |
|---|---|---|---|---|---|---|---|---|---|---|---|
| Densified Cellulosic Conversion | 100° C., 3.5 hr, 850 psi, 1:1 NH₃:BM (g/g) | 57.8 | 36.9 | 98.7 ± 0.0 | 83.5 ± 0.5 | 0.0461 | 96.0 ± 0.4 | 0.454 | 38.9 | 25.4 ± 0.6 | 69 |
| | 75° C., 4 hr, 450 psi, 1:1 NH₃:BM (g/g) | 57.5 | 38.1 | 98.7 ± 0.1 | 81.7 ± 0.5 | 0.0458 | 96.2 ± 0.4 | 0.445 | 37.8 | 24.3 ± 0.7 | 66 |
| | 75° C., 4 hr, 450 psi, 0.75:1 NH₃:BM (g/g) | 53.7 | 36.6 | 98.7 ± 0.1 | 85.8 ± 2.0 | 0.0444 | 92.8 ± 0.9 | 0.436 | 38.7 | 23.0 ± 1.1 | 62 |
| Densified Cellulosic Conversion-LE | 100° C., 3.5 hr, 850 psi, 1:1 NH₃:BM (g/g) | 60.9 | 36.2 | 99.0 ± 0.1 | 89.5 ± 0.4 | 0.0446 | 97.5 ± 1.8 | 0.468 | 42.5 | 26.9 ± 0.1 | 73 |
| | 75° C., 4 hr, 450 psi, 1:1 NH₃:BM (g/g) | 58.5 | 37.3 | 98.9 ± 0.1 | 84.3 ± 0.1 | 0.0454 | 96.2 ± 0.3 | 0.451 | 39.5 | 25.5 ± 0.3 | 69 |
| EA(loose) | 120° C., 0.5 hr, 1200 psi, 6:1 NH₃:BM (g/g) | 54.8 | 36.3 | 99.2 ± 0.0 | 93.6 ± 1.0 | 0.0454 | 93.1 ± 1.0 | 0.454 | 41.0 | 27.6 ± 0.4 | 75 |
| AFEX™* (densified) | 140° C., 1 hr, 400 psi, 1:1 NH₃:BM (g/g) | 59.0 | 37.01 | 100 | 96 | 0.0493 | 92 | 0.461 | 44.2 | 25.6 | 69 |
| StEx* (loose) | 200° C., 0.1 hr | 69.7 | 26.1 | 98 | 37 | 0.0291 | 87 | 0.362 | 34.6 | 16.2 | 44 |

EA—Extractive Ammonia; AFEX™—Ammonia Fiber Expansion; StEx—Steam-Explosion; EtOH—Ethanol; CDW—Initial inoculum concentration.
*Results obtained by Mokomele et al.[11]

Surprisingly, pretreated-LE/CIII-densified sugarcane biomass exhibited the highest total sugar yield of approximately 68.8±1.8 kg/100 kg of densified sugarcane bagasse. This sugar yield represents a pronounced improvement over the pretreated/CIII-densified sugarcane biomass, as the theoretical maximum sugar yield for is 72.5 kg/100 kg of densified sugarcane bagasse. However, 10.1±1 kg of 100 kg of densified sugarcane bagasse (out of the 68.8 kg/100 kg densified sugarcane bagasse) corresponded to oligomeric sugars.

Although EA showed good performance in the removal of lignin and modification of CI into CIII at a temperature of 120° C. with 6:1 NH₃:BM loading (g/g), it did not perform as well as the densified cellulosic conversion-LE pretreatment. EA pretreatment generated a total sugar yield of 64.2 kg/100 kg of densified sugarcane bagasse, which corresponds to 7% lower yield than that found for the densified cellulosic conversion-LE pretreatment. This interesting result can be explained by the densification impact on biomass structure, which subsequently affects pre-treatment and enzymatic hydrolysis processes.

Although densification helped to improve pretreatment effectiveness, these results indicate that the densification process alone is not responsible for improving enzymatic yields, as the untreated loose (used as a control) and untreated densified sugarcane bagasse revealed similar glucan conversion yields (15% vs. 16%, respectively).

Unlike the results obtained with densified cellulosic conversion-LE pretreatment and EA, both AFEX™ and StEx demonstrated a reduced ability to produce fermentable sugars. The AFEX™-pretreated/CIII-densified sugarcane bagasse with 25 mg/g glucan of enzyme loading resulted in a total sugar yield of 60.3±1.1 kg/100 kg of densified sugarcane bagasse, which corresponds to a decrease of 14% over the total sugar yield obtained for densified cellulosic conversion-LE pretreatment. This result indicates that lignin extraction is an effective method of not only allowing for formation of CIII, but for improving sugar yields over the same process without lignin extraction, while simultaneously decreasing the enzyme loadings as compared to the same process without lignin extraction.

StEx showed only a moderate sugar yield (47.6±0.9 kg/100 kg densified sugarcane bagasse), even with 25 mg/g glucan of enzyme loading. This low sugar yield is mainly due to lower polysaccharide recovery after the pretreatment step. Since StEx requires high reaction seventies for improving cellulose digestibility, sugar degradation occurs, leading to the formation of products such as furans, which hamper sugar production. Additionally, the leftover solids from StEx-pretreatment required substantial washing which led to soluble sugar losses. Furthermore, unlike densified cellulosic conversion-LE pretreatment and EA, there is neither formation of CIII nor lignin removal during StEX pretreatment to help improve the susceptibility of polysaccharides to enzyme attack.

The ethanol yields from pretreated-LE/CIII-densified sugarcane bagasse at 100° C. with 1:1 NH₃:BM loading (g/g) and 15 mg enzyme/g glucan were comparable to that found for loose sugarcane bagasse subject to an EA pretreatment at 120° C. with 6:1 NH₃:BM (g/g) (26.9±0.0 kg vs. 27.6±0.4 kg of ethanol/100 kg densified sugarcane bagasse, respectively). Both pretreated-LE/CIII-densified sugarcane bagasse hydrolysates and EA pretreated/CIII-containing loose sugarcane bagasse hydrolysates were highly fermentable due to extraction of lignin-based inhibitors, while preserving the microbial nutrient availability. Although densified cellulosic conversion-LE pretreatment offers slightly lower experimental biofuel potential, based on the available sugars, it had better performance than EA. The pretreatment was performed at lower ammonia loadings (83% reduction relative to EA) and pressures (850 psi vs. 1200 psi). This contributes to lower OPEX (ammonia recovering costs) and lower CAPEX (lower pressure resistant pretreatment unit).

Taking into consideration that most soluble sugars obtained in the densified cellulosic conversion-LE pretreatment were fermented to ethanol with a metabolic yield of 97.5%, the ethanol yield was as high as 36.0 kg/100 kg densified sugarcane bagasse, which represents a remarkable achievement in terms of pretreatment performance. In addition, the ability of a densified cellulosic conversion-LE pretreatment to remove lignin-derived inhibitory compounds as compared to AFEX™ and StEx provides an additional advantage for the production of ethanol. For instance, for all densified cellulosic conversion-LE pretreatment experiments, an improvement of approximately 6% in ethanol yield was found.

The importance of lignin extraction can also be observed when comparing the densified cellulosic conversion pretreatment to the densified cellulosic conversion-LE pretreatment. Interestingly, at 75° C., the densified cellulosic conversion-LE pretreatment offered comparable ethanol yield to that found for densified cellulosic conversion pretreatment at 100° C. These results indicate that use of lignin extraction, together with a decrease in the operational temperature and pressure, as compared to performing this process without lignin extraction, can contribute to lower OPEX and CAPEX, without compromising the ethanol yield.

When subjected to hydrolysis, both the pretreated/CIII-densified sugarcane bagasse and the pretreated-LE/CIII-densified sugarcane bagasse, showed a remarkable improvement in ethanol yields over the known technologies tested, with enzyme loading savings of approximately 40%. Hydrolyzed AFEX™-pretreated/densified sugarcane bagasse also showed a relatively high ethanol yield (25.6±0.7 kg/00 kg of densified sugarcane bagasse), while the hydrolysate resulting from the StEx-pretreated whole slurry showed very low performance (16.2±0.4 kg ethanol/100 kg densified sugarcane bagasse) for the production of targeted biofuel. Densified cellulosic conversion pretreatment conditions used on the densified sugarcane bagasse were used without attempting to optimize for other feedstocks.

Figure 22:
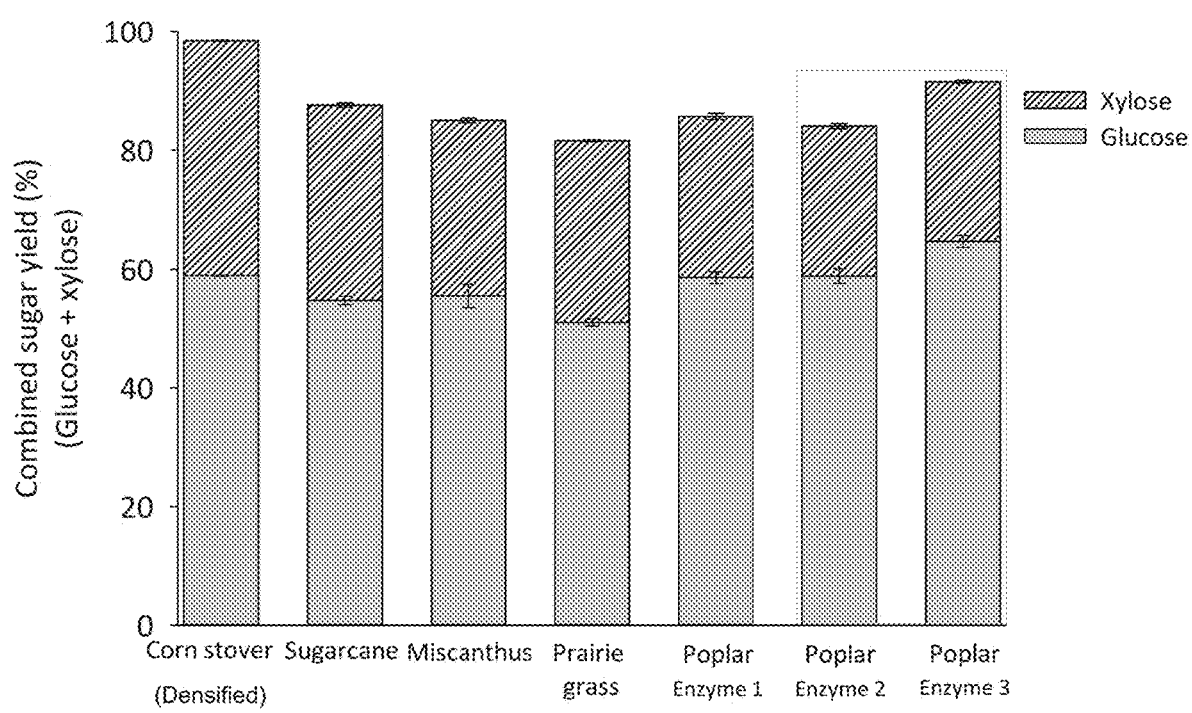
FIG. 22 is a bar graph comparing total reducing sugar yields of pretreated/CIII-densified biomass including, sugarcane bagasse, poplar, corn stover, miscanthus and prairie grass after being subject to a densified cellulosic conversion pretreatment process according to various embodiments.

FIG. 22 summarizes the impact of known densified cellulosic conversion pretreatment operational condition (100° C., 6 hr, 850 psi and 1:1 $NH_3$:BM (g/g)) on the enzymatic digestibility of pretreated/CIII-densified corn stover, sugarcane bagasse, prairie cord grass, miscanthus and poplar after 96 hr of enzymatic hydrolysis. It indicates that the biomass subjected to the densified cellulosic conversion pretreatment generated combined sugar yields higher than 80% for all the biomasses, despite their differences in terms of cell wall chemical composition and polysaccharide linkages presented in grasses and woody biomasses. Enzymatic hydrolysis experiments were carried out with 30 mg protein/g glucan at 1% glucan loading (w/w, glucan). The enzymatic cocktails used for corn stover, sugarcane bagasse and miscanthus enzymatic hydrolysis experiments were composed of Cellic® 71% CTec3: 23% HTec3: 6% Multifect Pectinase, on a protein basis, as previously optimized for the densified cellulosic conversion pretreatment-of densified sugarcane bagasse.

Figure 23:
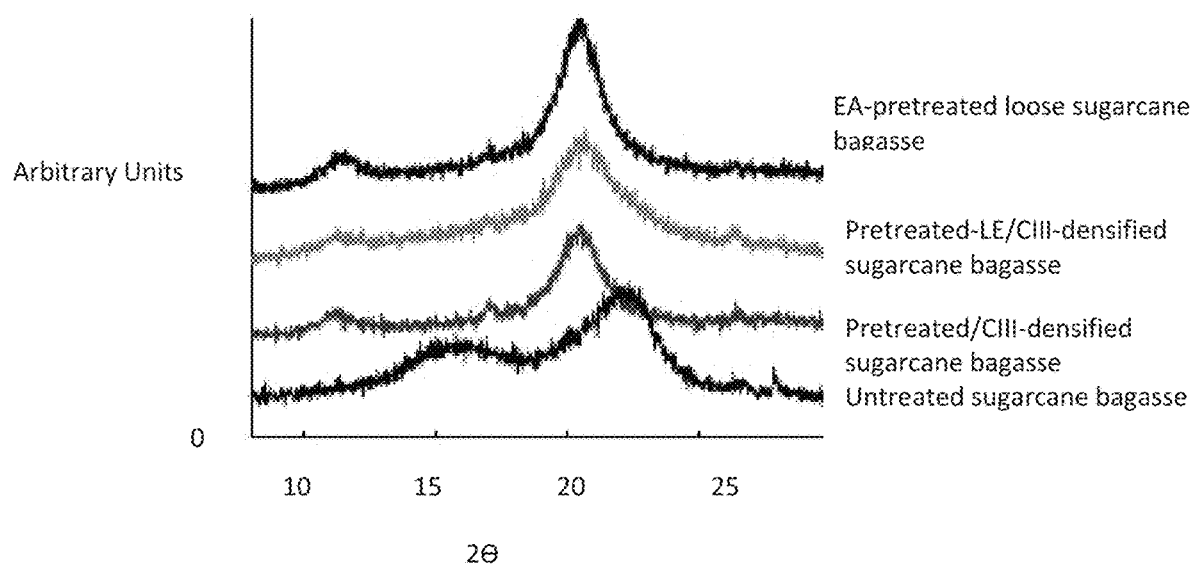
FIG. 23 is an XRD pattern of untreated densified sugarcane bagasse, pretreated/CIII-densified sugarcane bagasse and pretreated-LE/CIII-densified sugarcane bagasse (100° C., 850 psi, 3.5 hr, NH$_3$:BM ratio 1:1 (g/g)) as compared to EA pretreated/CIII-containing loose biomass (120° C., 30 min, 6:1 NH$_3$:BM (g/g)) showing that substantially all cellulose I (CI) was converted into CIII according to various embodiments.

FIG. 23 is an XRD pattern of untreated densified sugarcane bagasse, pretreated/CIII-densified sugarcane bagasse and pretreated-LE/CIII-densified sugarcane bagasse (100° C., 850 psi, 3.5 hr, $NH_3$:BM ratio 1:1 (g/g)) as compared to EA pretreated/CIII-containing loose biomass (120° C., 30 min, 6:1 $NH_3$:BM (g/g)) showing that substantially all cellulose I (CI) was converted into CIII according to various embodiments.

In addition, the effect of changing enzyme ratio on enzymatic cocktails was also examined for poplar. Enzyme 1: Cellic® brand CTec3, HTec3 and Multifect Pectinase in ratios (protein dwb) of 71%, 23% and 6%, respectively. Enzyme 2: Cellic® brand CTec3, HTec3 and Multifect Pectinase in ratios (protein dwb) of 75%, 25% and 3%, respectively. Enzyme 3: Cellic® brand CTec3, HTec3 and Multifect Pectinase in ratios (protein dwb) of 50%, 20% and 30%, respectively.

The effect of enzyme ratio on the performance of densified cellulosic conversion pretreatment-pretreated poplar for the production of fermentable sugars was tested. The highest combined sugar yield of 91.5±1% was obtained for "Enzyme 3" condition, which corresponds to an improvement of approximately 9% in comparison with the "Enzyme 2" condition. These key findings suggest that customizing the enzymatic cocktail for biomass type is effective.

Conclusion

Biorefineries for a large-scale bio-economy require highly available, consistent and year round available source of feedstocks.[19] However, there is no single feedstock able to meet affordable prices at fixed high availability to guarantee the productivity and profitability of the biorefineries. In this sense, various biomass sources, including agro-industrial residues, woody and dedicated energy crops, are required to feed these large-scale biorefineries around the globe. Yet, differences in chemical and physical properties between different biomass types have led to limited development of versatile industries.[20]

In various embodiments, the densified cellulosic conversion pretreatments disclosed herein can efficiently handle different types of feedstocks, regardless of their macromolecular composition and morphological structure, to produce high yields of fermentable sugars, thus providing feedstock-specific operational conditions. In various embodiments, the densified cellulosic conversion pretreatments disclosed herein can effectively process feedstocks including, but not limited to, agricultural residues, energy crops and hardwoods, into fermentable sugars useful in various bioproducts.

In one embodiment, a densified cellulosic conversion pretreatment is coupled with lignin extraction (i.e., densified cellulosic conversion pretreatment-LE) to produce highly digestible products, such as pretreated/CIII-densified sugarcane bagasse. Coupling with lignin extraction in this manner reduces the amount of enzyme needed during EH, in amounts up to 40% (such as from 30 to 40%, or 20 to 40%, including any range there between), as compared to conventional technologies, such as AFEX™ and StEx.

In various embodiments, pretreated-LE/CIII-densified sugarcane bagasse subject to EH can provide sugar yields comparable to a conventional EA pretreatment (using loose sugarcane bagasse). In one embodiment, pretreated-LE/CIII-densified sugarcane bagasse can produce from about 65 to 75 kg of fermentable sugars per 100 kg of untreated densified sugarcane bagasse (dwb), such as at least 68.8 kg of fermentable sugars per 100 kg of untreated densified sugarcane bagasse (dwb).

Use of a densified cellulosic conversion pretreatment process can also result in a reduction of ammonia use of up to 83% as compared to EA. Furthermore, the densified cellulosic conversion pretreatment-LE process can be effectively conducted at reduced temperatures (e.g., from about 75 to about 100° C.) and lower operating pressures (e.g., no greater than 450 psi) as compared to the temperatures and pressures used in EA (greater than 120° C. and greater than 450 psi, up to 1200 psi). However, if desired, higher temperatures and pressures can optionally be used, such as greater than 450 psi up to about 1000 psi as described herein. However, use of higher temperatures and pressures will increase the CAPEX due to higher pressure reactor requirement. Furthermore, IOEX-increased utility costs will be incurred with use of higher temperatures. Densified cellulosic conversion-LE pretreatment also allows for the production of hydrolysate having fermentable properties comparable to those produced by EA, up to, for example, 27.6 kg of ethanol per 100 kg of untreated sugarcane bagasse (dwb).

The parameters controlled during a densified cellulosic conversion pretreatment include, but are not limited to, temperature, residence time, pressure, density of the densified biomass and ammonia loading.

As noted in the '052 and '021 Applications, and as explained in the Sousa Article, and understood by those skilled in the art, a very specific set of conditions is required to convert cellulose I to III. Simply stating that ammonia is used as a pretreatment does not ensure that such a conversion occurs. Indeed, as shown in the Sousa Article, treatment under AFEX™ conditions does not result in a conversion of a majority of cellulose I to cellulose III.

The various bioproducts resulting from the novel densified cellulosic conversion pretreatments disclosed herein are intended to also include biochemicals, as well as cellulose, lignin and animal feed, to name a few. Additional details as to additional uses/end bioproducts for the various bioproducts which can be produced herein are discussed below:

Biochemicals

Biochemical conversion entails breaking down biomass to make the carbohydrates available for processing into sugars, which can then be converted into biofuels and bioproducts through the use of microorganisms and catalysts. These biochemicals are produced using microbial fermentation and can subsequently be converted to a number of high-value bio-based chemicals or materials. Building block chemicals that may be used include molecules with multiple functional groups that possess the potential to be transformed into new families of useful molecules. The twelve sugar-based building blocks are 1,4-diacids (succinic, fumaric and malic), 2,5-furan dicarboxylic acid, 3-hydroxy propionic acid, aspartic acid, glucaric acid, glutamic acid, itaconic acid, levulinic acid, 3-hydroxybutyrolactone, glycerol, sorbitol, and xylitol/arabinitol. A second-tier group of building blocks may also be useful. These include gluconic acid, lactic acid, malonic acid, propionic acid, the triacids, citric and aconitic; xylonic acid, acetoin, furfural, levoglucosan, lysine, serine and threonine. In other embodiments, biomass components such as aromatics, polysaccharides, and oils may be used.

Other bio-based chemicals that are commonly produced using sugars include, but are not limited to, amino acids, enzymes, organic acids, vitamins and related compounds, antibiotics, xanthan, hydroxymethyl furfural, levulinic acid, furfural, glucaric acid.

Applications for Cellulose

Pharmaceutical and cosmetic industries: Cellulose ethers and cellulose esters are broadly used in the formulation of dosage forms and healthcare products. These compounds are play roles in various types of pharmaceuticals, such as extended and delayed release coated dosage forms, extended and controlled release matrices, osmotic drug delivery systems, bio-adhesives and muco-adhesives, compression tablets as compressibility enhancers, liquid dosage forms as thickening agents and stabilizers, granules and tablets as binders, semisolid preparations as gelling agents and many other applications. These polymeric materials have also been used as fillers, taste maskers, free-flowing agents and pressure sensitive adhesives in transdermal patches.

Paper products: Cellulose is the major constituent of paper, paperboard, and card stock.

Fibers: Cellulose is the main ingredient of textiles made from cotton, linen, and other plant fibers. It can be turned into rayon, an important fiber that has been used for textiles since the beginning of the 20th century. Both cellophane and rayon are known as "regenerated cellulose fibers." These fibers are identical to cellulose in chemical structure and are usually made from dissolving pulp via viscose. The Lyocell process is another known method to produce rayon.

Consumables: Microcrystalline cellulose (E460i) and powdered cellulose (E460ii) are used as inactive fillers in drug tablets and as thickeners and stabilizers in processed foods. Cellulose powder is used, for example, in Parmesan cheese to prevent caking inside the package.

Research: Cellulose can be used in laboratories as a stationary phase for thin layer chromatography. Cellulose fibers are also used in liquid filtration, sometimes in combination with diatomaceous earth or other filtration media, to create a filter bed of inert material.

Building materials: Hydroxyl bonding of cellulose in water produces a sprayable, moldable material as an alternative to the use of plastics and resins. The recyclable material can be made water- and fire-resistant. It provides sufficient strength for use as a building material. Cellulose insulation made from recycled paper is becoming popular as an environmentally preferable material for building insulation. It can be treated with boric acid as a fire retardant.

Miscellaneous: Cellulose can be converted into cellophane, a thin transparent film. It is the base material for the celluloid that was used for photographic and movie films until the mid-1930s. Cellulose is used to make water-soluble adhesives and binders such as methyl cellulose and carboxymethyl cellulose which are used in wallpaper paste. Cellulose is further used to make hydrophilic and highly absorbent sponges. Cellulose is the raw material in the manufacture of nitrocellulose (cellulose nitrate) which is used in smokeless gunpowder.

Applications for Lignin

Concrete: Low levels of lignin and modified lignin yield high performance and concrete strength. Lignin can also be used as a concrete grinding aid to reduce damage of building external walls caused by moisture and acid rain, and to set retarders for a cement composition. Sulfonated lignin contributes to higher adsorption properties and zeta potential to cement particles and therefore show better dispersion effect to the cement matrix. Selective lignins can improve the compressive strength of cement pastes.

Antioxidants: Lignin particles act as free radical scavengers. Lignin provides thermal protection to styrene/butadiene/rubber polymers, polypropylene, polycarprolactam, and the like. Lignin natural antioxidant properties are useful in cosmetic and topical formulations. Lignin sulfonate-containing cosmetic compositions can be developed for decorative use on skin.

Asphalt: Asphalt is used as a crack filling composition involving quaternary ammonium salt, aliphatic amine, lignin amine, imidazoline and amide. Water stability of an asphalt mixture can be improved by adding 0.3% lignin fibers. Lignin amine additives provide a warm mix additive that can modify the combination state of asphalt and stone material surface by modifying the fluidity, while decreasing production cost of the asphalt mixtures.

Carbon fiber and related applications: Native lignin or industrial lignin can be used for carbon fibers. Carbon nanotubes can be made from lignin/lignosulfonates. Lignin-based activated carbon fibers can be prepared by initial synthesis of lignin-phenol-formaldehyde resin with varied lignin contents, such as 8-30%, and then used in melt spinning and thermal treatments. Kraft lignin has also been found to undergo strong adsorption on multi-walled carbon nanotubes.

Board Binders: Lignin can be used together with a diisocyanate for production of fiber board, strawboards, particleboards, oriented stand boards, wood fiber insulation boards, and the like. Grafted lignin or lignosulfonate component and resins are also known to be useful. A lignin based modifier can be added to a formaldehyde based binder system, such as phenol formaldehyde, urea formaldehyde, melamine formaldehyde, resorcinol formaldehyde, tannin formaldehyde resin, and the like. A lignin based modifier may be used for panel boards such as plywood, hard board, medium density fiberboard, particleboards, and the like.

Foams (plastic/polymers): Lignin based rigid polyurethane is known to have high flame retardance. Epoxy resins comprising an epoxy resin and curing agent, wherein the curing agent is a lignin-derived acid anhydride, can also be made. S-free lignin has been used for automatic brakes and epoxy resin for printed circuit boards. Polyphenylene oxide-based polymers and lignin esters blends exhibit modules of elasticity, tensile strength, and elongation of break values that are comparable or greater than the polyphenylene oxide-based polymer alone. Lignin can act as a water absorption inhibitor and as a fluidization agent when used with polyamide, when mixed in as a solid or a melt via injection molding, blow molding, or extrusion, or in blow extrusion to fabricate articles. The use of alkali lignin poly (propylene carbonate) is also known to improve thermal stability and mechanical properties.

Dust control: Lignin and glycerin in water can be applied on the surface of dust-yielding situations such as coal mines, coal transportation by rail car and stock yards, and the like. Selected calcium lignin sulfonate powders are known to stabilize widespread contamination following a nuclear accident, with field studies demonstrating a dependence on the weather conditions, and with the benefit being a short term corrective action. Dust movement can be controlled by spraying a road surface with an emulsion of asphalt, lignosulfonic and water.

Paper industry: Lignin is used as a sizing agent, while polymerization of acrylamide and hydroxymethylated are known to enhance tensile strength of paper by about 40%. Phenolic resins of wet curtain paper can also be made. Lignin can be used to make a packaging laminate comprising a barrier layer of lignin and oligo or polysaccharides, wherein the lignin and oligo- or polysaccharides are at least partly covalently bonded to each other in a matrix.

Chemical Production: Phenols can be prepared by reacting lignin with an HR-supplying solvent at elevated temperatures/pressures. Lignin de-polymerizaton provides routes to Cresols, catechols, resorcinols, quinones, vanillin and guaiacols.

Battery Production: Lignin can be used to enhance performance of energy storage devices. In certain applications, lignin forms a thin layer on graphite powder surface which prevents the graphite powder from decreasing HR+ overvoltage, while not affecting graphite powder performance. Lignin can also suppress generation of lead oxide and lead sulfate during drying. Additionally, use of lignin can shorten drying time.

Fuel Production: Alkaline fragments/purified lignin can be mixed with diesel using a blend of surfactants and emulsifiers. Lignin can also be catalytically converted to green gasoline/diesel by a combination of pyrolysis, thermal cracking, hydrocracking, catalytic cracking or hydro treatment. Lignin catalytic hydrogen reduction of carbon-oxygen bounds and the catalytic disproportionation of carbon-oxygen or carbon-carbon bonds are also useful.

Heating Applications: Artificial fire logs can be made using cellulosic materials and non-petroleum based materials together with lignin and 1,3-propanediol derived from renewable resources. Such products have improved flame properties. When added to densified wood biomass, lignin, such as Indulin AT brand lignin from Sigma-Aldrich, is known to produce high quality densified biomass with a high fuel value.

Grease Production: Calcium lignin sulfonate has been used to thicken base grease to form a lubricating grease. Lignin sulfonate provides antifriction properties to grease, thus providing longer lubrication life.

Dispersants: Dye dispersants are prepared from sulfate/sulfite pulping liquors crosslinked with sulfites/formaldehyde, with the products exhibiting good dispersion properties, heat-resistance stability, high temperature dispersion properties, fiber staining properties and azo dye reducing properties. Chemically modified lignin can also be used as a dispersing agent, complexing agent, flocculent, thickener or auxiliary agents for coating, paints and adhesives. Lignin sulfonates can be used as biodegradable and nontoxic emulsifiers or as dispersants for emulsion or dispersion polymerization. Jet printing ink can also be prepared using sulfonated lignin.

Agriculture: Sow release urea is composed of 90-99% urea with 1-10 wt % lignin. Lignin is used either directly or chemically modified as a binder, a dispersant agent for pesticides/herbicides, an emulsifier and as a heavy metal sequestrate. Lignin nutrient medium can be applied as an additive for restoring vegetation on road slop and on bare or deforested mountains. Oxidized and pulverized lignin, when blended with other chemicals, can be used as a soil water retention agent in acidic dry land and desert soil, or as a binder for fertilizer.

The following references are each hereby incorporated herein by reference in its entirety:
1. P. N. R. Vennestrom, C. M. Osmundsen, C. H R. Christensen and E. Taarning, *Angewandte Chemie-International Edition*, 2011, 50, 10502-10509.
2. B. Kamm, P. R. Gruber and M. Kamm, *Biorefineries-industrial processes and products. Status Quo and Future Directions*, Wiley-VCH Verlag GmbH & Co. KGaA, Weinheim, 2006.
3. A. E. Farrell, R. J. Plevin, B. T. Turner, A. D. Jones, M. O'hare and D. M. Kammen, *Science*, 2006, 311, 506-508.
4. A. Corma, S. Iborra and A. Velty, *Chem. Rev.*, 2007, 107, 2411-2502.
5. M. E. Himmel, S. Y. Ding, D. K. Johnson, W. S. Adney, M. R. Nimlos, J. W. Brady and T. D. Foust, *Science*, 2007, 315, 804-807.
6. S. Mohanram, D. Amat, J. Choudhary, A. Arora and L. Nain, *Sustain. Chem. Process.*, 2013, 1, 1.
7. B. Z. Li, V. Balan, Y. J. Yuan and B. E. Dale, *Bioresour. Technol.*, 2010, 101, 1285-1292.
8. L. da Costa Sousa, M. Jin, S. P. Chundawat, V. Bokade, X. Tang, A. Azarpira, F. Lu, U. Avci, J. Humpula and N. Uppugundla, *Energ. Environ. Sci.*, 2016, 9, 1215-1223.
9. A. Mittal, R. Katahira, B. S. Donohoe, S. Pattathil, S. Kandemkavil, M. L. Reed, M. J. Biddy and G. T. Beckham, *ACS Sustain. Chem. Eng.*, 2017, 5, 2544-2561.
10. S. P. S. Chundawat, M. S. Lipton, S. O. Purvine, N. Uppugundla, D. H R. Gao, V. Balan and B. E. Dale, *J. Proteome Res.*, 2011, 10, 4365-4372.
11. T. Mokomele, L. Costa Sousa, V. Balan, E. van Rensburg, B. E. Dale and J. Görgens, *Biotechnol. Biofuels*, 2018, Submitted.
12. V. Balan, L. D. Sousa, S. P. S. Chundawat, R. Vismeh, A. D. Jones and B. E. Dale, *J. Ind. Microbiol. Biotechnol.*, 2008, 35, 293-301.
13. A. Sluiter, B. Hames, R. Ruiz, C. Scarlata, J. Sluiter and D. Templeton, *Determination of sugars, byproducts and*

*degradation products in liquid fraction process samples*, Report NREL/TP-510-42623, National Renewable Energy Laboratory, Golden, Colo., USA, 2008.
14. A. Sluiter, B. Hames, R. Ruiz, C. Scarlata, J. Sluiter, D. Templeton and D. Crocker, *Determination of structural carbohydrates and lignin in biomass—Laboratory Analytical Procedure (LAP)*, Report NREL/TP-510-42618, National Renewable Energy Laboratory, Golden, Colo., USA, 2011.
15. S. P. Chundawat, R. Vismeh, L. N. Sharma, J. F. Humpula, L. da Costa Sousa, C. K. Chambliss, A. D. Jones, V. Balan and B. E. Dale, *Bioresour. Technol.*, 2010, 101, 8429-8438.
16. F. T. Silva, Obtenção de insumos quimicos a partir do aproveitamento integral do bagaço de cana, UNICAMP, 1995.
17. Y. Li, X. Li, F. Shen, Z. Wang, G. Yang, L. Lin, Y. Zhang, Y. Zeng and S. Deng, *Bioresour. Technol.*, 2014, 151, 54-62.
18. Y. N. Guragain, J. Wilson, S. Staggenborg, L. McKinney, D. Wang and P. V. Vadlani, *Biochem. Eng.* 1, 2013, 77, 198-207.
19. T. L. Richard, *Science,* 2010, 329, 793-796.
20. S. V. Vassilev, D. Baxter, L. K. Andersen and C. G. Vassileva, *Fuel,* 2010, 89, 913-933.

Although specific embodiments have been illustrated and described herein, it will be appreciated by those of ordinary skill in the art that any procedure that is calculated to achieve the same purpose may be substituted for the specific embodiments shown. For example, although the process has been discussed using particular types of densified biomass, including both cellulosic and lignocellulosic biomass, any type of densified biomass can be used. In the case of densified plant biomass, any type of densified plant biomass, such as grasses, rice straw and the like, for example, may be used. This application is intended to cover any adaptations or variations of the present subject matter. Therefore, it is manifestly intended that embodiments of this invention be limited only by the claims and the equivalents thereof.

What is claimed is:

1. A method of pretreating biomass comprising:
converting at least a majority of native cellulose $I_\beta$ to cellulose $III_I$ in densified biomass by pretreating the densified biomass with liquid ammonia, wherein the densified biomass is densified cellulosic biomass or densified lignocellulosic biomass and the liquid ammonia is anhydrous liquid ammonia or liquid ammonia comprising a solution of at least 80% ammonia, wherein the pretreating is performed at a temperature from about 50° C. to about 140° C. and at a pressure from about 14.7 to about 200 psi to generate pretreated/cellulose III-containing densified biomass, wherein total moisture content of the densified biomass and the solution is 10% or less and a weight ratio of liquid ammonia to the densified biomass is from about 0.2:1 up to less than 2:1.

2. The method of claim 1 wherein the weight ratio of the liquid ammonia to the densified biomass is from about 0.3:1 to about 1:1.

3. The method of claim 1 further comprising a lignin extraction step following the converting step to convert an additional 1% to 4% by weight of glucan.

4. The method of claim 1, wherein substantially all of the cellulose $I_\beta$ is converted to cellulose $III_I$.

5. The method of claim 1, wherein all of the cellulose $I_\beta$ is converted to cellulose $III_I$.

6. The method of claim 2, wherein the densified biomass is densified cellulosic biomass and the pretreated/cellulose III-containing densified biomass is pretreated/cellulose III-containing densified cellulosic biomass or wherein the densified biomass is densified lignocellulosic biomass and the pretreated/cellulose III-containing densified biomass is pretreated/cellulose III-containing lignocellulosic densified biomass or pretreated-LE/cellulose III-containing densified biomass.

7. The method of claim 5, wherein the densified lignocellulosic biomass is selected from corn stover, poplar, switchgrass, sugarcane bagasse, wheat straw, sorghum, energy cane, miscanthus, brewery spent grains, DDGS, soybean meal, and combinations thereof.

8. The method of claim 7, wherein the densified biomass is pretreated with the liquid ammonia for about 15 minutes to about 10 hours.

9. The method of claim 7, wherein the pretreatment is from about 1 to about 8 hours.

10. The method of claim 7, wherein the temperature is from about 50° C. to about 120° C.

11. The method of claim 7, wherein the densified biomass is untreated densified biomass or pretreated densified biomass containing no cellulose $III_I$.

12. The method of claim 11 wherein the pretreated densified biomass is pretreated using a pretreatment selected from ammonia, dilute acid, concentrated acid, steam explosion, alkali, organosolv, ionic liquid, biological, tetrahydrofuran (THF) and combinations thereof.

13. The method of claim 12, wherein the ammonia pretreatment is Ammonia Fiber Expansion (AFEX) and the alkali pretreatment is selected from NAOH, KOH, CaOH, and combinations thereof, and the method further comprises comprising recycling the liquid ammonia in a batch mode, a semi-batch mode or continuously.

14. The method of claim 7, wherein the pretreated/cellulose III-containing densified biomass is redensified to produce animal feed with or without added digestive enzymes.

15. The method of claim 7, further comprising an enzymatic hydrolysis step to hydrolyze the pretreated/cellulose III-containing densified biomass product, wherein said enzymatic hydrolysis step proceeds at a rate that is at least 1.5 times faster than a hydrolysis step performed using densified biomass that has not been pretreated with the liquid ammonia.

16. The method of claim 7, wherein the densified biomass is densified lignocellulosic biomass and the solution includes an organic solvent, wherein extractives present in the densified lignocellulosic biomass are removed during the liquid ammonia pretreatment.

17. The method of claim 7, wherein the pretreated/cellulose III-containing densified biomass is pretreated/cellulose III-containing lignocellulosic densified biomass containing lignin and/or hemicellulose, and the method further comprises extracting at least a portion of the lignin and/or hemicellulose from the pretreated/cellulose III-containing lignocellulosic densified biomass to produce an extracted product containing no cellulose $III_I$ and a pretreated densified biomass product, wherein said extracted product contains the lignin and/or hemicellulose.

18. The method of claim 17, wherein glucan and/or xylan is partially or wholly retained with the pretreated densified biomass product.

19. The method of claim 18, wherein the solvent is water or an organic solvent.

20. The method of claim 19, wherein the organic solvent is selected from acetone, ethanol, methanol, isopropanol, dichloromethane, methyl acetate, ethyl acetate, chloroform, and combinations thereof.

21. The method of claim 20, further comprising recycling the solvent in a batch mode, a semi-batch mode or continuously.

22. The method of claim 17, wherein the lignin is one of a plurality of plant cell wall components which are extracted in the extracting step.

23. The method of claim 22, wherein said plant cell wall components further include hemicellulose, arabinan, and combinations, and degradation products thereof.

24. The method of claim 20, wherein the pretreated/cellulose III-containing densified biomass is redensified to produce animal feed with or without added digestive enzymes.

25. A method of pretreating biomass comprising:
converting at least a majority of native cellulose $I_\beta$ to cellulose $III_I$ in densified biomass by pretreating the densified biomass with liquid ammonia for a period from about 15 minutes to 10 hours, wherein the densified biomass is densified cellulosic biomass or densified lignocellulosic biomass and the liquid ammonia is anhydrous liquid ammonia or liquid ammonia comprising a solution of at least 80% ammonia, wherein the pretreating is performed at a temperature from about 50° C. to about 140° C. and at pressure from about 14.7 to about 200 psi to generate pretreated/cellulose III-containing densified biomass, wherein total moisture content of the densified biomass and the solution is 10% or less and a weight ratio of liquid ammonia to the densified biomass is from about 0.2:1 up to less than 2:1; and further comprising an enzymatic hydrolysis step to hydrolyze the pretreated/cellulose III-containing densified biomass product, wherein said enzymatic hydrolysis step proceeds at a rate that is at least 1.5 times faster than a hydrolysis step performed using densified biomass that has not been pretreated with the liquid ammonia.

26. The method of claim 25 wherein the pressure is atmospheric pressure.

* * * * *

UNITED STATES PATENT AND TRADEMARK OFFICE
CERTIFICATE OF CORRECTION

PATENT NO. : 10,730,958 B2  
APPLICATION NO. : 15/916223  
DATED : August 4, 2020  
INVENTOR(S) : Venkatesh Balan and Leonardo da Costa Sousa Page 1 of 2

It is certified that error appears in the above-identified patent and that said Letters Patent is hereby corrected as shown below:

On the Title Page

Other Publications/Page 3/Column 1/Line 6/Li: reads as "(Afex)" and should read as "(AFEX)"

Other Publications/Page 5/Column 2/Line 51/Sousa: reads as "AFEXTM-Based" and should read as "AFEX™-Based"

In the Specification

Column 4/Line 14: reads as "(A)" and should read as "A)"

Column 5/Line 4: reads as "1)" and should read as "A)"

Column 5/Lines 6-7: reads as "and C) StEx-pretreated loose sugarcane bagasse, showing D)" and should read as "C) StEx-pretreated loose sugarcane bagasse, and D) StEx-pretreated CLM, showing"

Column 20/Line 44: reads as "and at least two times" and should read as "and is at least two times"

Column 22/Line 31: reads as "claim 1" and should read as "item 1"

Column 23/Line 30: reads as "item of claim 16" and should read as "method of item 16"

Column 24/Line 41: reads as "sized reduced" and should read as "size-reduced"

Column 24/Line 51: reads as "(source, 99.99%)" and should read as "(99.99%)"

Column 29/Lines 54-55: reads as "residence time, showed" and should read as "residence time showed"

Column 32/Line 46: reads as "bagasse s input" and should read as "bagasse is input"

Signed and Sealed this  
Twenty-seventh Day of October, 2020

Andrei Iancu  
*Director of the United States Patent and Trademark Office*

CERTIFICATE OF CORRECTION (continued)
U.S. Pat. No. 10,730,958 B2

Column 37/Lines 46-47: reads as "a pressure of" and should read as "the pressure to"

Column 37/Line 53: reads as "enzymatic hydrolysis yields sugarcane bagasse" and should read as "enzymatic hydrolysis yields. Sugarcane bagasse"

Column 38/Line 6: reads as "(w/w glucan))" and should read as "(w/w glucan)"

Column 41/Line 32: reads as "sugar yield for is" and should read as "sugar yield is"

Column 43/Line 22: reads as "kg/00 kg" and should read as "kg/100 kg"

Column 45/Lines 49-50: reads as "These compounds are play" and should read as "These compounds play"